United States Patent
Lueth et al.

(10) Patent No.: US 11,058,467 B2
(45) Date of Patent: Jul. 13, 2021

(54) BONE STABILIZATION SYSTEMS

(71) Applicant: GLOBUS MEDICAL, INC., Audubon, PA (US)

(72) Inventors: Jeffrey S. Lueth, Schwenksville, PA (US); David R. Jansen, Glenmoore, PA (US); Kathryn M. Ward, Phoenixville, PA (US); David Machamer, Glen Mills, PA (US)

(73) Assignee: Globus Medical, Inc., Audubon, PA (US)

( * ) Notice: Subject to any disclaimer, the term of this patent is extended or adjusted under 35 U.S.C. 154(b) by 203 days.

(21) Appl. No.: 16/444,345

(22) Filed: Jun. 18, 2019

(65) Prior Publication Data

US 2019/0365437 A1    Dec. 5, 2019

Related U.S. Application Data

(63) Continuation of application No. 15/882,303, filed on Jan. 29, 2018, now Pat. No. 10,368,928, which is a
(Continued)

(51) Int. Cl.
| | | |
|---|---|---|
| *A61B 17/80* | (2006.01) | |
| *A61B 17/86* | (2006.01) | |
| *A61B 17/17* | (2006.01) | |
| *A61B 17/84* | (2006.01) | |
| *A61B 90/00* | (2016.01) | |
| *A61B 17/68* | (2006.01) | |
| *A61B 17/064* | (2006.01) | |

(52) U.S. Cl.
CPC ...... *A61B 17/8057* (2013.01); *A61B 17/1728* (2013.01); *A61B 17/809* (2013.01); *A61B 17/8061* (2013.01); *A61B 17/846* (2013.01); *A61B 17/866* (2013.01); *A61B 90/06* (2016.02); *A61B 17/0642* (2013.01); *A61B 17/8047* (2013.01); *A61B 2017/0641* (2013.01); *A61B 2017/681* (2013.01); *A61B 2090/061* (2016.02); *A61B 2090/067* (2016.02)

(58) Field of Classification Search
CPC combination set(s) only.
See application file for complete search history.

(56) References Cited

U.S. PATENT DOCUMENTS

| | | | |
|---|---|---|---|
| 1,105,105 | A | 7/1914 | Sherman |
| 2,486,303 | A | 10/1949 | Longfellow |
(Continued)

FOREIGN PATENT DOCUMENTS

| | | |
|---|---|---|
| CN | 201987653 U | 9/2011 |
| CN | 202313691 U | 7/2012 |
(Continued)

*Primary Examiner* — Sameh R Boles

(57) ABSTRACT

Bone plates for engaging bone members are described herein. The bone plates can receive one or more screws to secure the bone plates to an underlying bone member. The one or more screws can be inserted into bone plate holes that can be considered locking or non-locking. The bone plates described herein can have particular combinations of locking and/or non-locking holes. In addition, instruments such as distal and proximal aiming guides can accompany the bone plates to guide one or more screws into the bone plates.

11 Claims, 57 Drawing Sheets

Related U.S. Application Data continuation-in-part of application No. 15/592,912, filed on May 11, 2017, now Pat. No. 10,905,477.

(60) Provisional application No. 62/470,470, filed on Mar. 13, 2017.

(56) References Cited

U.S. PATENT DOCUMENTS

| | | |
|---|---|---|
| 3,716,050 A | 2/1973 | Johnston |
| 4,493,317 A | 1/1985 | Klaue |
| 4,524,765 A | 6/1985 | de Zbikowski |
| 4,651,724 A | 3/1987 | Berentey et al. |
| 4,683,878 A | 8/1987 | Carter |
| 4,781,183 A | 11/1988 | Casey et al. |
| 4,867,144 A | 9/1989 | Karas et al. |
| 5,002,544 A | 3/1991 | Klaue et al. |
| 5,041,114 A | 8/1991 | Chapman et al. |
| 5,151,103 A | 9/1992 | Tepic et al. |
| 5,259,398 A | 11/1993 | Vrespa |
| 5,364,399 A | 11/1994 | Lowery et al. |
| 5,372,598 A | 12/1994 | Luhr et al. |
| 5,423,826 A | 6/1995 | Coates et al. |
| 5,601,553 A | 2/1997 | Trebing et al. |
| 5,676,667 A | 10/1997 | Hausman |
| 5,709,686 A | 1/1998 | Talos et al. |
| 5,718,704 A | 2/1998 | Medoff |
| 5,746,742 A | 5/1998 | Runciman et al. |
| 5,785,712 A | 7/1998 | Runciman et al. |
| 5,938,664 A | 8/1999 | Winquist et al. |
| 6,001,099 A | 12/1999 | Huebner |
| 6,096,040 A | 8/2000 | Esser |
| 6,152,927 A | 11/2000 | Farris et al. |
| 6,206,881 B1 | 3/2001 | Frigg et al. |
| 6,283,969 B1 | 9/2001 | Grusin et al. |
| 6,309,393 B1 | 10/2001 | Tepic et al. |
| 6,322,562 B1 | 11/2001 | Wolter |
| 6,364,882 B1 | 4/2002 | Orbay |
| 6,533,786 B1 | 3/2003 | Needham et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,866,665 B2 | 3/2005 | Orbay |
| 6,955,677 B2 | 10/2005 | Dahners |
| 6,974,461 B1 | 12/2005 | Wolter |
| 7,001,387 B2 | 2/2006 | Farris et al. |
| 7,063,701 B2 | 6/2006 | Michelson |
| 7,128,744 B2 | 10/2006 | Weaver et al. |
| 7,137,987 B2 | 11/2006 | Patterson et al. |
| 7,153,309 B2 | 12/2006 | Huebner et al. |
| 7,179,260 B2 | 2/2007 | Gerlach et al. |
| 7,250,053 B2 | 7/2007 | Orbay |
| 7,294,130 B2 | 11/2007 | Orbay |
| 7,322,983 B2 | 1/2008 | Harris |
| 7,341,589 B2 | 3/2008 | Weaver et al. |
| 7,354,441 B2 | 4/2008 | Frigg |
| 7,604,657 B2 | 10/2009 | Orbay et al. |
| 7,632,277 B2 | 12/2009 | Woll et al. |
| 7,635,381 B2 | 12/2009 | Orbay |
| 7,637,928 B2 | 12/2009 | Fernandez |
| 7,655,029 B2 | 2/2010 | Niedernberger et al. |
| 7,695,472 B2 | 4/2010 | Young |
| 7,722,653 B2 | 5/2010 | Young et al. |
| 7,740,648 B2 | 6/2010 | Young et al. |
| 7,776,076 B2 | 8/2010 | Grady, Jr. et al. |
| 7,857,838 B2 | 12/2010 | Orbay |
| 7,867,260 B2 | 1/2011 | Meyer et al. |
| 7,867,261 B2 | 1/2011 | Sixto, Jr. et al. |
| 7,875,062 B2 | 1/2011 | Lindemann et al. |
| 7,905,910 B2 | 3/2011 | Gerlach et al. |
| 7,909,858 B2 | 3/2011 | Gerlach et al. |
| 7,951,178 B2 | 5/2011 | Jensen |
| 7,951,179 B2 | 5/2011 | Matityahu |
| 7,976,570 B2 | 7/2011 | Wagner et al. |
| D643,121 S | 8/2011 | Millford et al. |
| D646,785 S | 10/2011 | Milford |
| 8,043,297 B2 | 10/2011 | Grady, Jr. et al. |
| 8,057,520 B2 | 11/2011 | Ducharme et al. |
| 8,062,296 B2 | 11/2011 | Orbay et al. |
| 8,100,953 B2 | 1/2012 | White et al. |
| 8,105,367 B2 | 1/2012 | Austin et al. |
| 8,114,081 B2 | 2/2012 | Kohut et al. |
| 8,118,846 B2 | 2/2012 | Leither et al. |
| 8,162,950 B2 | 4/2012 | Digeser et al. |
| 8,167,918 B2 | 5/2012 | Strnad et al. |
| 8,177,820 B2 | 5/2012 | Anapliotis et al. |
| 8,246,661 B2 | 8/2012 | Beutter et al. |
| 8,252,032 B2 | 8/2012 | White et al. |
| 8,257,403 B2 | 9/2012 | Den Hartog et al. |
| 8,257,405 B2 | 9/2012 | Haidukewych et al. |
| 8,257,406 B2 | 9/2012 | Kay et al. |
| 8,262,707 B2 | 9/2012 | Huebner et al. |
| 8,267,972 B1 | 9/2012 | Gehlert |
| 8,317,842 B2 | 11/2012 | Graham et al. |
| 8,323,321 B2 | 12/2012 | Gradl |
| 8,328,809 B2 * | 12/2012 | Wenk ................. A61B 17/1728 606/71 |
| 8,337,535 B2 | 12/2012 | White et al. |
| 8,343,155 B2 | 1/2013 | Fisher et al. |
| 8,382,807 B2 | 2/2013 | Austin et al. |
| 8,394,098 B2 | 3/2013 | Orbay et al. |
| 8,394,130 B2 | 3/2013 | Orbay et al. |
| 8,398,685 B2 | 3/2013 | McGarity et al. |
| 8,403,966 B2 | 3/2013 | Ralph et al. |
| 8,419,775 B2 | 4/2013 | Orbay et al. |
| 8,435,272 B2 | 5/2013 | Dougherty et al. |
| 8,439,918 B2 | 5/2013 | Gelfand |
| 8,444,679 B2 | 5/2013 | Ralph et al. |
| 8,491,593 B2 | 7/2013 | Prien et al. |
| 8,506,608 B2 | 8/2013 | Cerynik et al. |
| 8,512,385 B2 | 8/2013 | White et al. |
| 8,518,090 B2 | 8/2013 | Huebner et al. |
| 8,523,862 B2 | 9/2013 | Murashko, Jr. |
| 8,523,919 B2 | 9/2013 | Huebner et al. |
| 8,523,921 B2 | 9/2013 | Horan et al. |
| 8,551,095 B2 | 10/2013 | Fritzinger et al. |
| 8,568,462 B2 | 10/2013 | Sixto, Jr. et al. |
| 8,574,268 B2 | 11/2013 | Chan et al. |
| 8,597,334 B2 | 12/2013 | Mocanu |
| 8,603,147 B2 | 12/2013 | Sixto, Jr. et al. |
| 8,617,224 B2 | 12/2013 | Kozak et al. |
| 8,632,574 B2 | 1/2014 | Kortenbach et al. |
| 8,641,741 B2 | 2/2014 | Murashko, Jr. |
| 8,641,744 B2 | 2/2014 | Weaver et al. |
| 8,663,224 B2 | 3/2014 | Overes et al. |
| 8,728,082 B2 | 5/2014 | Fritzinger et al. |
| 8,728,126 B2 | 5/2014 | Steffen |
| 8,740,905 B2 | 6/2014 | Price et al. |
| 8,747,442 B2 | 6/2014 | Orbay et al. |
| 8,764,751 B2 | 7/2014 | Orbay et al. |
| 8,764,808 B2 | 7/2014 | Gonzalez-Hernandez |
| 8,777,998 B2 | 7/2014 | Daniels et al. |
| 8,790,376 B2 | 7/2014 | Fritzinger et al. |
| 8,790,377 B2 | 7/2014 | Ralph et al. |
| 8,808,333 B2 | 8/2014 | Kuster et al. |
| 8,808,334 B2 | 8/2014 | Strnad et al. |
| 8,834,532 B2 | 9/2014 | Velikov et al. |
| 8,834,537 B2 | 9/2014 | Castanada et al. |
| 8,852,246 B2 | 10/2014 | Hansson |
| 8,852,249 B2 | 10/2014 | Ahrens et al. |
| 8,864,802 B2 | 10/2014 | Schwager et al. |
| 8,870,931 B2 | 10/2014 | Dahners et al. |
| 8,888,825 B2 | 11/2014 | Batsch et al. |
| 8,906,076 B2 | 12/2014 | Mocanu et al. |
| 8,911,482 B2 | 12/2014 | Lee et al. |
| 8,926,675 B2 | 1/2015 | Leung et al. |
| 8,940,026 B2 | 1/2015 | Hilse et al. |
| 8,940,028 B2 | 1/2015 | Austin et al. |
| 8,940,029 B2 | 1/2015 | Leung et al. |
| 8,951,291 B2 | 2/2015 | Impellizzeri |
| 8,968,368 B2 | 3/2015 | Tepic |
| 9,011,457 B2 | 4/2015 | Grady, Jr. et al. |

(56) References Cited

U.S. PATENT DOCUMENTS

| | | |
|---|---|---|
| 9,023,052 B2 | 5/2015 | Lietz et al. |
| 9,050,151 B2 | 6/2015 | Schilter |
| 9,072,555 B2 | 7/2015 | Michel |
| 9,072,557 B2 | 7/2015 | Fierlbeck et al. |
| 9,107,678 B2 | 8/2015 | Murner et al. |
| 9,107,711 B2 | 8/2015 | Hainard |
| 9,107,713 B2 | 8/2015 | Horan et al. |
| 9,107,718 B2 | 8/2015 | Isch |
| 9,113,970 B2 | 8/2015 | Lewis et al. |
| 9,149,310 B2 | 10/2015 | Fritzinger et al. |
| 9,161,791 B2 | 10/2015 | Frigg |
| 9,161,795 B2 | 10/2015 | Chasbrummel et al. |
| 9,168,075 B2 | 10/2015 | Dell'Oca |
| 9,179,950 B2 | 11/2015 | Zajac et al. |
| 9,179,956 B2 | 11/2015 | Cerynik et al. |
| 9,180,020 B2 | 11/2015 | Gause et al. |
| 9,211,151 B2 | 12/2015 | Weaver et al. |
| 9,259,217 B2 | 2/2016 | Fritzinger et al. |
| 9,259,255 B2 | 2/2016 | Lewis et al. |
| 9,271,769 B2 | 3/2016 | Batsch et al. |
| 9,283,010 B2 | 3/2016 | Medoff et al. |
| 9,295,506 B2 | 3/2016 | Raven, III et al. |
| 9,314,284 B2 | 4/2016 | Chan et al. |
| 9,320,554 B2 | 4/2016 | Greenberg et al. |
| 9,322,562 B2 | 4/2016 | Takayama et al. |
| 9,370,388 B2 | 6/2016 | Globerman et al. |
| 9,433,407 B2 | 9/2016 | Fritzinger et al. |
| 9,433,452 B2 | 9/2016 | Weiner et al. |
| 9,468,479 B2 | 10/2016 | Marotta et al. |
| 9,480,512 B2 | 11/2016 | Orbay |
| 9,486,262 B2 | 11/2016 | Andermahr et al. |
| 9,492,213 B2 | 11/2016 | Orbay |
| 9,510,878 B2 | 12/2016 | Nanavati et al. |
| 9,510,880 B2 | 12/2016 | Terrill et al. |
| 9,526,543 B2 | 12/2016 | Castaneda et al. |
| 9,545,277 B2 | 1/2017 | Wolf et al. |
| 9,566,097 B2 | 2/2017 | Fierlbeck et al. |
| 9,636,157 B2 | 5/2017 | Medoff |
| 9,649,141 B2 | 5/2017 | Raven, III et al. |
| 9,668,794 B2 | 6/2017 | Kuster et al. |
| 2002/0045901 A1 | 4/2002 | Wagner et al. |
| 2004/0097937 A1 | 5/2004 | Pike et al. |
| 2005/0107796 A1 | 5/2005 | Gerlach et al. |
| 2005/0131413 A1 | 6/2005 | O'Driscoll et al. |
| 2005/0187551 A1 | 8/2005 | Orbay et al. |
| 2006/0149265 A1 | 7/2006 | James et al. |
| 2006/0241607 A1 | 10/2006 | Myerson et al. |
| 2007/0270849 A1 | 11/2007 | Orbay et al. |
| 2008/0021477 A1 | 1/2008 | Strnad et al. |
| 2008/0234749 A1 | 9/2008 | Forstein |
| 2008/0275510 A1 | 11/2008 | Schonhardt et al. |
| 2009/0024172 A1 | 1/2009 | Pizzicara |
| 2009/0024173 A1 | 1/2009 | Reis, Jr. |
| 2009/0118773 A1 | 5/2009 | James et al. |
| 2009/0198285 A1 | 8/2009 | Raven, III |
| 2009/0228010 A1 | 9/2009 | Gonzalez-Hernandez et al. |
| 2009/0228047 A1 | 9/2009 | Derouet et al. |
| 2009/0248084 A1 | 10/2009 | Hintermann |
| 2009/0281543 A1 | 11/2009 | Orbay et al. |
| 2009/0312760 A1 | 12/2009 | Forstein et al. |
| 2010/0030277 A1 | 2/2010 | Haidukewych et al. |
| 2010/0057086 A1 | 3/2010 | Price et al. |
| 2010/0114097 A1 | 5/2010 | Siravo et al. |
| 2010/0121326 A1 | 5/2010 | Woll et al. |
| 2010/0274247 A1 | 10/2010 | Grady, Jr. et al. |
| 2011/0106086 A1 | 5/2011 | Laird |
| 2011/0218580 A1 | 9/2011 | Schwager et al. |
| 2012/0059424 A1 | 3/2012 | Epperly et al. |
| 2012/0323284 A1 | 12/2012 | Baker et al. |
| 2013/0006246 A1 | 1/2013 | Dodson |
| 2013/0018426 A1 | 1/2013 | Tsai et al. |
| 2013/0060291 A1 | 3/2013 | Petersheim |
| 2013/0123841 A1 | 5/2013 | Lyon |
| 2013/0138156 A1 | 5/2013 | Derouet |
| 2013/0150902 A1 | 6/2013 | Leite |
| 2013/0165981 A1 | 6/2013 | Clasbrummet et al. |
| 2013/0211463 A1 | 8/2013 | Mizuno et al. |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |
| 2014/0094856 A1 | 4/2014 | Sinha |
| 2014/0121710 A1 | 5/2014 | Weaver et al. |
| 2014/0180345 A1 | 6/2014 | Chan et al. |
| 2014/0277178 A1 | 9/2014 | O'Kane et al. |
| 2014/0277181 A1 | 9/2014 | Garlock |
| 2014/0316473 A1 | 10/2014 | Pfeffer |
| 2014/0330320 A1 | 11/2014 | Wolter |
| 2014/0378975 A1 | 12/2014 | Castaneda et al. |
| 2015/0051650 A1 | 2/2015 | Verstreken et al. |
| 2015/0051651 A1 | 2/2015 | Terrill et al. |
| 2015/0073486 A1 | 3/2015 | Marotta et al. |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0182267 A1 | 7/2015 | Wolf et al. |
| 2015/0190185 A1 | 7/2015 | Koay et al. |
| 2015/0209091 A1 | 7/2015 | Sixto, Jr. et al. |
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |
| 2015/0327898 A1 | 11/2015 | Martin |
| 2015/0351816 A1 | 12/2015 | Lewis et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0045238 A1 | 2/2016 | Bohay et al. |
| 2016/0074081 A1 | 3/2016 | Weaver et al. |
| 2016/0166297 A1 | 6/2016 | Mighell et al. |
| 2016/0166298 A1 | 6/2016 | Mighell et al. |
| 2016/0262814 A1 | 9/2016 | Wainscott |
| 2016/0278828 A1 | 9/2016 | Ragghianti |
| 2016/0310183 A1 | 10/2016 | Shaw et al. |
| 2016/0310185 A1 | 10/2016 | Sixto et al. |
| 2016/0324552 A1 | 11/2016 | Baker et al. |
| 2016/0354122 A1 | 12/2016 | Montello et al. |
| 2017/0035478 A1 | 2/2017 | Andermahr et al. |
| 2017/0042592 A1 | 2/2017 | Kim |
| 2017/0042596 A9 | 2/2017 | Mighell et al. |
| 2017/0049493 A1 | 2/2017 | Gauneau et al. |
| 2017/0056081 A1 | 3/2017 | Langdale et al. |
| 2017/0065312 A1 | 3/2017 | Lauf et al. |
| 2017/0215931 A1 | 8/2017 | Cremer et al. |

FOREIGN PATENT DOCUMENTS

| | | |
|---|---|---|
| CN | 202821574 U | 3/2013 |
| CN | 202821575 U | 3/2013 |
| CN | 203506858 U | 4/2014 |
| CN | 203815563 U | 9/2014 |
| CN | 105982727 A | 10/2016 |
| FR | 2846870 A1 | 5/2004 |
| FR | 2928259 A1 | 9/2009 |
| JP | 2003210478 A | 7/2003 |
| TW | 201316942 A | 5/2013 |
| WO | 2011163092 A2 | 12/2011 |
| WO | 2016079504 A1 | 5/2016 |

\* cited by examiner

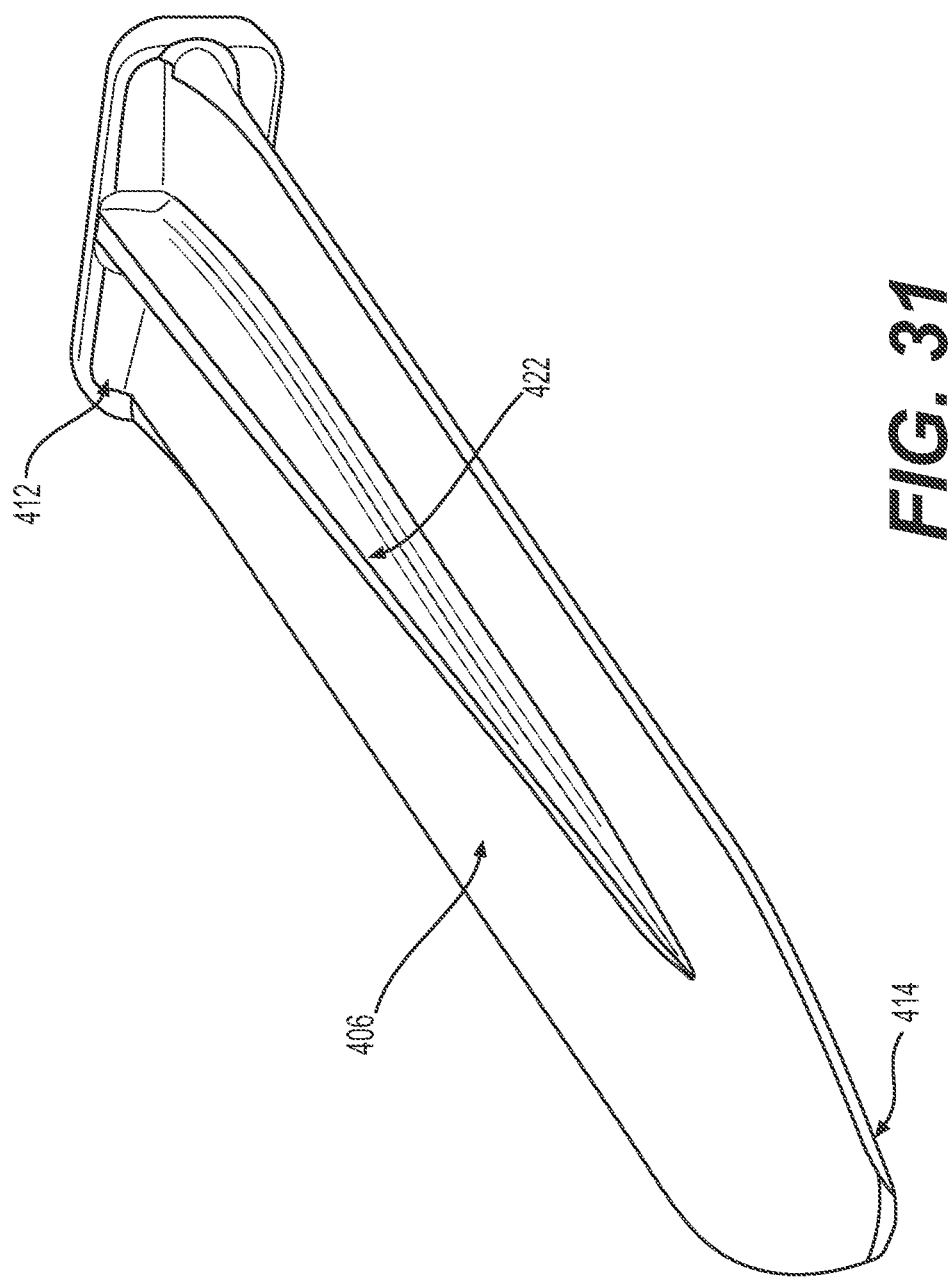

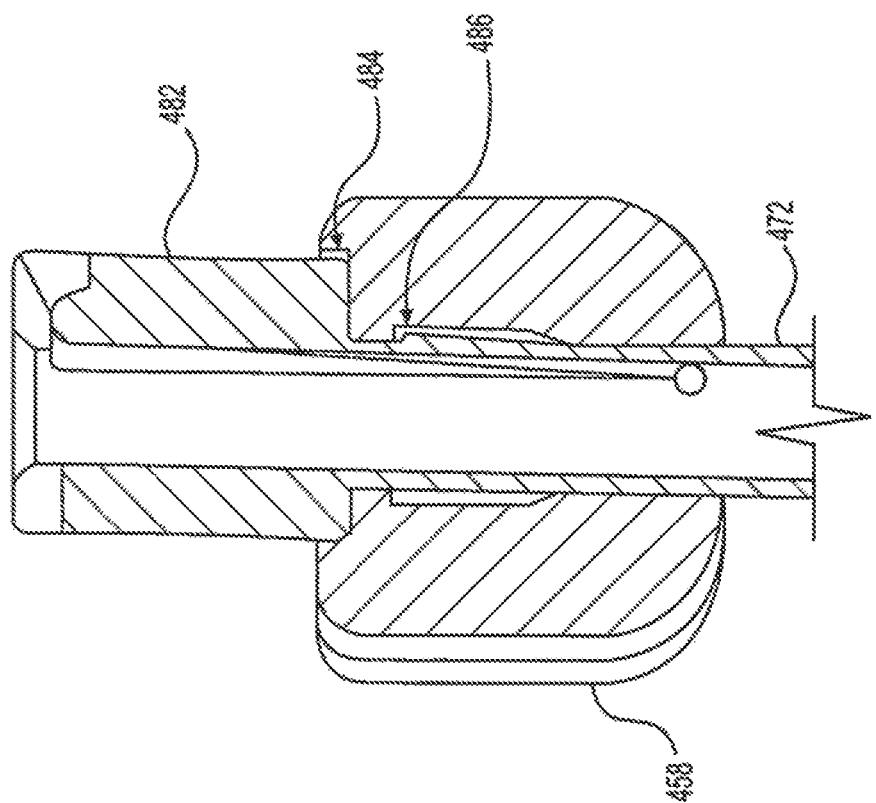
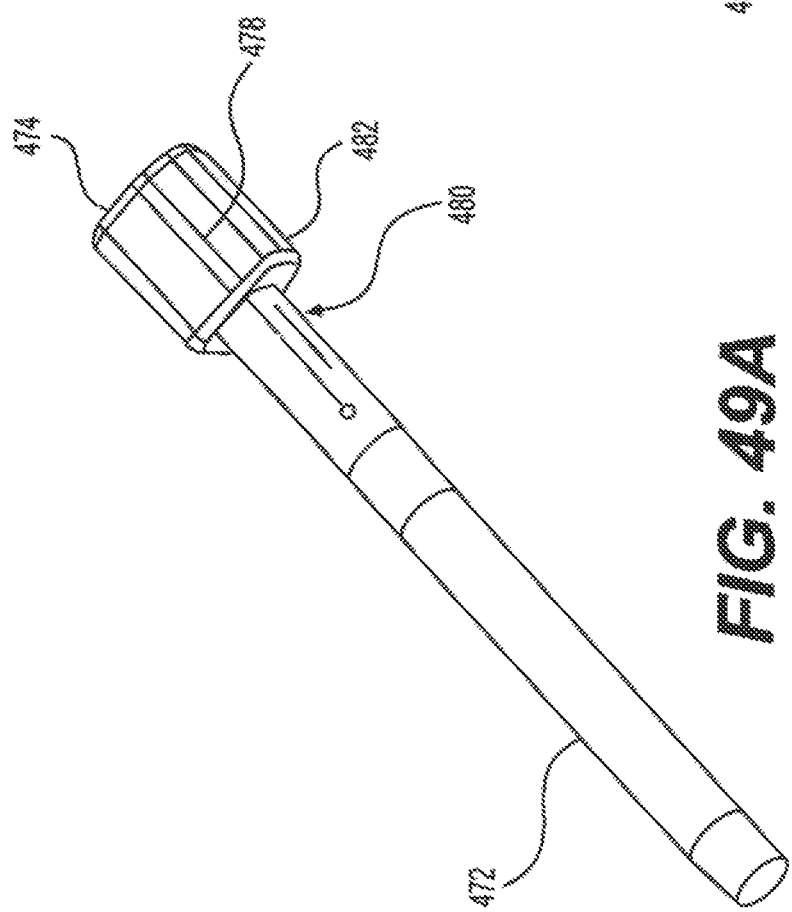

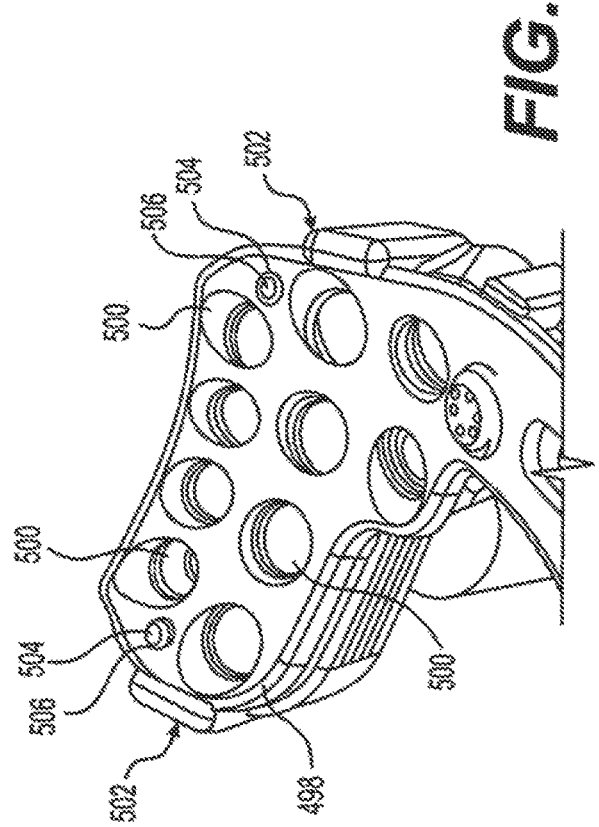
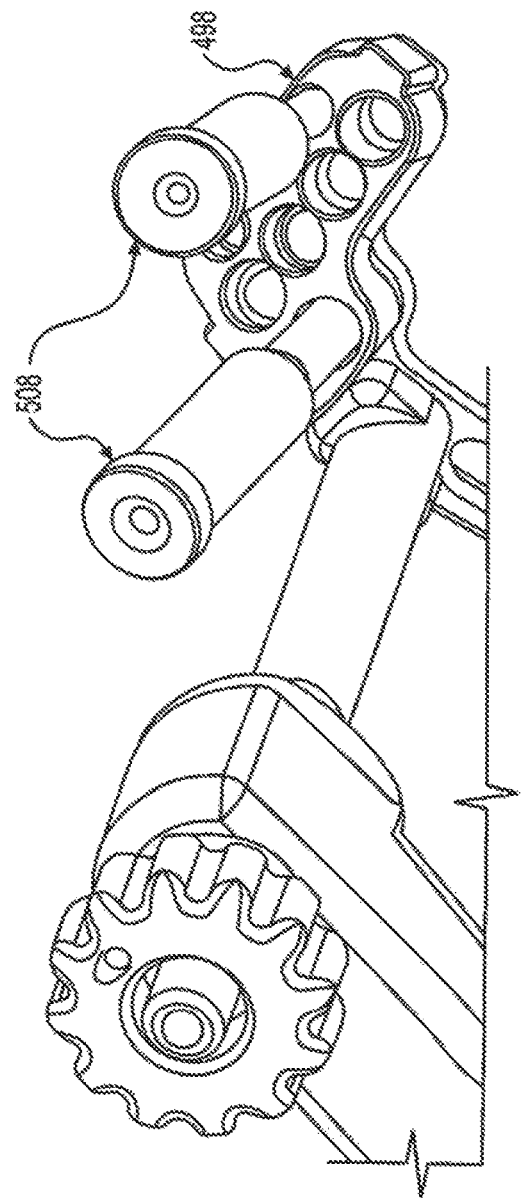

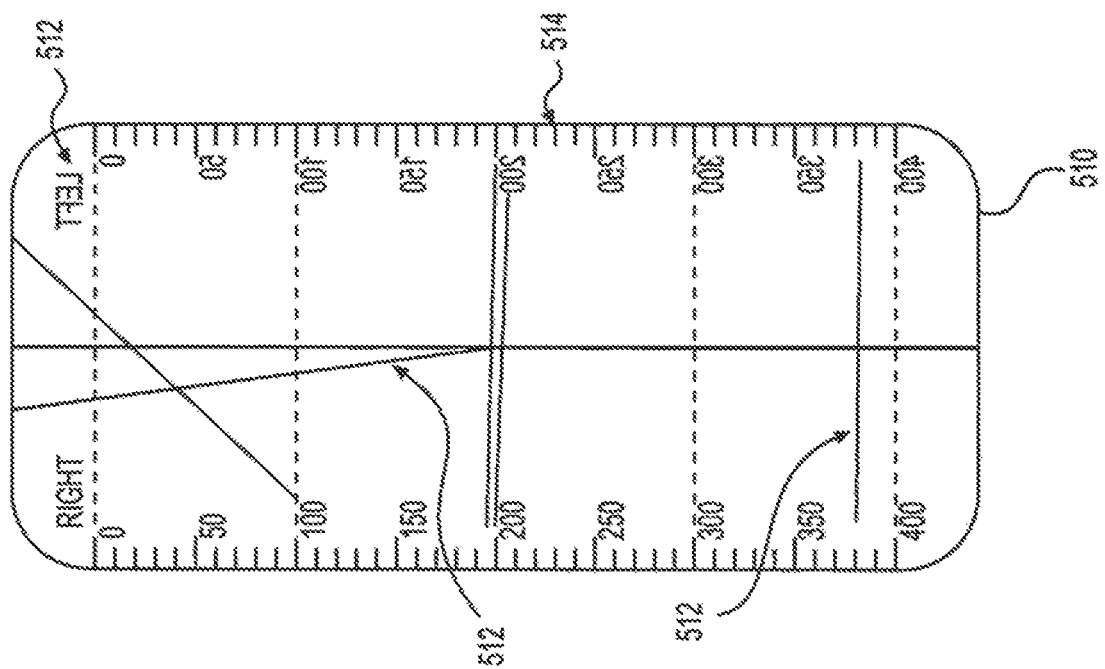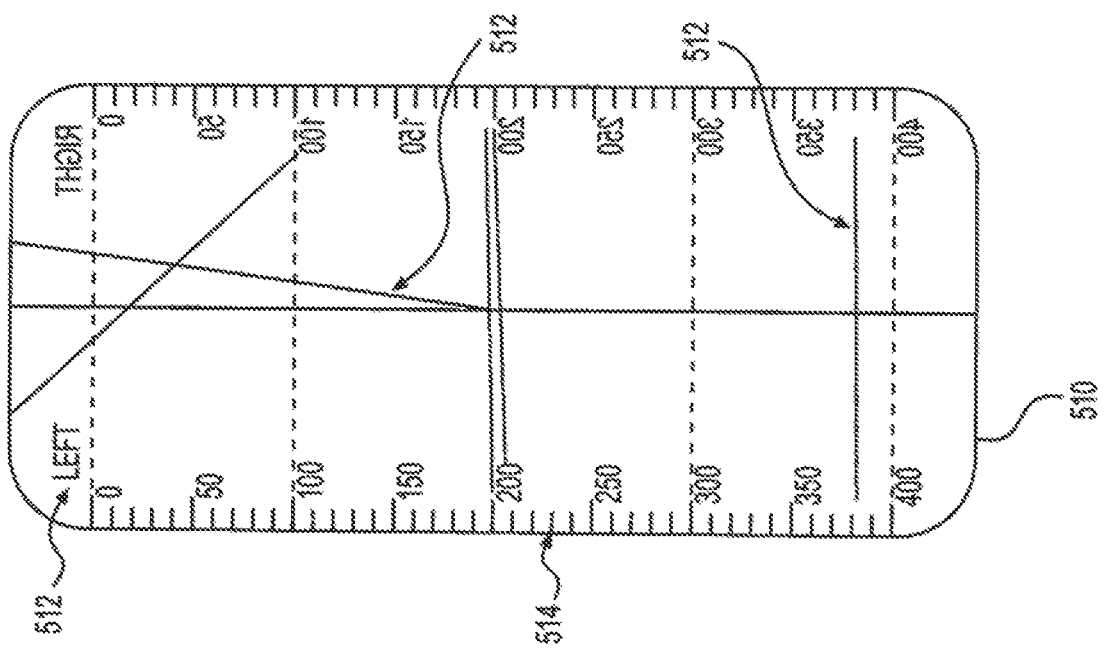
FIG. 52

BONE STABILIZATION SYSTEMS

CROSS-REFERENCE TO RELATED APPLICATIONS

This application is a continuation of U.S. patent application Ser. No. 15/882,303, filed on Jan. 29, 2018, which is a continuation-in-part of U.S. patent application Ser. No. 15/592,912, filed on May 11, 2017, which is a non-provisional application that claims priority to U.S. Provisional Application 62/470,470, filed Mar. 13, 2017, the entireties of which are herein incorporated by reference.

FIELD OF THE INVENTION

The present disclosure relates to surgical devices, and more particularly, stabilization systems including plates, for example, for trauma applications.

BACKGROUND OF THE INVENTION

Bone fractures can be healed using plating systems. During treatment, one or more screws are placed on either side of a fracture, thereby causing compression and healing of the fracture. There is a need for improved plating systems as well as mechanisms for accurate use of the plating systems.

Additionally, modern improvements in the treatment of bone deformities and comminuted traumatic fractures called for the establishment of "normal" mechanical axes of the human skeleton. Multiple authors published results of their anatomic studies with a variety of nomenclatures. Eventually, nomenclature was standardized and nominal and extreme values for "normal" mechanical and anatomic axes were settled on. These established angles are used now by medical professionals, such as orthopedic surgeons, around the world as a reference for correcting deformity and restoring normal joint alignment post-trauma. While some existing software packages aid with this correction in the evaluation of x-rays, there are no currently available devices for use under fluoroscopy in the operating room.

SUMMARY OF THE INVENTION

In accordance with the application, a system for treating a fracture in a bone is provided. In some embodiments, the system comprises: a bone plate configured to engage the bone, the bone plate comprising a proximal end, a distal end, a head portion, a neck portion and a shaft portion, wherein the head portion comprises a first row of holes and a second row of holes for receiving one or more fasteners therein, wherein the shaft portion comprises at least one additional hole for receiving a fastener therein; at least one fastener received in the head portion and positioned in the first row of holes or second row of holes; and at least one fastener received in the shaft portion and positioned in the at least one additional hole.

In other embodiments, the system comprises: a bone plate configured to engage the bone, the bone plate comprising a proximal end, a distal end, a head portion, a neck portion and a shaft portion, wherein the head portion comprises a first row of holes and a second row of holes for receiving one or more fasteners therein, wherein the shaft portion comprises at least one additional hole for receiving a fastener therein; at least one fastener received in the head portion and positioned in the first row of holes or second row of holes, wherein the at least one fastener is non-threaded; and at least one fastener received in the shaft portion and positioned in the at least one additional hole.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 31 is a top perspective view of a rafting blade in accordance with some embodiments.

FIGS. 49A-49B are diagrams showing exemplary tissue protection sleeves according to one embodiment of the present invention.

FIG. 51A is a top perspective view of the proximal aiming guide.

FIG. 51B is a diagram showing another top perspective view of the proximal aiming guide.

FIG. 52 shows one exemplary embodiment of a guide according to the present invention.

DETAILED DESCRIPTION OF THE INVENTION

Embodiments of the present application are generally directed to devices, systems and methods for bone stabilization. In particular, embodiments are directed to bone plates that extend across bone members to treat one or more fractures.

The plates described herein may be adapted to contact one or more of a femur, a distal tibia, a proximal tibia, a proximal humerus, a distal humerus, a clavicle, a fibula, an ulna, a radius, bones of the foot, bones of the hand, or other suitable bone or bones. The bone plates may be curved, contoured, straight, or flat. The plates may have a head portion that is contoured to match a particular bone surface, such as a metaphysis or diaphysis, flares out from the shaft portion, forms an L-shape, T-shape, Y-shape, etc., with the shaft portion, or that forms any other appropriate shape to fit the anatomy of the bone to be treated. The plates may be adapted to secure small or large bone fragments, single or multiple bone fragments, or otherwise secure one or more fractures. In particular, the systems may include a series of trauma plates and screws designed for the fixation of fractures and fragments in diaphyseal and metaphyseal bone. Different bone plates may be used to treat various types and locations of fractures.

The bone plates may be comprised of titanium, stainless steel, cobalt chrome, carbon composite, plastic or polymer—such as polyetheretherketone (PEEK), polyethylene, ultra high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body. Similarly, the bone plates may receive one or more screws or fasteners that may be comprised of titanium, cobalt chrome, cobalt-chrome-molybdenum, stainless steel, tungsten carbide, combinations or alloys of such materials or other appropriate biocompatible materials. Although the above list of materials includes many typical materials out of which bone plates and fasteners are made, it should be understood that bone plates and fasteners comprised of any appropriate material are contemplated.

Figure 6:
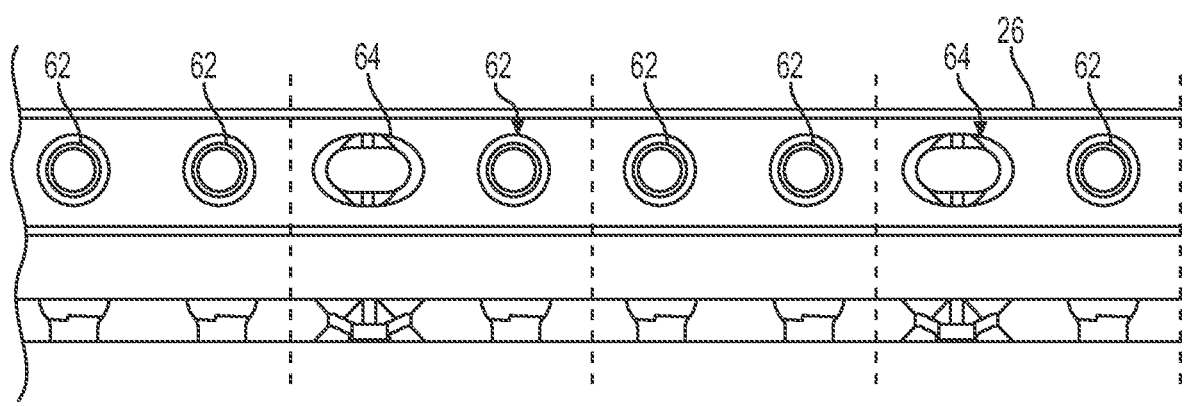
FIG. 6 is a top view of a shaft of the bone plate of FIG. 1 with a cross-sectional view shown beneath.

The bone plates described herein can be considered "locking" or "non-locking" plates. Locking plates include one or more openings for accepting one or more locking fasteners. The one or more openings can be partially or fully threaded. In some embodiments, these openings include fully threaded or stacked openings, which accept both locking and non-locking fasteners. In some embodiments, the locking fasteners include heads that are at least partially threaded. The locking fasteners can be monoaxial or polyaxial. One non-limiting example of a locking fastener (among others) is shown in FIG. 6 of U.S. application Ser. No. 15/405,368, filed Jan. 13, 2017, which is hereby incorporated by reference in its entirety.

Figure 4:
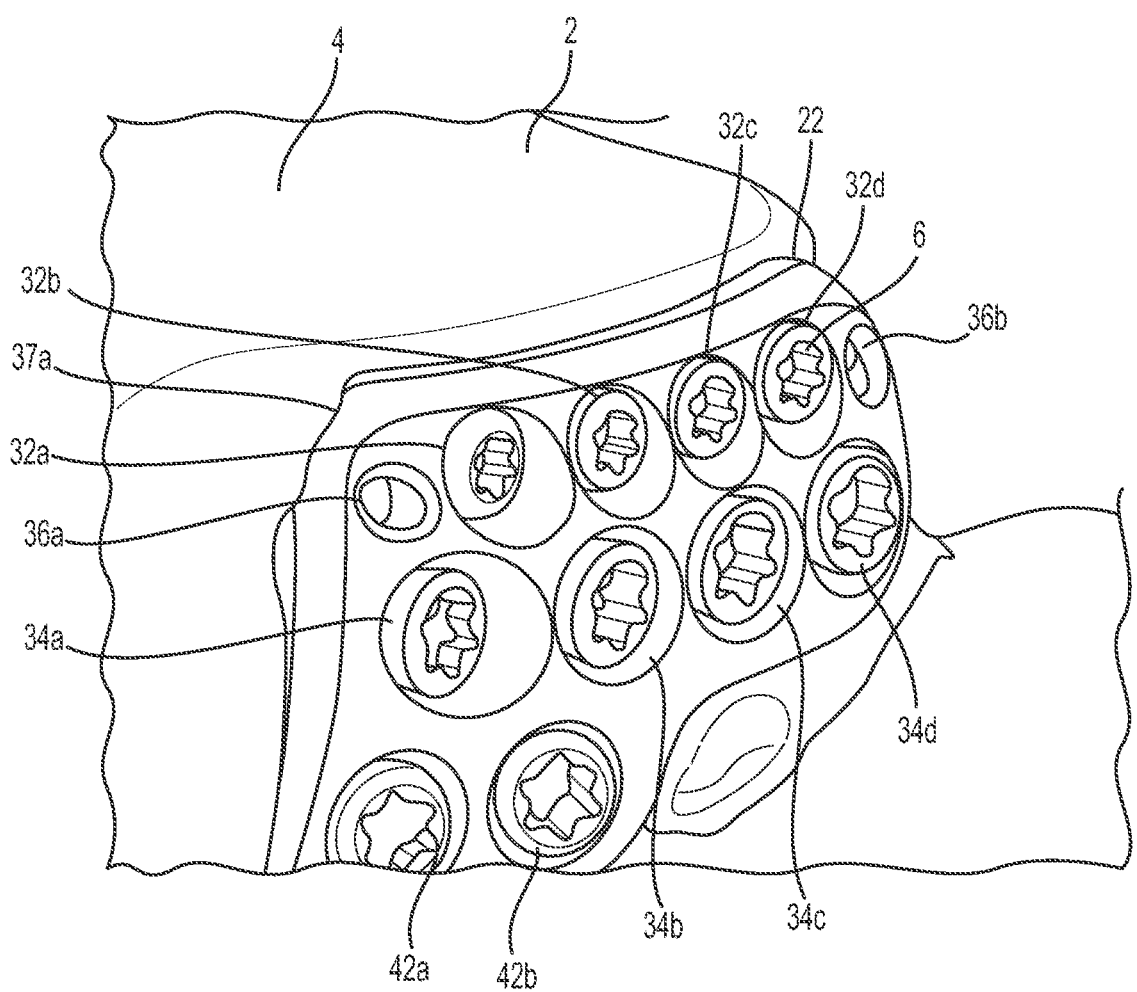
FIG. 4 is a view of the bone plate of FIG. 1 attached to a bone.

Non-locking plates include one or more openings for accepting one or more non-locking fasteners. The one or more openings at least in part be non-threaded. In some embodiments, these openings include non-threaded or stacked openings, which accept both locking and non-locking fasteners. In some embodiments, the non-locking fasteners include heads that are non-threaded. The non-locking fasteners can be monoaxial or polyaxial. One non-limiting example of a non-locking fastener (among others) is shown in FIG. 4 of U.S. application Ser. No. 15/405,368, filed Jan. 13, 2017, which is hereby incorporated by reference in its entirety. In some embodiments, the non-locking fasteners can include dynamic compression screws, which enable dynamic compression of an underlying bone.

Below are various examples of locking and non-locking plates attachable to bone. In some embodiments, locking plates may be thicker than non-locking plates. Locking plates may be useful for patients that have weaker bone, while non-locking plates may be useful for patients that have strong bone.

The locking and non-locking plates described below can be attached to different bones to treat fractures. In particular, the locking and non-locking plates can be used to treat fractures of the tibia, though one skilled in the art will appreciate that the novel plates described herein can be applied to fractures on other types of bone as well. With respect to the tibia, the locking and non-locking plates can be considered to be lateral, medial or posteromedial plates. In other words, the plates can be attached to a lateral, medial or posteromedial aspect of a tibia. One skilled in the art will appreciate, however, that the plates are not limited to their specific locations on the tibia, and that a surgeon may choose to apply a lateral plate medially or a medial plate laterally, if desired. In the present application, the bone plates shown in FIGS. 1 and 7-10 can be viewed as lateral plates, while the bone plates shown in FIGS. 11-17 can be viewed as medial or posteromedial plates.

Figure 1:
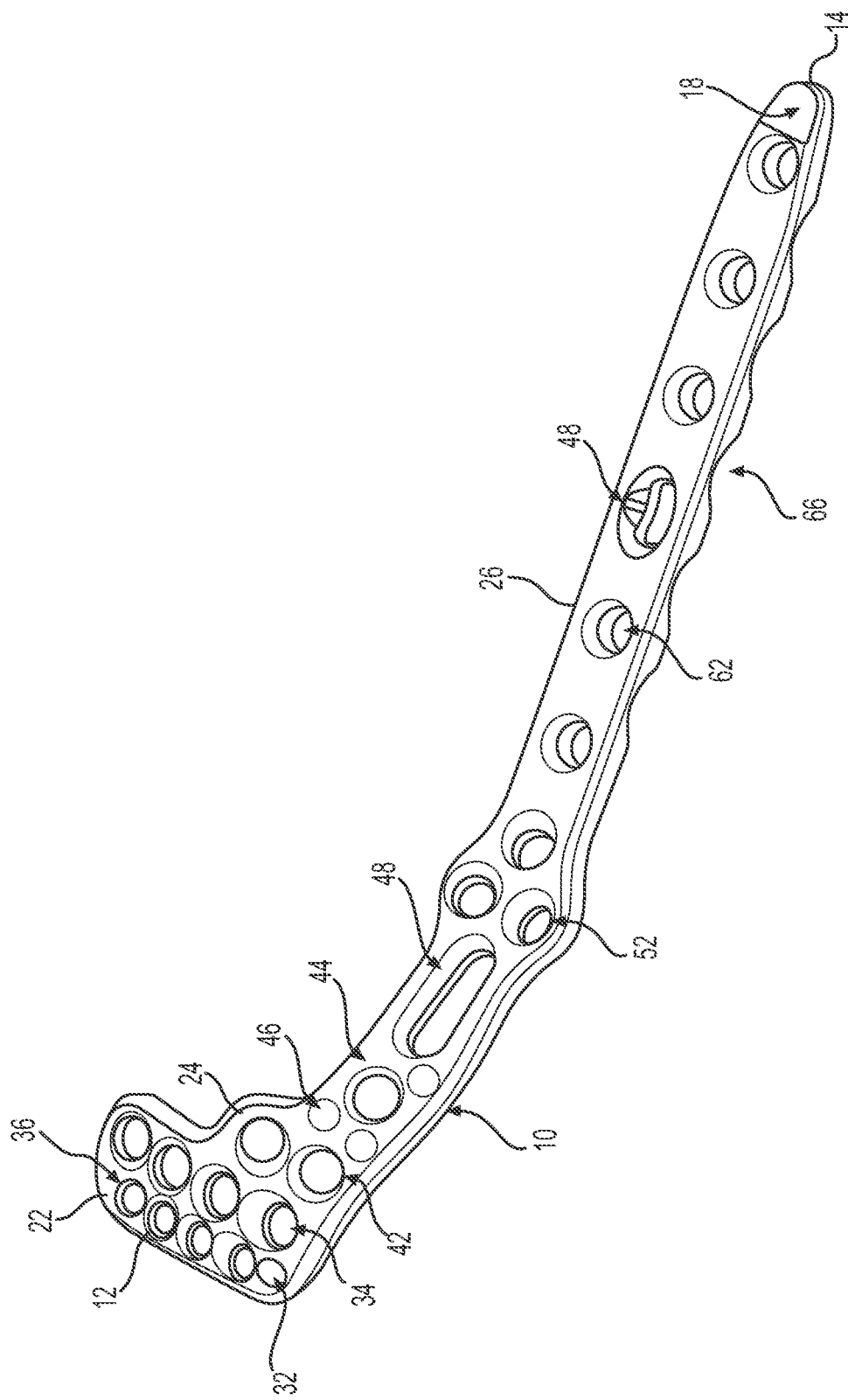
FIG. 1 is a top perspective view of a bone plate in accordance with some embodiments.

FIG. 1 is a top perspective view of a bone plate in accordance with some embodiments. In some embodiments, the bone plate 10 comprises a lateral locking plate, wherein at least some of the fasteners received therein are locking fasteners. The bone plate 10 comprises a proximal end 12 and a distal end 14. The bone plate 10 further comprises a head portion 22, a shaft portion 26, and a transitionary neck portion 24 between the head portion 22 and the shaft portion 26.

Figure 30:
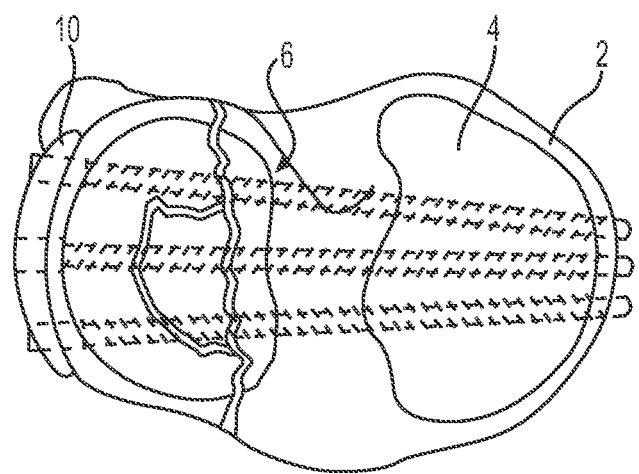
FIG. 30 is a top view of the bone plate of FIG. 28.

The head portion 22 comprises a widest portion of the bone plate 10 and is adjacent the proximal end 12. In some embodiments, the proximal end 12 is chamfered. Advantageously, the proximal end 12 contour and chamfer helps to position the bone plate 10 posterior to Gerdy's tubercle to minimize soft tissue irritation in a highly affected area. In some embodiments, the head portion 22 will be placed on a bone member (e.g., tibia) near an articular surface. Certain features of the head portion 22 are advantageously designed to prevent or resist subsidence of an articular surface. The head portion 22 comprises a first row of holes 32 and a second row of holes 34. In some embodiments, these holes 32, 34 are considered to be "rafting" holes that can receive rafting screws (e.g., as shown in FIG. 30) that advantageously support an articular surface of a joint and prevent subsidence. In some embodiments, the holes 32, 34 are locking holes that are at least partially threaded and designed to receive one or more polyaxial locking screws.

As shown in FIG. 1, the head portion 22 comprises a first row of holes 32 and a second row of holes 34, wherein the second row of holes 34 are larger than the first row of holes 32. For example, in some embodiments, the first row of holes 32 can be between 2.0 and 3.0 mm (e.g., 2.5 mm), while the second row of holes 34 can be between 3.0 and 4.0 mm (e.g., 3.5 mm). By providing two sets of holes 32, 34, the bone plate 10 advantageously accommodates a greater number of rafting screws, thereby providing greater support near a joint. In particular, the most proximal set of holes 32 are especially novel and advantageous, as they are designed to be adjacent the proximal end 12 of the bone plate 10. These holes 32 receive rafting screws that are closest to an articular surface of a joint. These holes 32 are advantageously smaller in size than holes 34, such that they can accommodate smaller rafting screws, which may be particularly hard to position in the limited space adjacent the articular surface. In some embodiments, the first row of holes 32 are offset from the second row of holes 34, while in other embodiments, the first row of holes 32 are aligned with the second row of holes 34. In some embodiments, the first row of holes 32 can have the same number of holes as the second row of holes, while in other embodiments, the first row of holes 32 can have a different number of holes as the second row of holes. In the present embodiment, the bone plate 10 include four holes 32 and four holes 34.

Figure 5:
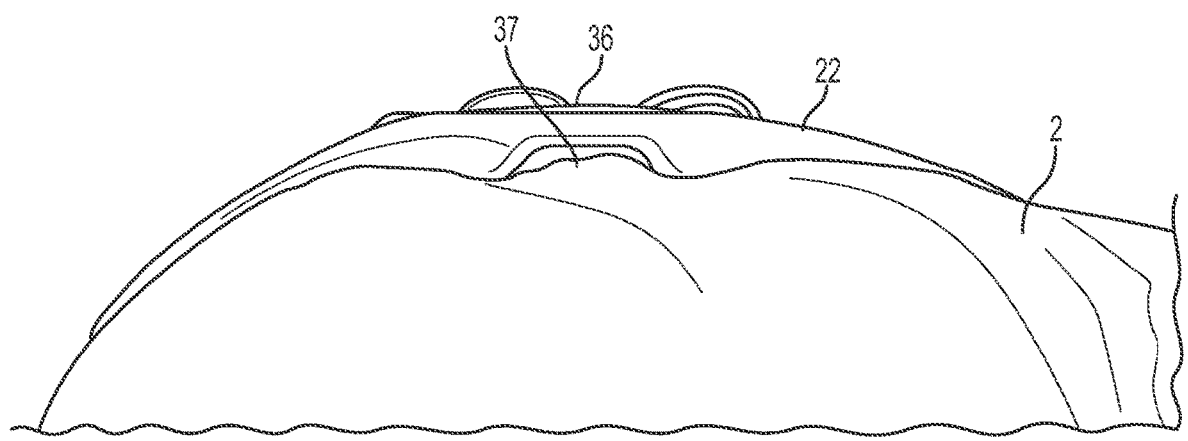
FIG. 5 is an alternative view of the bone plate of FIG. 1 attached to a bone.

As shown in FIG. 1, the head portion 22 further comprises one or more novel multi-purpose holes 36. In some embodiments, the multi-purpose holes 36 are advantageously designed to accommodate a k-wire as well as a suture. In some embodiments, the holes 36 are sized and positioned to receive a k-wire therein, thereby assisting in placement of the bone plate 10 on a bone member. The holes 36 are formed adjacent and continuously with one or more undercuts 37 (shown in FIGS. 2B and 3) of the bone plate 10. As shown in FIG. 5, the one or more undercuts 37 advantageously allow access to one or more sutures through the bone plate 10 even after the bone plate 10 is implanted on bone. The sutures can be used to attach the bone plate 10 to adjacent tissue, thereby further securing the bone plate 10 at or near a surgical site.

The neck portion 24 is a transitionary portion between the head portion 22 and the shaft portion 26. The neck portion 24 is less wide than the head portion 22, but has at least some portions that of equal or greater width than the shaft portion 26. As shown in FIG. 1, the neck portion 24 comprises a pair of locking holes 42, an instrument attachment hole 44, alignment indentations 46, a positioning slot, and three kickstand holes 52. Each of these features is described below.

The pair of locking holes 42 are positioned beneath the rafting holes 32, 34. In some embodiments, the locking holes 42 comprise polyaxial locking holes that are at least partially threaded. The pair of locking holes 42 are configured to receive one or more bone fasteners or screws to secure the bone plate 10 to an underlying bone member. In some embodiments, the pair of locking holes 42 are the same or similar width to the holes 34. In some embodiments, each of the locking holes 42 has a width between 3.0 and 4.0 mm (e.g., 3.5 mm).

Figure 18:
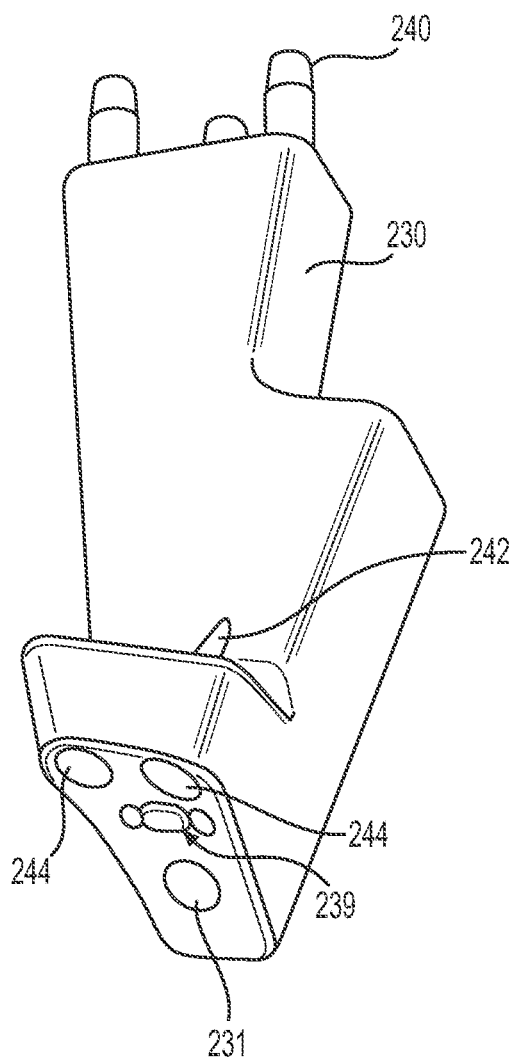
FIG. 18 is a side view of a mount of the aiming guide of FIG. 17.
Figure 21:
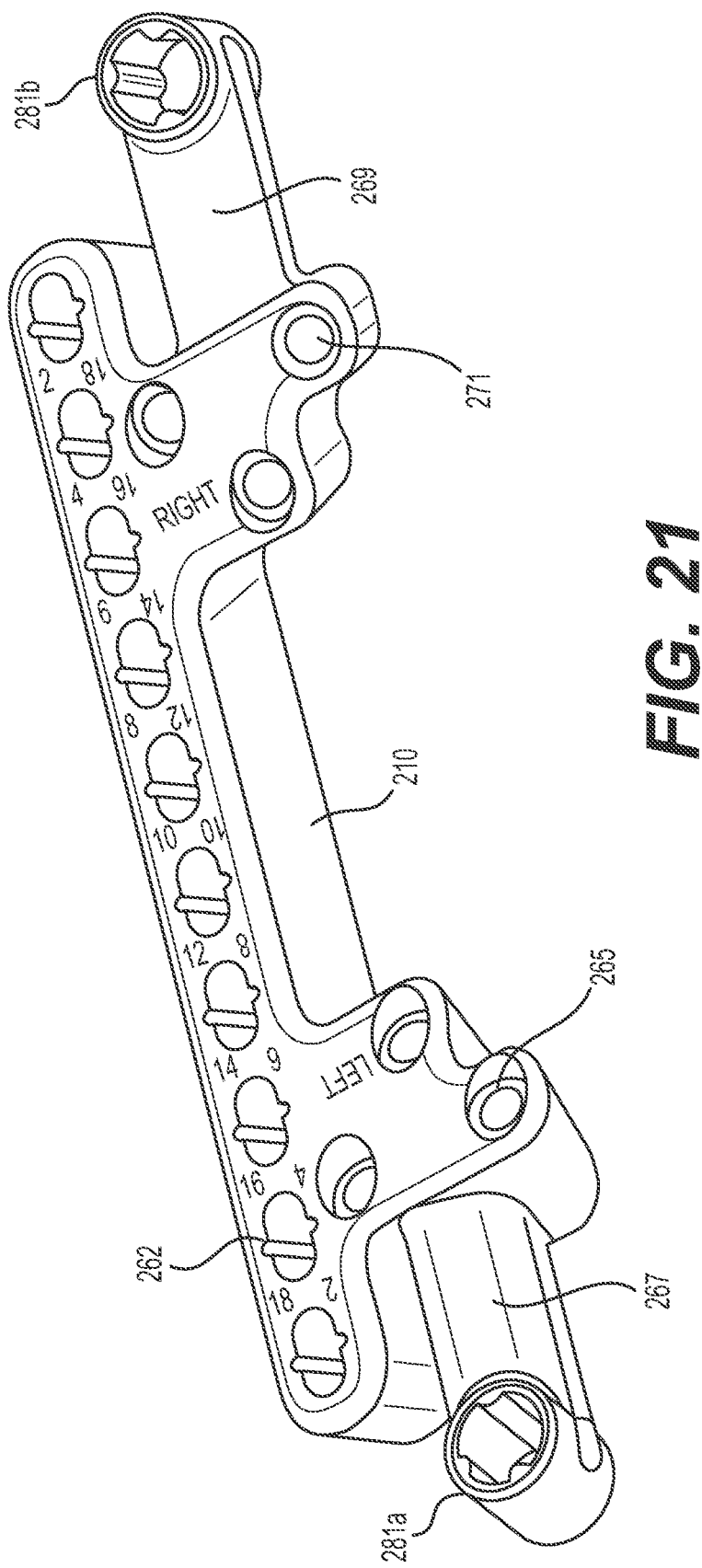
FIG. 21 is a top perspective view of the aiming guide of FIG. 20.

Below the pair of locking holes 42 are indentations 46 and an instrument attachment hole 44. The indentations 46 and instrument attachment hole 44 are designed to cooperate with an aiming guide, as shown in FIGS. 18 and 21. The aiming guide is particularly useful with lateral plates, and can be used to accurately guide one or more bone screws or fasteners into respective holes in a bone plate 10. In some embodiments, the indentations 46 comprise spherical indentations. Unlike other holes or openings in the bone plate 10, the indentations 46 do not extend completely through a plate. Rather, the indentations 46 are engaged by one or more ball-end pins (shown in FIG. 22) that extend outwardly from an attachment post of an aiming guide. The indentations 46 advantageously help to stabilize and position the aiming guide relative to the bone plate 10. While the bone plate 10 is shown as having three indentations 46, the bone plate 10 can include one, two, or more than three indentations 46. Between the indentations 46 is an instrument attachment hole 44. The instrument attachment hole 44 comprises a threaded hole that is designed to receive a threaded shaft (shown in FIG. 22) that also extends outwardly from an attachment post of an aiming guide. Once the aiming guide is stabilized via the indentations 46, the aiming guide can be attached to the bone plate 10 via threading of the threaded shaft.

A positioning slot 48 is located distally and beneath the indentations 46 and instrument attachment hole 44. The positioning slot 48 comprises an elongated opening that is designed to receive a first bone screw or fastener therein before finalizing a position of a bone plate 10 on bone. As the positioning slot 48 is elongated, the bone plate 10 can be slightly adjusted around a first bone fastener is needed. In some embodiments, the positioning slot 48 has a length that is greater than a length of any of the other holes that receive bone screws therein. In some embodiments, the positioning slot 48 has a length that is at least twice the length of a length of any of the other holes that receive bone screws therein. The first bone fastener can be provisionally placed in the positioning slot 48 prior to final tightening of the first bone screw. Upon proper orientation and placement of the bone plate 10, the first bone fastener can be finally tightened.

One or more kickstand holes 62 are provided distally from the positioning slot 48. In some instances, lateral plates may be preferred over medial plates, as they can often be implanted via a smaller incision with less risk to surrounding tissue. The one or more kickstand holes 62 are capable of receiving one or more bone fasteners that can treat medial fractures if desired. In other words, the kickstand holes 62 advantageously allow a medial fracture to be treated via support from just the lateral side. As shown in FIG. 1, the bone plate 10 includes at least three kickstand holes 62. In some embodiments, the kickstand holes 62 are fixed angle, stacked locking holes. By providing a triple kickstand construct with three kickstand holes 62, this advantageously accommodates up to three bone fasteners to better support a medial fracture. In some embodiments, the triple kickstand construct serves as a novel collection of kickstand holes 62 aimed at the anterior, middle, and posterior aspects of the medial proximal tibia, thereby providing the surgeon with options and enhanced versatility. The triple kickstand construct advantageously provides a surgeon with options for which fragments to target and allows the surgeon to customize construct rigidity with one or more screws or fasteners. In other embodiments, the kickstand construct will have a single kickstand hole, two kickstand holes, or more than three kickstand holes.

The shaft portion 26 comprises a distal portion of the bone plate 10 relative to the head portion 22 and neck portion 24. In some embodiments, the shaft portion 26 comprises a longest and narrowest portion of the bone plate 10. The shaft portion 26 comprises a number of openings or holes therein for receiving one or more bone fasteners. In the present embodiment, the shaft portion 26 comprises a plurality of holes 62 (e.g., five) that serve as fixed angled, stacked locking holes. These fixed angle, stacked locking holes allow mono-axial insertion of bone fasteners that can be locking or non-locking. In addition, as shown in FIG. 1, the shaft portion 26 of the bone plate 10 also comprises a bi-direction, dynamic compression slot 64 that is positioned in between the locking holes 62. The bi-directional dynamic compression slot 64 advantageously allows for static insertion of non-locking screws into the shaft of bone. They also allow for compression (e.g., 0.5 mm-2 mm) along the shaft of the bone through eccentric insertion of a non-locking screw. The holes 62 and slot 64 are capable of receiving one or more screws therein to secure the bone plate 10 to bone.

The distal portion of the shaft portion 26 further comprises a tapered tip 18. In some embodiments, the tapered tip 18 serves as an insertion tip that allows the plate 10 to be inserted beneath skin to a surgical site. The bone plate 10 can be positioned adjacent to bone (e.g., a tibia), whereby it can be fixed to the bone. In some embodiments, the tapered tip allows for simplified submuscular plate insertion to minimize incision length. As shown in FIG. 1, an underside of the shaft portion 26 of the bone plate 10 comprises a plurality of scallops 66. The scallops 66 form a scalloped contact surface which provides better frictional contact with a bone member. In some embodiments, the scalloped contact surface minimizes impact to the periosteal blood supply and allows some bending of the shaft portion 26 of the bone plate 10 without deforming threaded holes.

In some embodiments, the bone plate 10 provides an anatomic contour that accommodates a lateral aspect of the proximal tibia. In some embodiments, the bone plate 10 includes a proximal anterior portion (e.g., chamfered portion) that sits just posterior to Gerdy's tubercle, thereby assisting with positioning while minimizing soft tissue irritation.

Figure 2A:
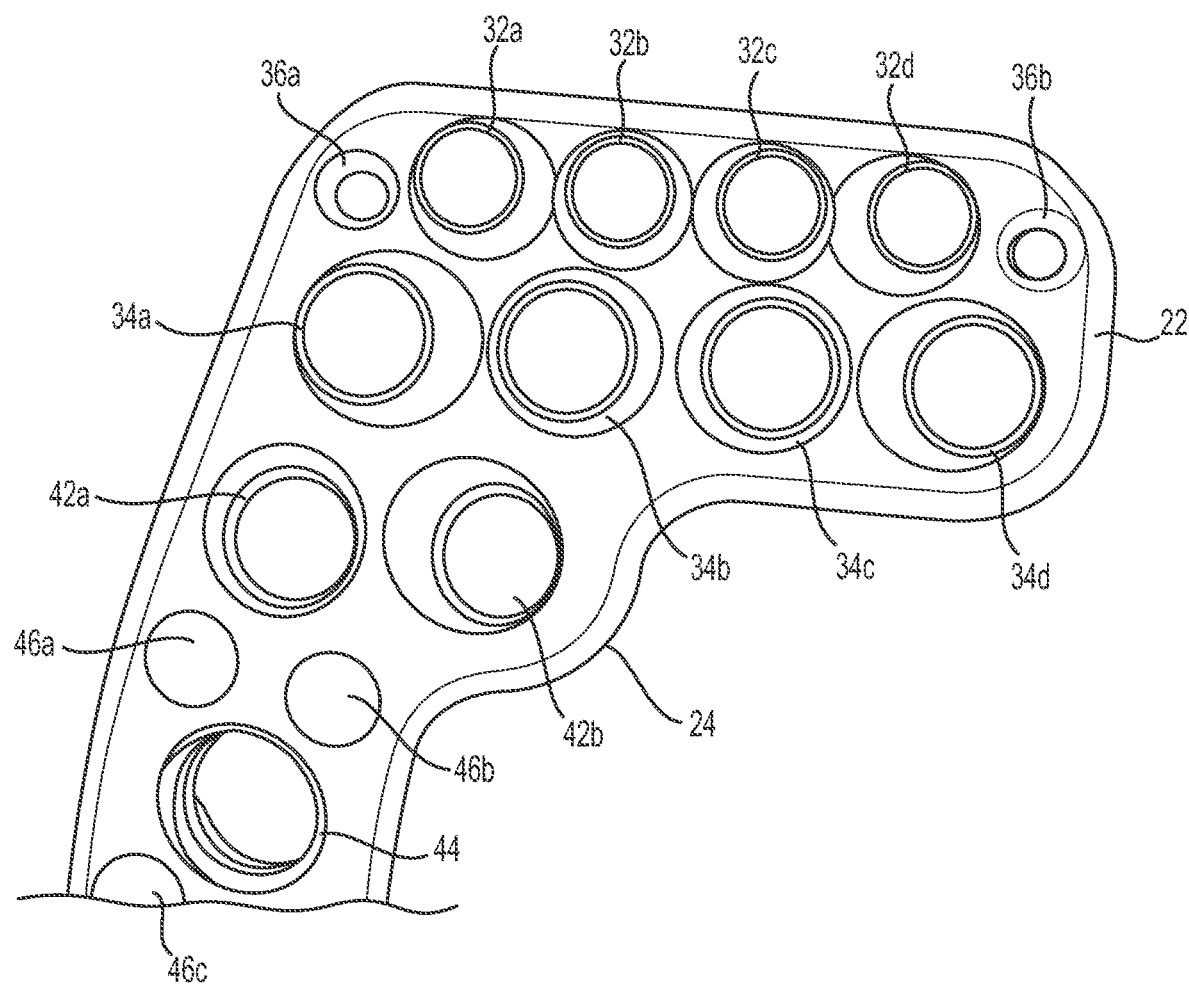
FIG. 2A is a top view of a head of the bone plate of FIG. 1.

FIG. 2A is a top view of a head of the bone plate of FIG. 1. The head portion 22 comprises a widest most portion of the bone plate 10. As shown in FIG. 2A, the head portion 22 accommodates a first row of holes 32a, 32b, 32c, 32d and a second row of holes 34a, 34b, 34c, 34d. As noted above, the first row holes of holes and second row of holes can serve as "rafting" holes to accommodate rafting screws therein. In some embodiments, the first row of holes 32 are smaller than the second row of holes 34. In addition, in some embodiments, the first row of holes 32 are offset from the second row of holes 34. As shown in FIG. 2A, a pair of novel multi-purpose holes 36a, 36b are also provided through the head portion 22 of the bone plate 10. The multi-purpose holes 36a, 36b are each configured to receive a k-wire and/or suture therethrough. Also shown in FIG. 2A are features of the neck portion 24, including the locking holes 42a, 42b, the indentations 46a, 46b, 46c and the instrument attachment hole 44.

Figure 2B:
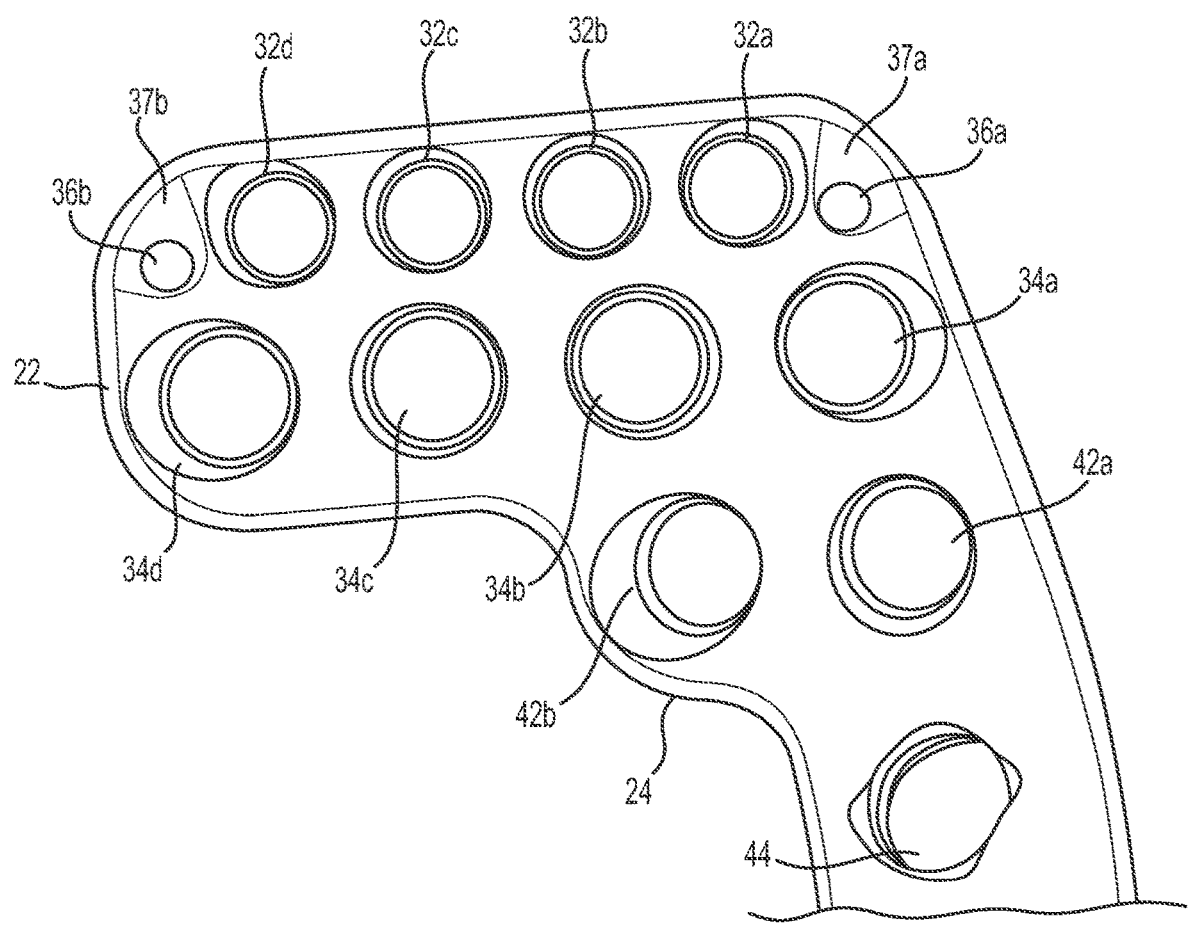
FIG. 2B is a bottom view of a head of the bone plate of FIG. 1.

FIG. 2B is a bottom view of a head of the bone plate of FIG. 1. From the bottom view, one can see the underside of the head portion 22 of the bone plate 10. In particular, one can see the underside of the multi-purpose holes 36a, 36b and how they are formed adjacent and continuously with undercuts 37a, 37b formed on the bone plate 10. As shown in FIG. 5, the undercuts 37a, 37b advantageously allow a suture to be threaded between a bone plate 10 and an underlying bone 2, even when the bone plate 10 is positioned adjacent the bone 2. As shown in FIG. 2B, the undercuts 37a, 37b surround the perimeters of each of the multi-purpose holes 36a, 36b.

Figure 3:
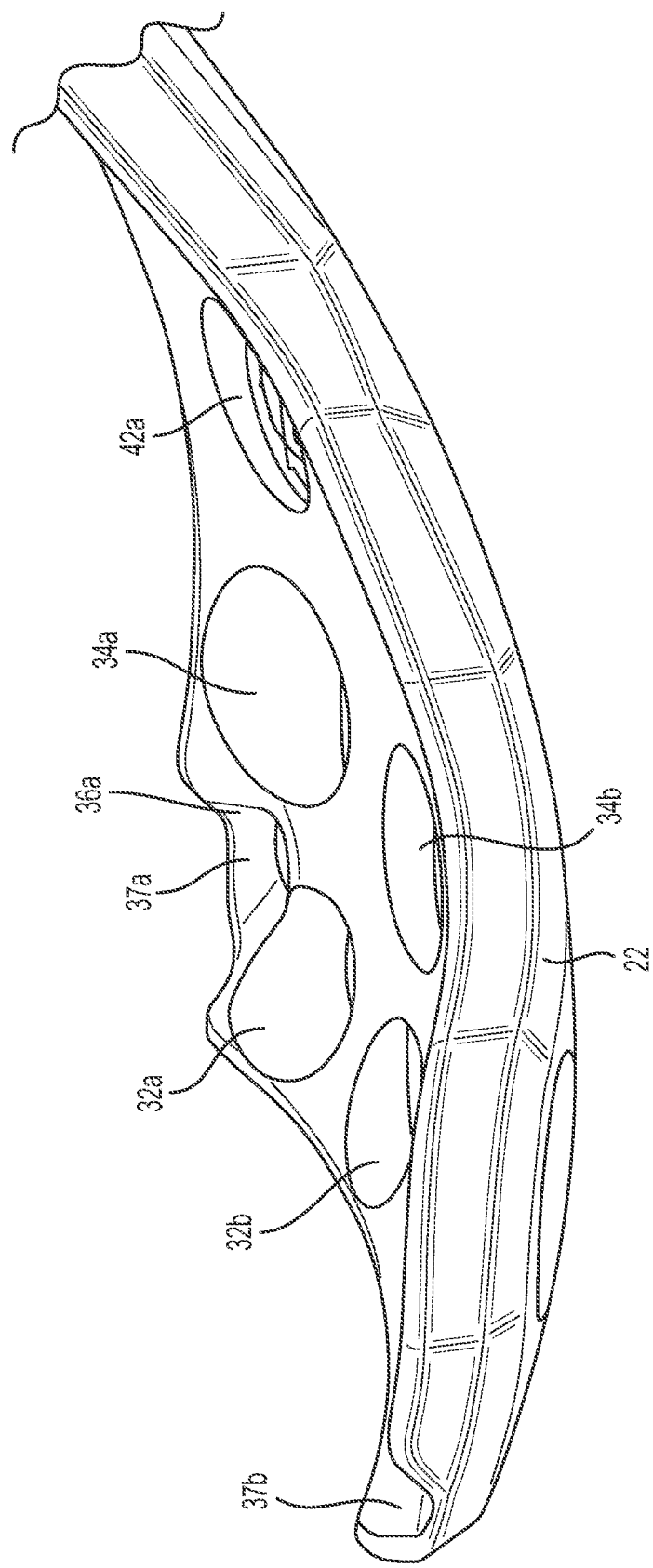
FIG. 3 is a side perspective view of a head of the bone plate of FIG. 1.

FIG. 3 is a side perspective view of a head of the bone plate of FIG. 1. From this view, one can see the curved angle of the head portion 22 of the bone plate 10. In addition, one can see how the undercuts 37a, 37b follow the curved contour of the bone plate 10 and are curved themselves.

FIG. 4 is a view of the bone plate of FIG. 1 attached to a bone. The bone plate 10 includes a plurality of screws or fasteners 6 received therein. Screws 6 that are received in the holes 32a, 32b, 32c, 32d, as well as in the holes 34a, 34b, 34c, 34d, can be considered rafting screws. As shown in FIG. 4, the rafting screws are positioned close to an articular surface 4 of the bone 2 (e.g., tibia) and advantageously help to provide support for the articular surface 4. In other words, the rafting screws help to serve as rebar for the articular surface 4. From this view, one can also see a suture undercut 37a that is formed at a corner of the bone plate 10.

FIG. 5 is an alternative view of the bone plate of FIG. 1 attached to a bone. From this view, one can see how the undercut 37 forms an opening between the bone plate 10 and bone 2 such that there is access to thread a suture even when the bone plate 10 is implanted on bone 2.

FIG. 6 is a top view of a shaft of the bone plate of FIG. 1 with a cross-sectional view shown beneath. The shaft portion 26 includes a number of holes or openings for receiving different bone screws (e.g., locking or non-locking) therein. In some embodiments, the shaft portion 26 can vary in length to accommodate different bones in different sized patients. As shown in FIG. 6, each of the vertical perforated lines represents a possible cutoff or end of a bone plate 10. For patients with smaller bones, the cut-off could be sooner, while for patients with larger bones, the cut-off could be later. In some embodiments, the shaft portion 26 accommodates a unique hole or opening pattern whereby the hole immediate preceding a plate end will be a fixed angle, stacked hole 62. By providing a stacked hole 62 that precedes a plate end, the bone plate 10 can accommodate either a locking or a non-locking screw, thereby providing a large number of options for a surgeon implanting the plate. In some embodiments, the novel pattern of holes or openings in the shaft portion 26 includes holes that are spaced apart (e.g., 12-14 mm) center-to-center and allows plate lengths to be offered in two-hole increments while maintaining that the last hole will always be a stacked hole. In some embodiments, bi-directional compression slots 64 can be worked into the hole pattern, but can appear less than the stacked holes 62 as they may be used less frequently. The unique hole pattern maximizes equidistant locking and non-locking options in the shaft portion 26 while still providing dynamic compression capabilities. In addition, the last hole before the plate end allowing a statically placed locking or non-locking screw is preserved in all two-hole plate increments, as shown in FIG. 6.

Figure 7:
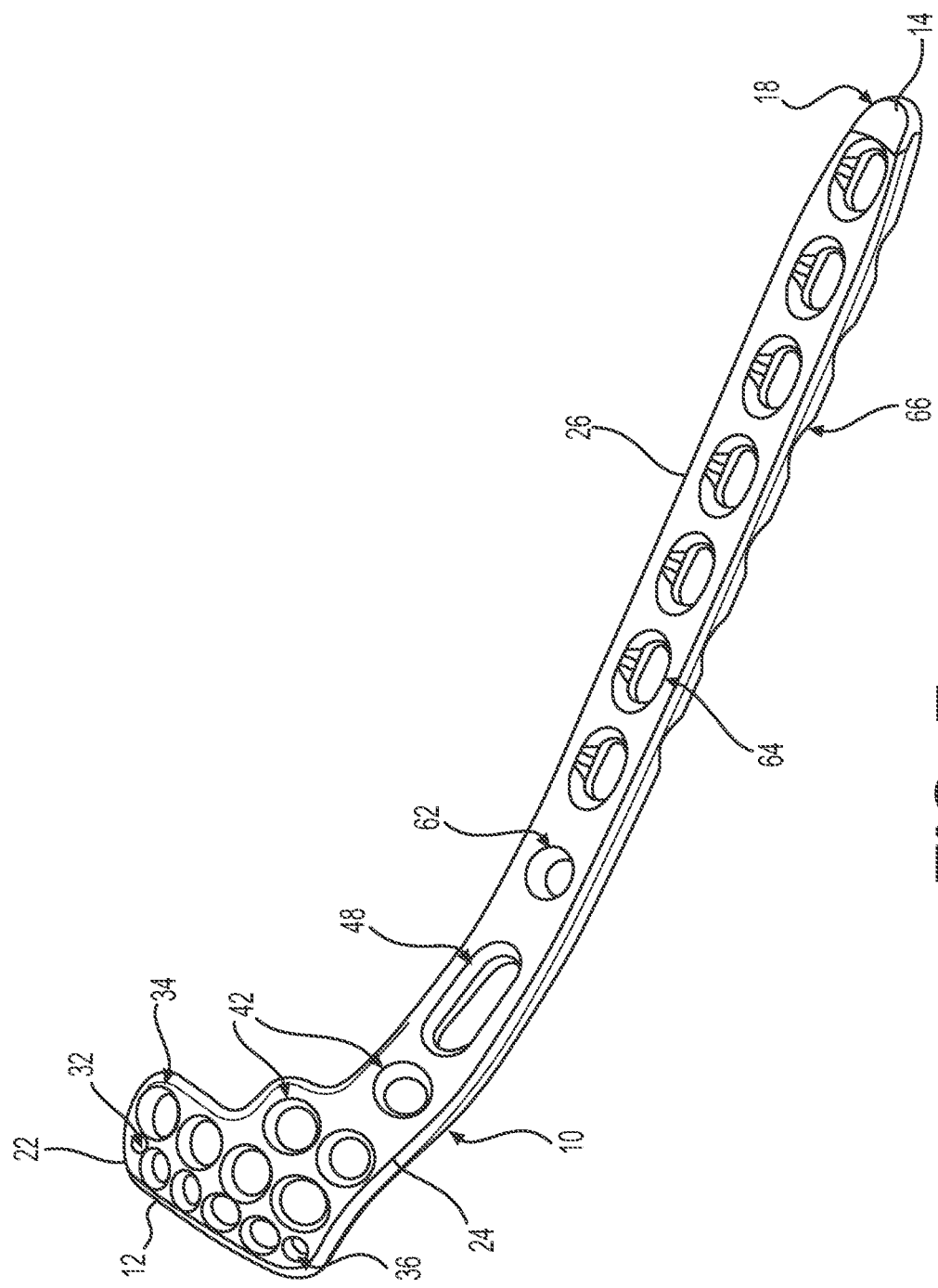
FIG. 7 is a top perspective view of an alternative bone plate in accordance with some embodiments.

FIG. 7 is a top perspective view of an alternative bone plate in accordance with some embodiments. In some embodiments, the bone plate 10 comprises a lateral non-locking plate wherein at least some of holes or openings therein receive non-locking fasteners. The bone plate 10 includes similar features to the bone plate in FIG. 1, including a proximal end 12 and a distal end 14, a head portion 22, a neck portion 24 and a shaft portion 26. The head portion 22 accommodates different sized rafting screws via a first row of rafting holes 32 and a second row of rafting holes 34. The head portion 22 also includes multi-purpose holes 34 capable of receiving a k-wire and/or suture therein. However, the bone plate 10 can include additional non-locking holes for receiving non-locking fasteners, as will be discussed in greater detail herein.

In some embodiments, the neck portion 24 can comprise holes 42 beneath the rafting holes. The holes 42 comprise a trio of non-locking holes capable of receiving non-locking fasteners therein. Beneath the holes 42 comprises an elongated positioning slot 48 for receiving a first bone screw, as discussed above.

In some embodiments, the shaft portion 26 comprises a number of non-locking holes. Shaft portion 26 comprises a non-locking hole 62 for receiving a non-locking fastener. In addition, shaft portion 26 comprises a series of bi-directional dynamic compression slots 64 (which can also be viewed as non-locking openings) for receiving one or more bone fasteners therein. The distal end 14 of the bone plate 10 comprises a tapered tip 18 that aids in insertion of the bone plate 10. An underside of the shaft portion 26 comprises a plurality of scallops 66.

Figure 8:
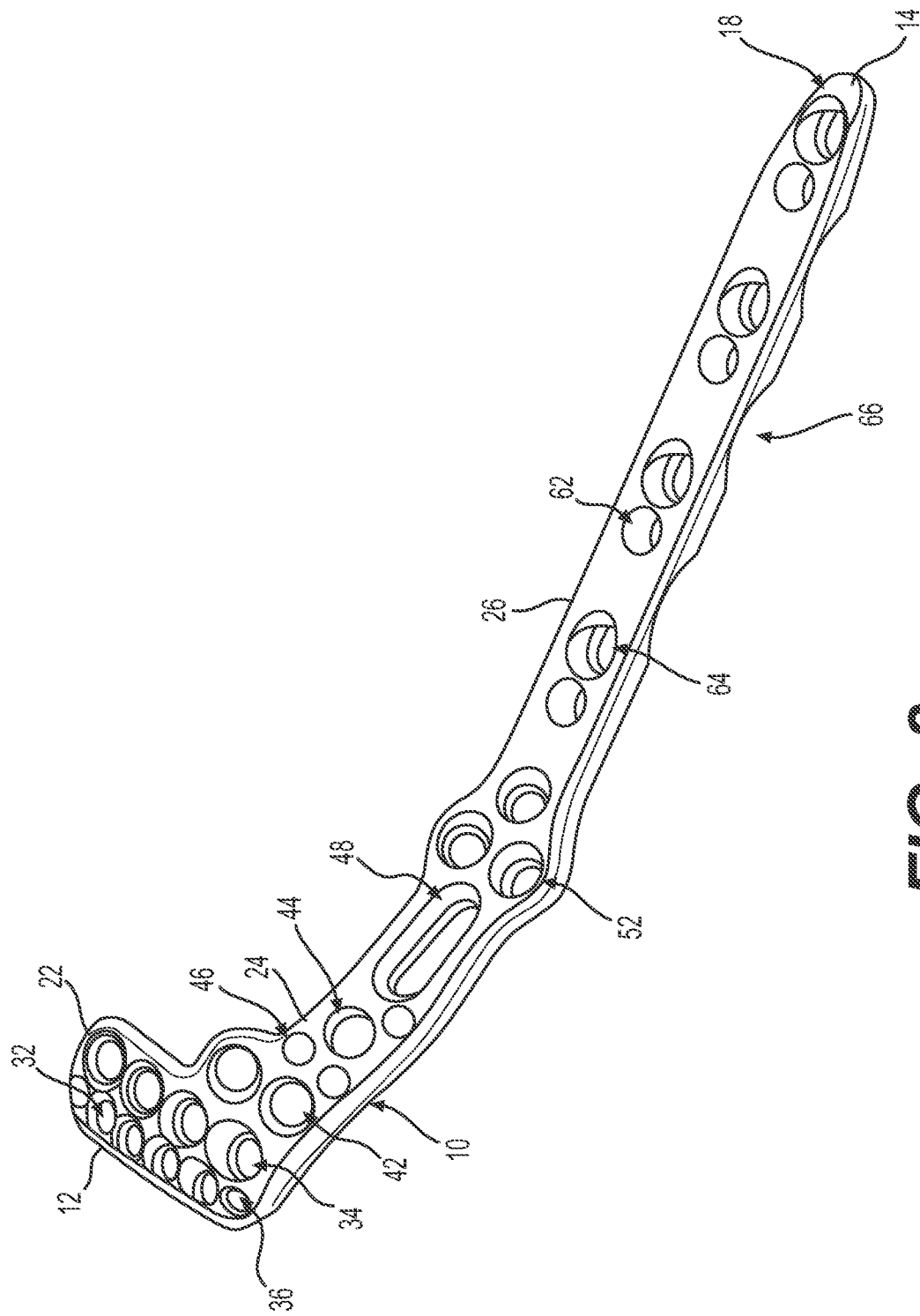
FIG. 8 is a top perspective view of an alternative bone plate in accordance with some embodiments.

FIG. 8 is a top perspective view of an alternative bone plate in accordance with some embodiments. In some embodiments, the bone plate 10 comprises a lateral plate 10 having one or more locking holes for receiving locking fasteners. In some embodiments, the thickness of the lateral bone plate 10 varies from 2.2 mm proximally to 3.4 mm distally, with the thickness transition occurring in the neck of the bone plate 10. The bone plate 10 includes many features as the bone plate in FIG. 1, including a proximal end 12, a distal end 14, a head portion 22, a neck portion 24, and a shaft portion 26. The head portion 22 is the widest portion of the bone plate 10 and includes a pair of rows of rafting holes 32, 34, as well as a pair of multi-functional holes 36 for receiving a k-wire and/or suture therein. The neck portion 24 is also similar to that of the bone plate in FIG. 1, as it includes a pair of polyaxial locking holes 42, a trio of spherical alignment indentations 46, a threaded instrument attachment hole 44, a positioning slot 48 and a trio of kickstand holes 52. However, the shaft portion 26 of the bone plate 10 of FIG. 8 comprises a different pattern of holes as will be discussed herein.

As shown in FIG. 8, the shaft portion 26 comprises a plurality of holes 62, 64. The holes 62 comprise fixed angle locking holes (e.g., 3.5 mm), while the adjacent holes 64 comprise dynamic compression slots. The shaft portion 26 comprises several pairs of fixed angle locking holes 62 adjacent the dynamic compression slots 64, which can be viewed as non-locking.

Figure 9:
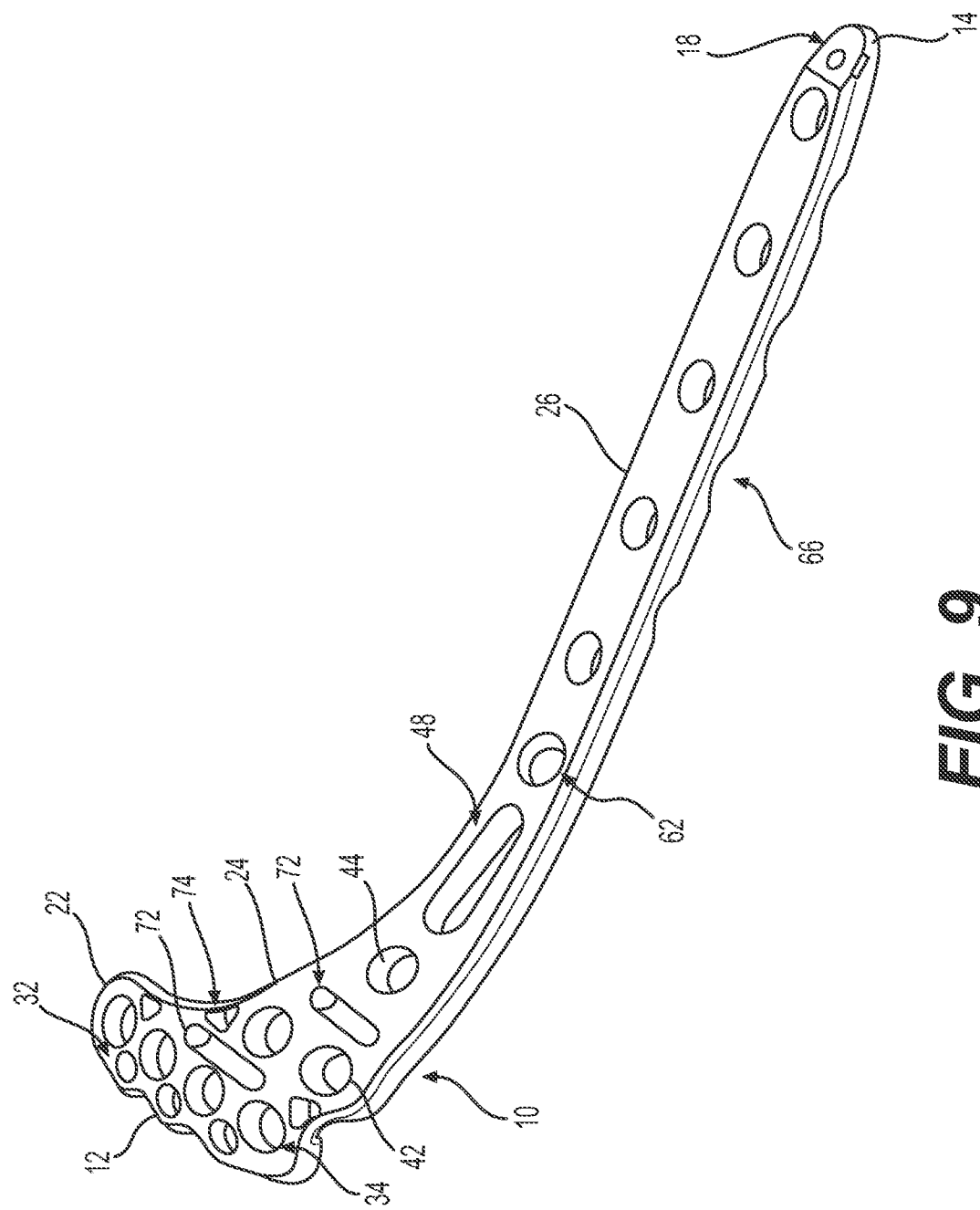
FIG. 9 is a top perspective view of an alternative bone plate in accordance with some embodiments.

FIG. 9 is a top perspective view of an alternative bone plate in accordance with some embodiments. In some embodiments, the bone plate 10 comprises a lateral plate 10 having one or more locking holes for receiving locking fasteners. The bone plate 10 includes many features as the bone plate in FIG. 1, including a proximal end 12, a distal end 14, a head portion 22, a neck portion 24, and a shaft portion 26. The head portion 22 is the widest portion of the bone plate 10 and includes a pair of rows of rafting holes 32, 34. In contrast to the bone plate in FIG. 1, the head portion 22 includes a k-wire recess therein 22 that is separate from a pair of suture holes 74.

The neck portion 24 is also similar to that of the bone plate in FIG. 1, as it includes a pair of polyaxial locking holes 42, a trio of spherical alignment indentations 46, a threaded instrument attachment hole 44, a positioning slot 48 and a trio of kickstand holes 52. However, the shaft portion 26 of the bone plate 10 of FIG. 9 comprises a different pattern of holes as will be discussed herein.

As shown in FIG. 9, the shaft portion 26 comprises a plurality of fixed angle, locking holes 62. Unlike the prior embodiments, there is no compression slot or hole positioned adjacent the locking holes 62. In some embodiments, the fixed angle, locking holes are spaced evenly, while in other embodiments, the fixed angle, locking holes are not spaced evenly. In addition to these locking holes 62, the shaft portion 26 further comprises a tapered tip 18 and a scalloped contact surface.

Figure 10:
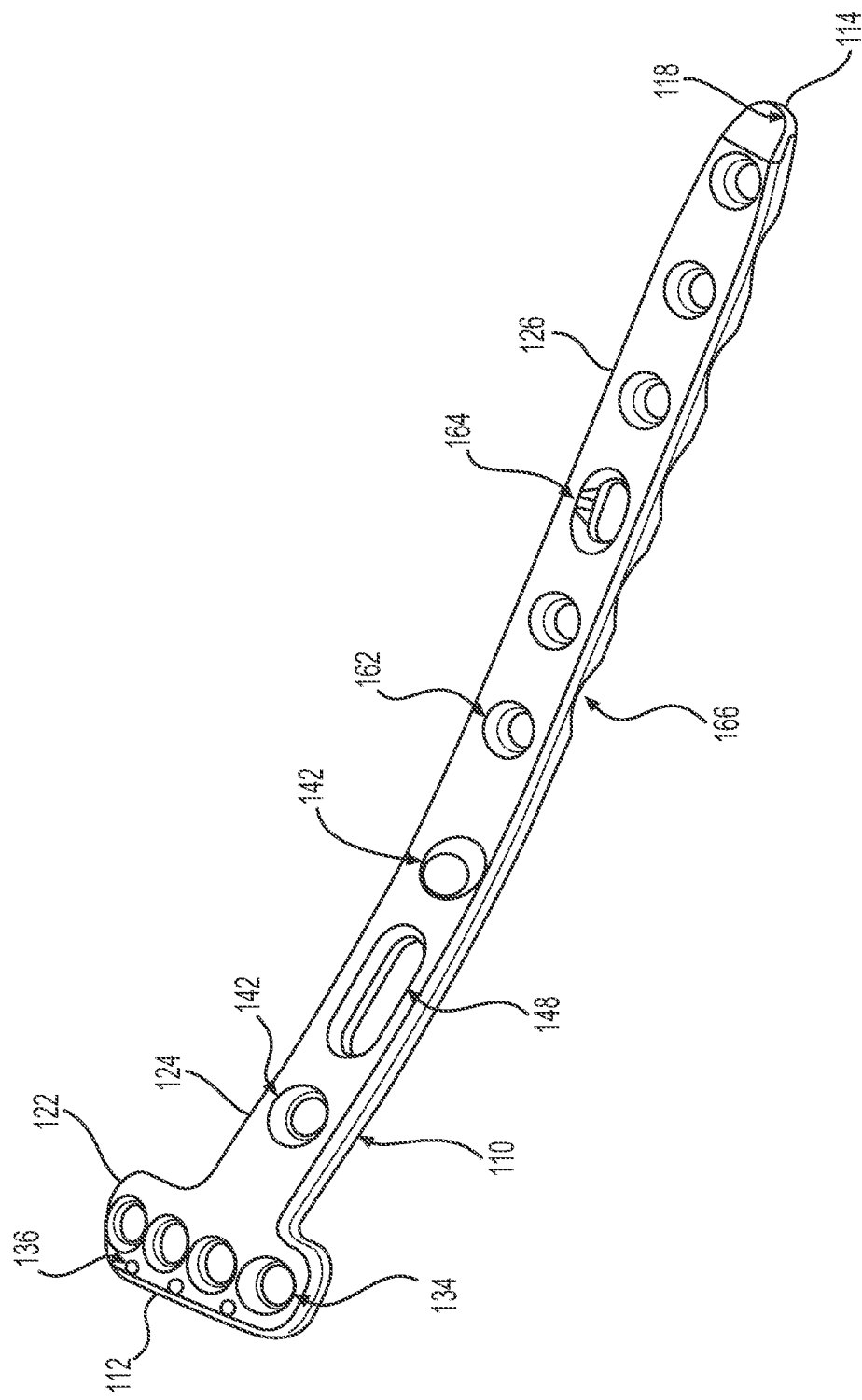
FIG. 10 is a top perspective view of an alternative bone plate in accordance with some embodiments.

FIG. 10 is a top perspective view of an alternative bone plate in accordance with some embodiments. In some embodiments, the bone plate 110 comprises a medial plate which can be placed on a bone (e.g., tibia) via a medial approach. In some embodiments, the thickness of the medial bone plate 110 varies from 2.2 mm proximally to 3.4 mm distally, with the thickness transition occurring in the neck of the bone plate 110. The bone plate 110 comprises a proximal end 112 and a distal end 114. A head portion 122, neck portion 124 and shaft portion 126 extend between the proximal end 112 and distal end 114.

The head portion 122 comprises a widest most portion of the bone plate 110, and includes a series of holes 134 for receiving fasteners therein. In the present embodiment, the holes 134 comprise polyaxial locking holes configured to receive one or more locking fasteners therein. In the present embodiment, the head portion 122 comprises four locking holes 134. In other embodiments, the head portion 122 can comprise one, two, three or more than four locking holes 134. In some embodiments, the holes are between 2.5 mm and 4.5 mm, such as approximately 3.5 mm. The head portion 122 further comprises one or more k-wire openings 136. The k-wire openings 136 (of which three are shown) are positioned near the proximal end 112 of the plate 110 and are configured to receive one or more k-wires therethrough. In some embodiments, the head portion 122 can be sized and configured to extend to an anterior portion of a bone (e.g, a tibia).

The neck portion 124 comprises a pair of holes 142 for receiving one or more fasteners therein. In some embodiments, the holes 142 comprise polyaxial locking holes that are between 2.5 mm and 4.5 mm (e.g., 3.5 mm). In some embodiments, the locking holes are threaded so as to receive one or more threaded locking fasteners. A positioning slot 148 is positioned between the locking holes 142. The positioning slot 148 is an elongated slot (e.g., greater than two times the length of the adjacent holes 142) that is configured to receive a first screw therein.

The shaft portion 126 comprises a plurality of holes 162, as well as a compression slot 164. In some embodiments, the plurality of holes 162 comprise fixed angle, stacked locking holes that are between 2.5 mm and 4.5 mm, such as 3.5 mm. In some embodiments, the compression slot 1645 comprises a bi-directional dynamic compression slot. The shaft portion 126 further comprises a tapered tip 118 that assists the bone plate 110 during insertion. In addition, the shaft portion 126 comprises an underside having one or more scallops 166 forming a scalloped contacting surface.

Figure 11:
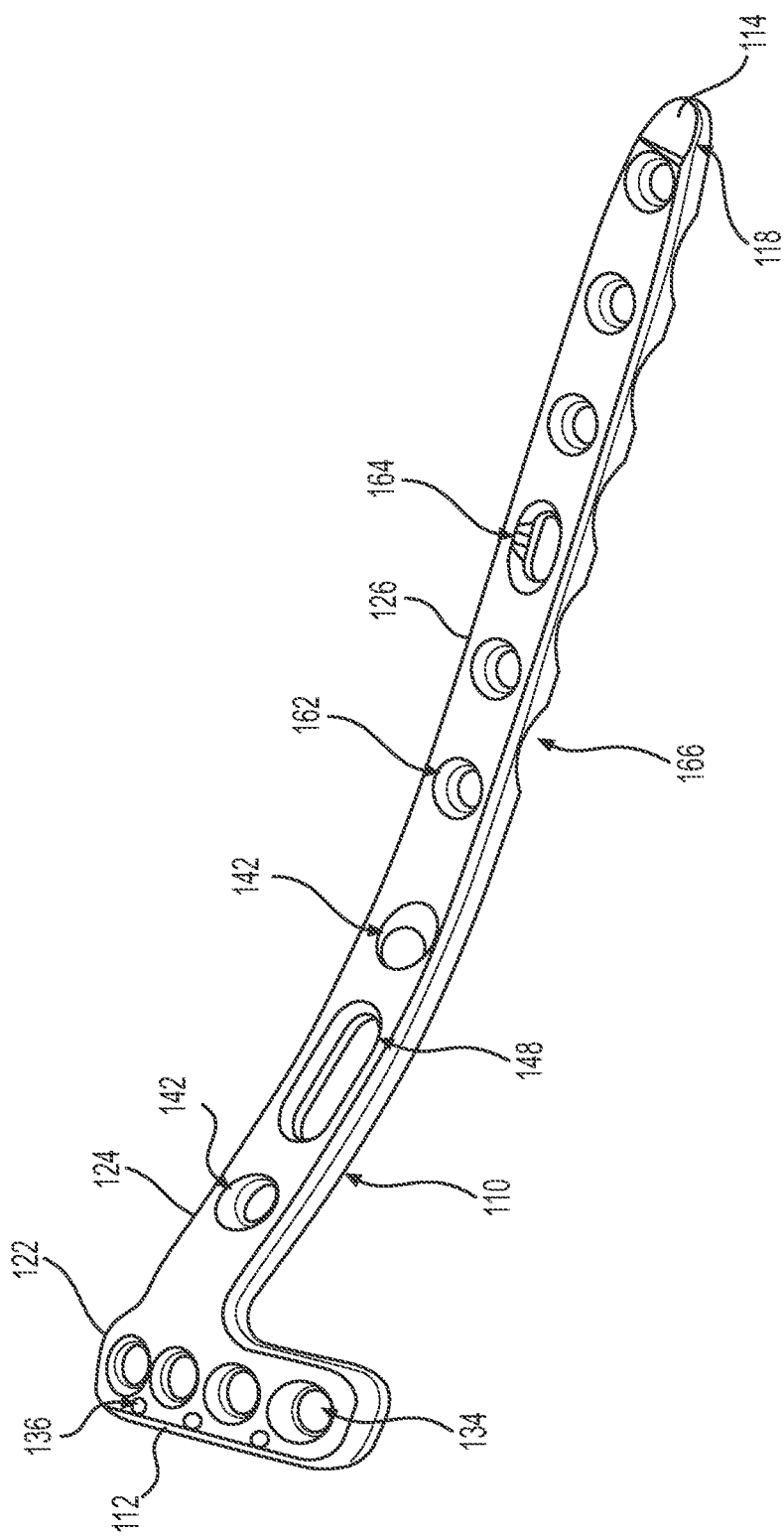
FIG. 11 is a top perspective view of an alternative bone plate in accordance with some embodiments.

FIG. 11 is a top perspective view of an alternative bone plate in accordance with some embodiments. In some embodiments, the bone plate 110 comprises a medial plate. The bone plate 110 is similar to the bone plate in FIG. 10, and includes a proximal end 112, a distal end 114, a head portion 122, a neck portion 124 and a shaft portion 126. However, the shape and size of the head portion 122 is distinguishable. In contrast to the head portion of the bone plate in FIG. 10, which is substantially symmetrical along a longitudinal axis of the bone plate, in FIG. 11, the head portion 122 is offset from a longitudinal axis of the bone plate. In some embodiments, the offset head allows the bone plate 110 to reach a posterior portion of a bone member (e.g., tibia).

Figure 12:
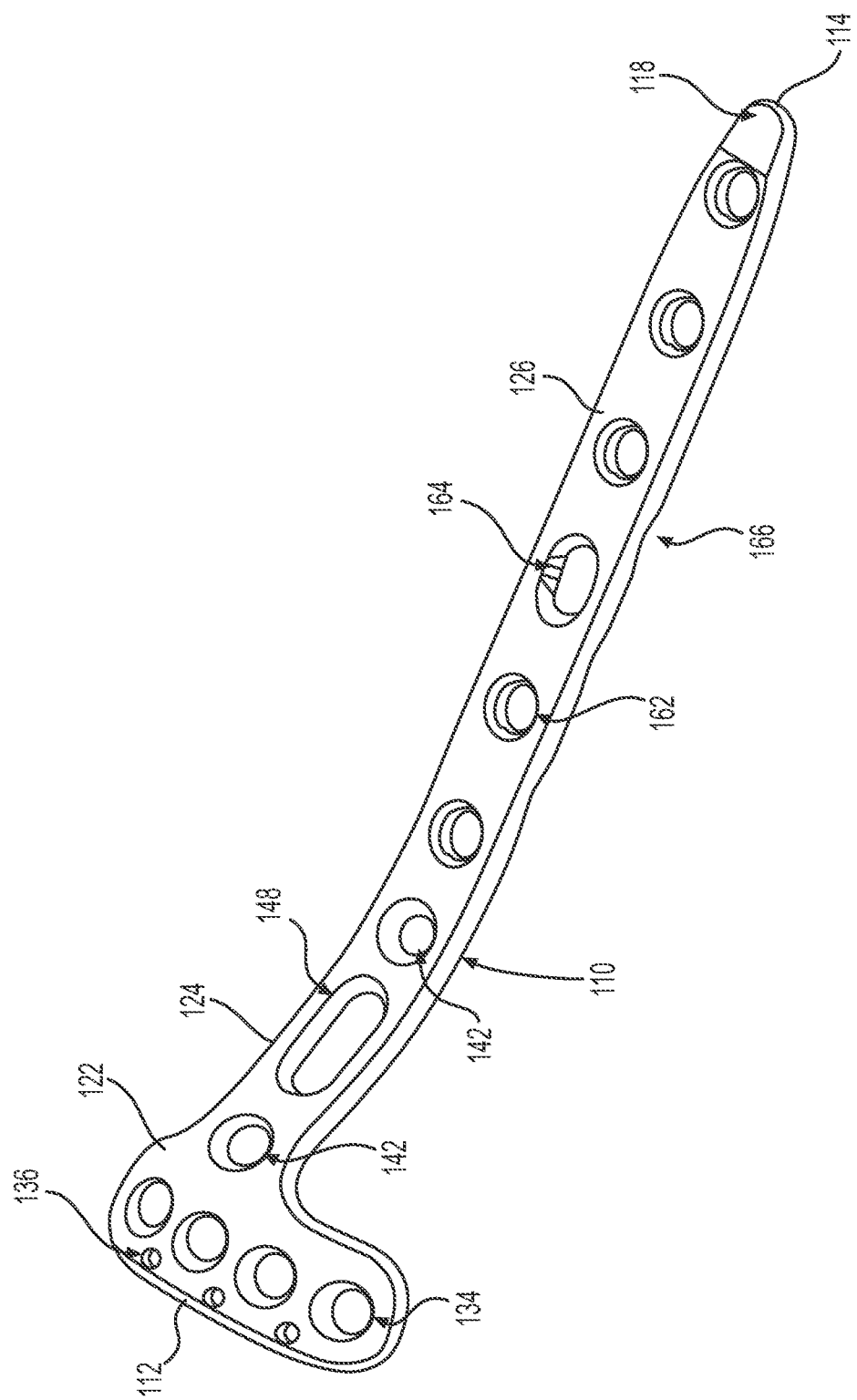
FIG. 12 is a top perspective view of an alternative bone plate in accordance with some embodiments.

FIG. 12 is a top perspective view of an alternative bone plate in accordance with some embodiments. In some embodiments, the bone plate 110 comprises a posteromedial plate that can be inserted through an incision over a posteromedial aspect of a bone (e.g., tibia). The bone plate 110 includes a number of similar features as the medial plates in FIGS. 10 and 11, including a proximal end 112, a distal end 114, a head portion 122, a neck portion 124, and a shaft portion 126. However, in the present embodiment, the bone plate 110 includes several non-locking holes 134 in the head portion 122, as well as several stacked locking holes 162 in the shaft portion 126.

In particular, as shown in FIG. 12, the head portion 122 comprises a row of non-locking holes 134 (e.g., between 2.5 mm and 4.5 mm) that are positioned below a row of k-wire holes. In addition, the head portion 122 comprises a single non-locking hole 142 positioned below the row of non-locking holes 134. The shaft portion 126 comprises a series of fixed angle, stacked locking holes 162 (e.g., between 2.5 mm and 4.5 mm) including a bi-directional dynamic compression slot 164 therebetween.

Figure 13:
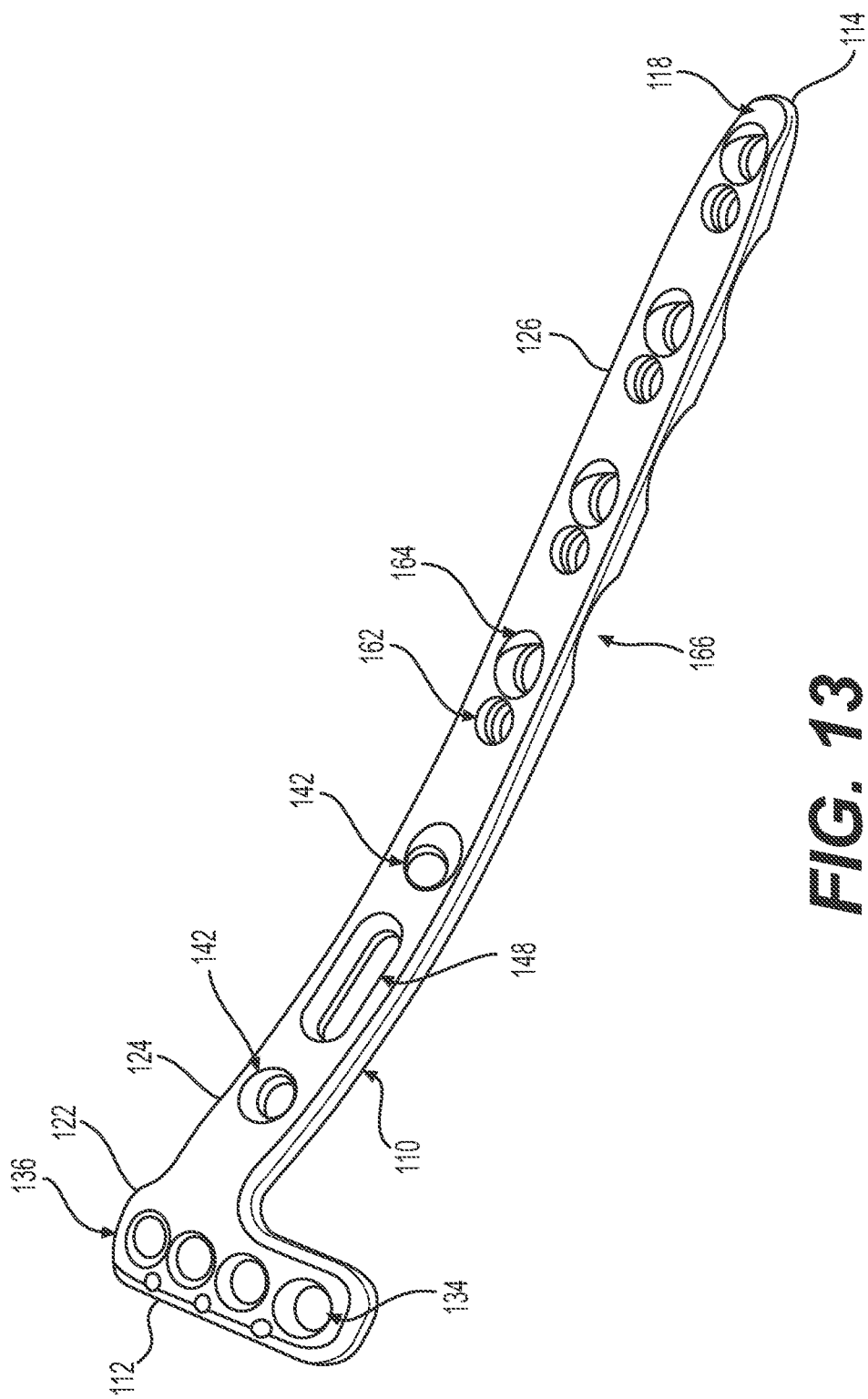
FIG. 13 is a top perspective view of an alternative bone plate in accordance with some embodiments.

FIG. 13 is a top perspective view of an alternative bone plate in accordance with some embodiments. In some embodiments, the bone plate 110 comprises a medial plate that is inserted through an incision over a medial aspect of a bone (e.g., tibia). The bone plate 110 is similar to the bone plate in FIG. 11, but includes a different hole pattern along the shaft portion 126. In the present embodiment, the shaft portion 126 comprises several pairs of holes—a fixed angled locking hole 162 (between 2.5 mm and 4.5 mm) adjacent a dynamic compression slot 164.

Figure 14:
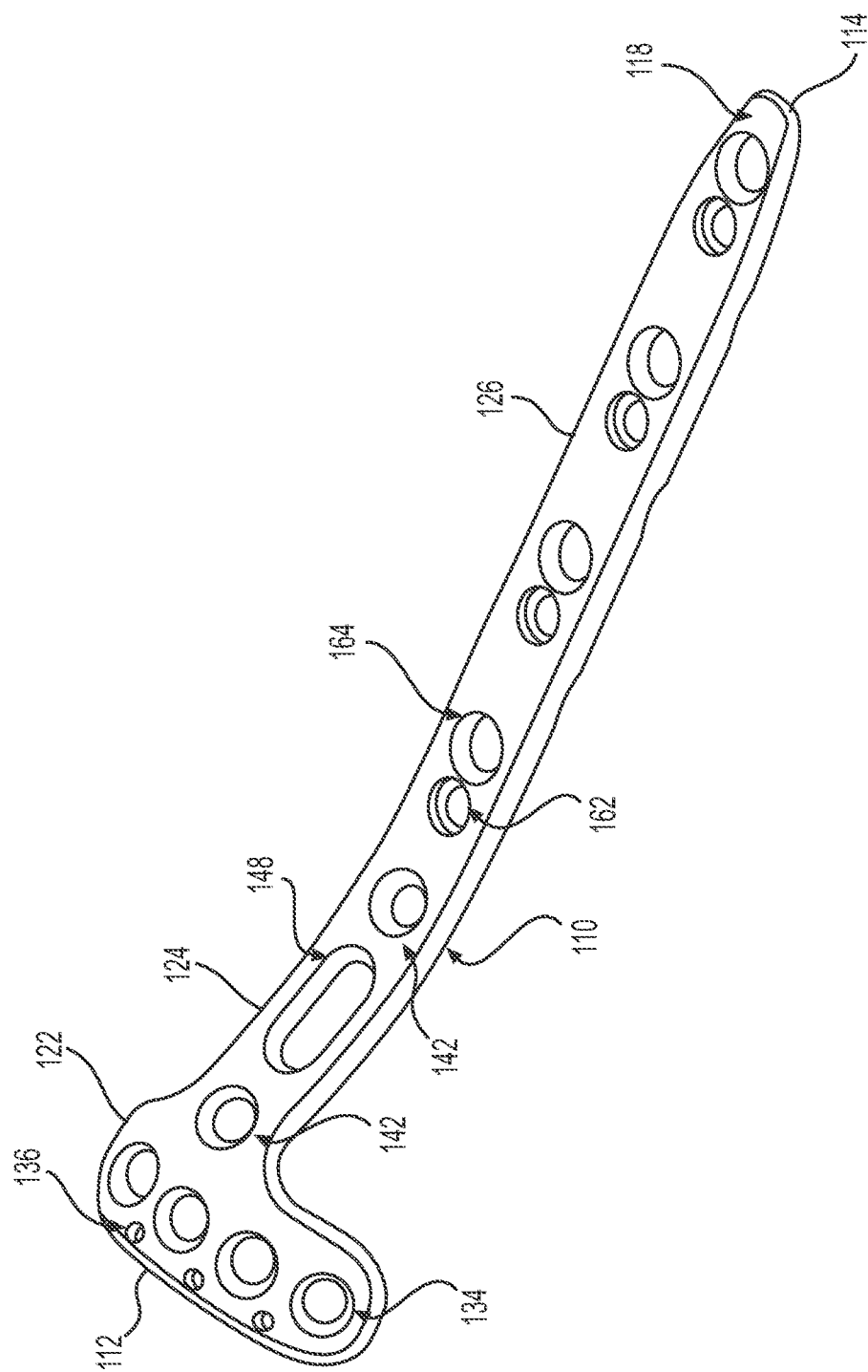
FIG. 14 is a top perspective view of an alternative bone plate in accordance with some embodiments.

FIG. 14 is a top perspective view of an alternative bone plate in accordance with some embodiments. In some embodiments, the bone plate 110 comprises a medial plate that is inserted through an incision over a medial aspect of a bone (e.g., tibia). The bone plate 110 is similar to the bone plate in FIG. 13, except the head portion 122 of the bone plate 110 includes a plurality of non-locking holes 134, 142 (between 2.5 mm and 4.5 mm) rather than locking holes.

Figure 15:
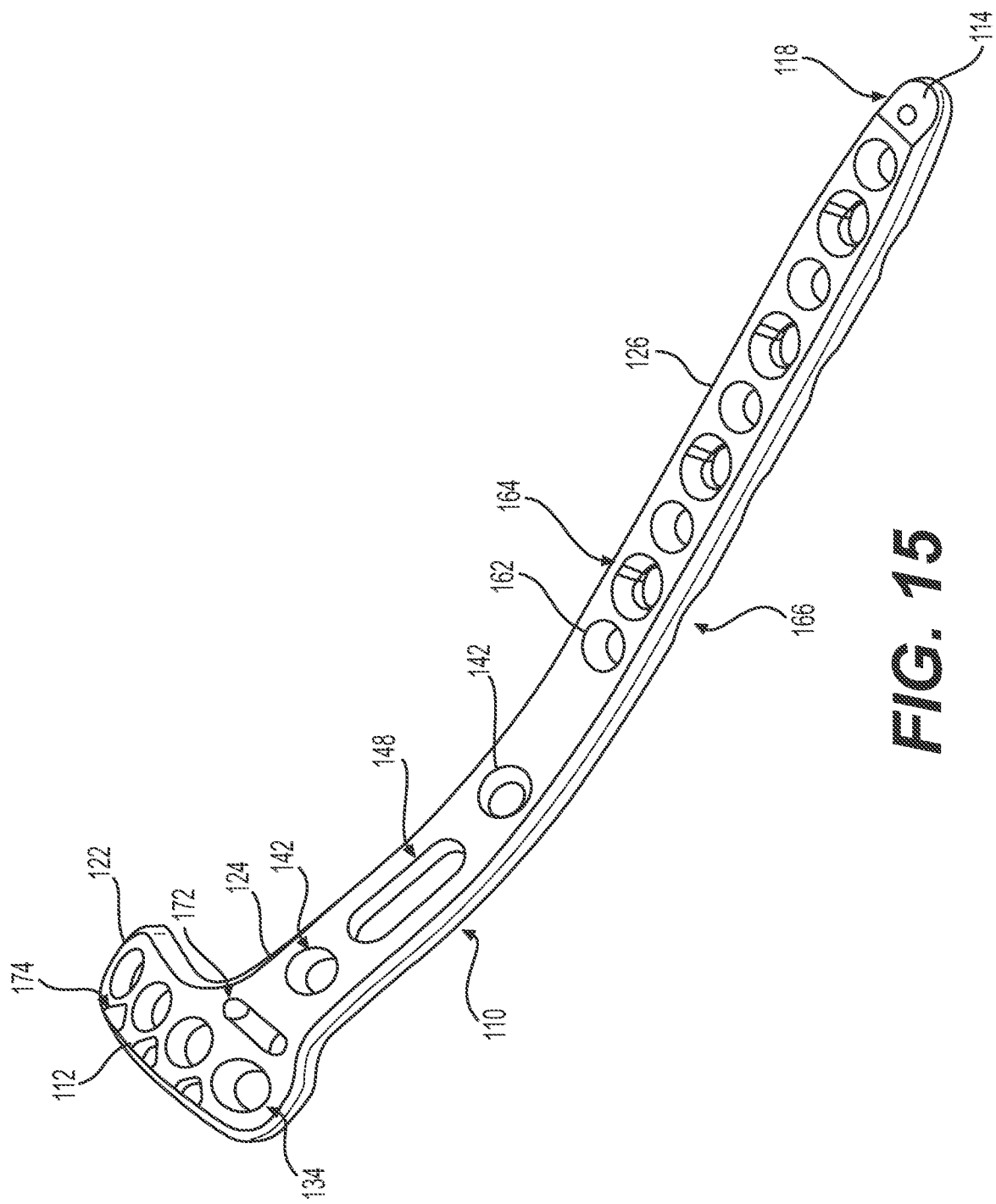
FIG. 15 is a top perspective view of an alternative bone plate in accordance with some embodiments.

FIG. 15 is a top perspective view of an alternative bone plate in accordance with some embodiments. In some embodiments, the bone plate 110 comprises a medial plate that is inserted through an incision over a medial aspect of a bone (e.g., tibia). The bone plate 110 includes a proximal end 112, a distal end 114, a head portion 122, a neck portion 124 and a shaft portion 126. The head portion comprises a row of polyaxial locking holes 134 (between 2.5 mm and 4.5 mm). The locking holes 134 are formed distally beneath suture holes 174. The suture holes 174 are independent from a recess 172 for a k-wire. The head portion 122 also includes a fixed angle locking hole 142 (between 2.5 mm and 4.5 mm). The neck portion 124 comprises a positioning slot 148 and an additional fixed angle locking hole 142. The shaft portion 126 comprises a plurality of alternating locked or unlocked holes 162 and compression slots 164.

Figure 16:
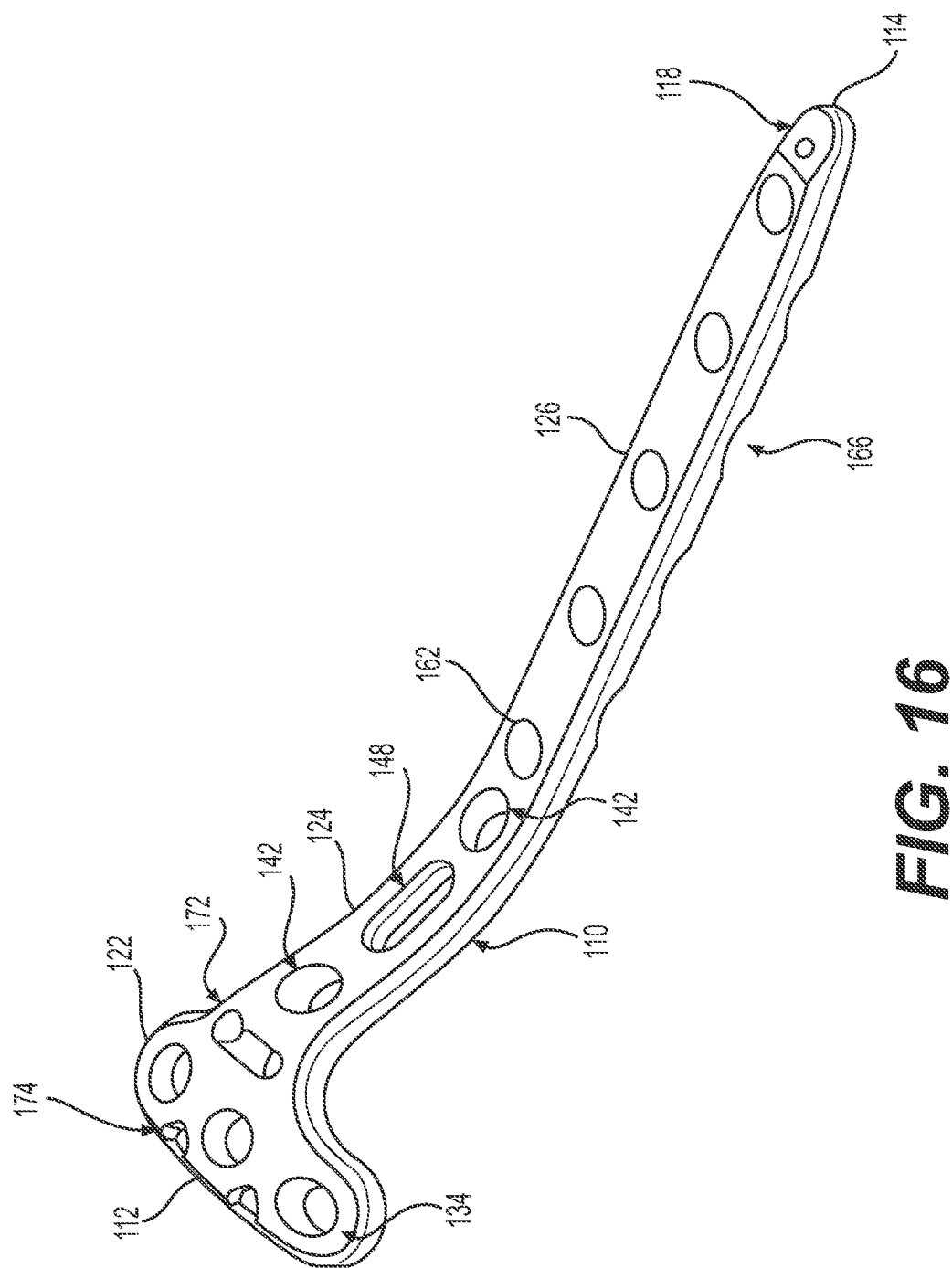
FIG. 16 is a top perspective view of an alternative bone plate in accordance with some embodiments.

FIG. 16 is a top perspective view of an alternative bone plate in accordance with some embodiments. In some embodiments, the bone plate 110 comprises a posteromedial plate that is inserted through an incision over a posteromedial aspect of a bone (e.g., tibia). The bone plate 110 includes similar features as prior embodiments, including a head portion 122 having polyaxial locking holes 134 (between 2.5 mm-4.5 mm), suture holes 174 and a k-wire recess 172. The neck portion 124 includes a pair of fixed angle locking holes 142 (between 2.5 mm and 4.5 mm) and a positioning slot 148 therebetween. The shaft portion 126 comprises a series of in-line openings or holes 162 that can accommodate a locking or non-locking fastener therein.

In some embodiments, an aiming guide can be provided to assist a surgeon in placing one or more screws or fasteners into a patient. The aiming guide can be mounted to a bone plate, and can include guide holes that align with holes in the bone plate such that screws or fasteners can be accurately implanted into a patient. In some embodiments, the guide holes can accept aiming sleeves that interface with drill guides, trocars, k-wires and screws. These sleeves can be secured to the aiming guide by a ratcheting or clipping mechanism. While the aiming guide can be particularly useful for lateral plates, the aiming guide can also be used for medial and posteromedial plates.

Figure 17:
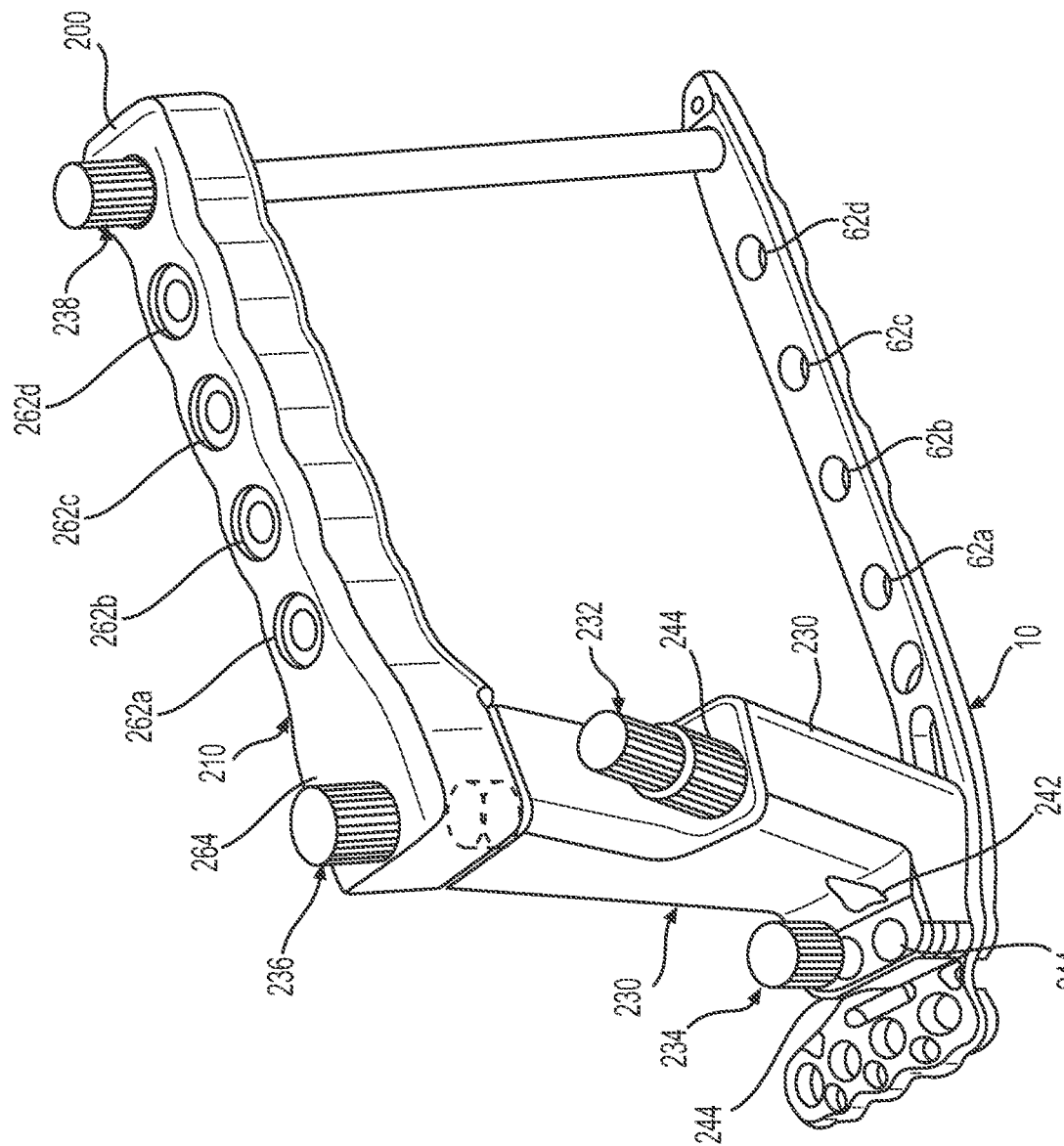
FIG. 17 is a top perspective view of an aiming guide in accordance with some embodiments.

FIG. 17 is a top perspective view of an aiming guide in accordance with some embodiments. The aiming guide 200 can be mounted to an underlying plate 10, and includes an aiming arm 210 and an aiming mount 230.

The aiming arm 210 comprises a plurality of guide holes 262a, 262b, 262c, 262d that correspond with holes 62a, 62b, 62c, 62d of the plate 10. The purpose of the guide holes 262 is to help guide one or more fasteners or screws into the corresponding holes 62 with precision and accuracy. In some embodiments, the guide holes 262 can receive aiming sleeves that interface with drill guides, trocars, k-wires or screws. The aiming arm 210 includes an opening 264 on one end for receiving an arm fixation bolt 236 therein and an opening 266 on the opposing end for receiving a distal locking bolt 238 therein. The arm fixation bolt 236 is configured to extend and secure the aiming arm 210 to the aiming mount 230. The distal locking bolt 238 is configured to engage an opening near a distal end of a bone plate 10, thereby providing a stable construct. In some embodiments, the aiming arm 210 is formed of a non-metal, such as a carbon fiber. By forming the aiming arm 210 of a non-metal, this advantageously prevents it from being visible on an x-ray.

The aiming mount 230, which is attached to the aiming arm 210, serves as a mount on the plate 10. The aiming mount 230 (shown in FIGS. 18 and 19) comprises an upright post portion including a pair of openings 244 for receiving an anti-rotation bolt 234 therein and an opening 244 for receiving a fixation bolt 232 therein. The fixation bolt 232 serves to attach the aiming mount 230 (and thus the entire aiming guide 200) to a plate 10. The fixation bolt 232 can be received in an attachment hole 44 (shown in FIG. 1) of the plate 10. The anti-rotation bolt 234 can be inserted into either of the mono-axial openings 244 to provide additional rigidity during insertion. In some embodiments, the aiming mount 230 can be a different material from aiming arm 210, as the aiming mount 230 does not obstruct viewing of the holes 62 in the plate 10. In some embodiments, the aiming mount 230 can be formed of metal while the aiming arm 210 can be formed of non-metal. The means of connecting the aiming arm 210 to the aiming mount 230 will not be described in more detail.

FIG. 18 is a side view of a mount of the aiming guide of FIG. 17. The aiming mount 230 comprises an upright post having an upper section and a lower section. The upper section comprises a plurality of openings 235 (shown in FIG. 19) for receiving stabilizing pins 240 therein. The aiming arm 210 attaches to the aiming mount 230 by sliding over the stabilizing pins 240 and tightening the arm fixation bolt 236. The arm fixation bolt 236 is received in a threaded mounting hole 237 (shown in FIG. 19) that is formed on the upper section of the aiming mount 230.

The aiming mount 230 further comprises a lower section including openings 244 for receiving one or more anti-rotation bolts 234 (shown in FIG. 17). The one or more anti-rotation bolts 234 provide additional rigidity to the aiming mount 230. The lower section includes another opening 231 through which the fixation bolt 232 (shown in FIG. 17) extends therethrough. The lower section can further include a positioning feature 239 that guides and orients the aiming mount 230 into a proper position relative to the underlying bone plate 10.

Figure 19:
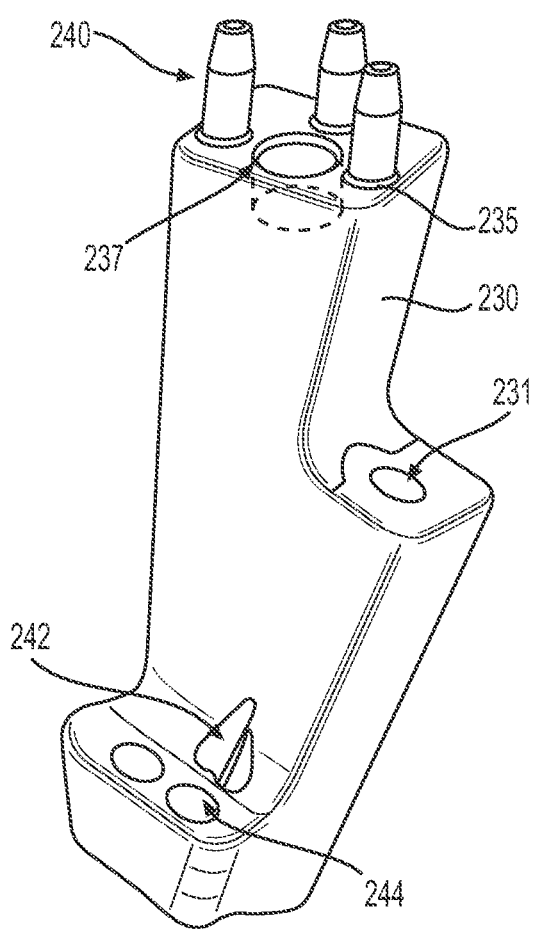
FIG. 19 is an alternative side view of a mount of the aiming guide of FIG. 17.

FIG. 19 is an alternative side view of a mount of the aiming guide of FIG. 17. From this view, one can see specific features of the upper section and lower section of the aiming mount 230. In particular, in the upper section, one can see the plurality of openings 235 for receiving stabilizing pins 240 therein. In addition, one can see the threaded mounting hole 237 that receives the arm fixation bolt 236 to secure the aiming arm 210 to the aiming mount 230. Between the upper section and the lower section of the aiming mount 230 is an opening 231 for receiving the fixation bolt 232 therein. From this view, one can see the openings 244 in the lower section for receiving one or more anti-rotation bolts 234 therein.

Figure 20:
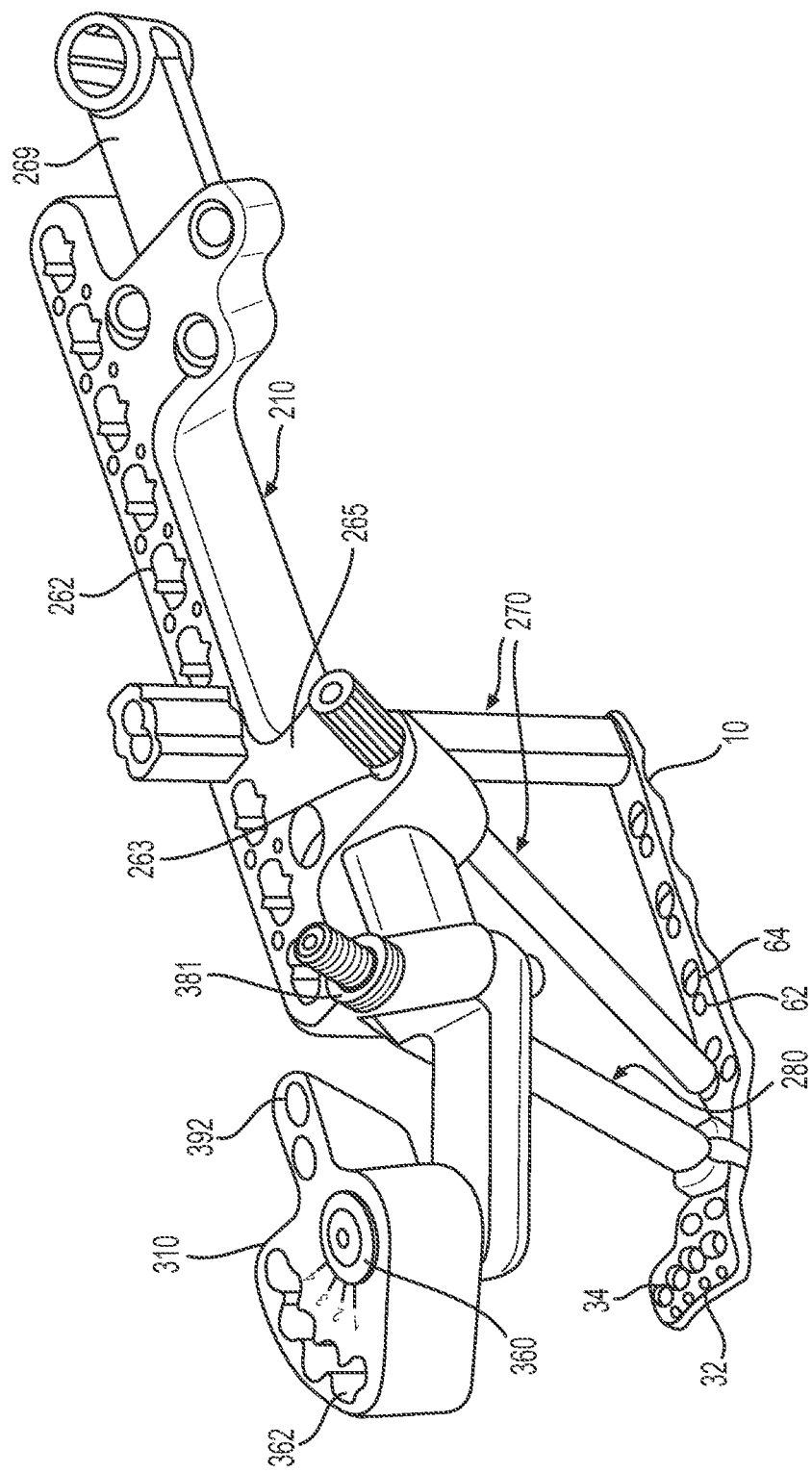
FIG. 20 is a top perspective view of an aiming guide comprising a distal aiming guide and an optional proximal aiming guide in accordance with some embodiments.

FIG. 20 is a top perspective view of an aiming guide comprising a distal aiming guide and an optional proximal aiming guide in accordance with some embodiments. The distal aiming guide 210 is capable of guiding one or more fasteners or screws into distal openings or holes (such as holes or slots 62, 64) of the bone plate 10, while the proximal aiming guide 310 is capable of guiding one or more fasteners or screws into proximal openings or holes (such as rafting holes 32, 34) of the bone plate 10. In some embodiments, both the distal and proximal aiming guides 210, 310 are capable of accepting one or more aiming sleeves that interface with drill guides, trocars, k-wires, and screws. These sleeves can be secured to the respective guide by a ratcheting or clipping mechanism.

The distal aiming guide 210 comprises an arm including a plurality of guide holes 262 formed therein. The plurality of guide holes 262 are sized and configured to receive one or more aiming sleeves 270 that interface with drill guides, trocars, k-wires and screws. In some embodiments, the one or more aiming sleeves 270 help guide screws into holes or slots 62, 64. The arm includes an extension portion 263 that includes one or more additional guide holes 265 for receiving one or more aiming sleeves 270 therein. The one or more sleeves 270 received in the one or more guide holes 265 can be used to direct screws or fasteners into one or kickstand holes of the bone plate 10. The distal aiming guide 210 further comprises at least one opening for receiving an attachment post 280 therethrough. The attachment post 280 is configured to attach to the bone plate 10.

Figure 23:
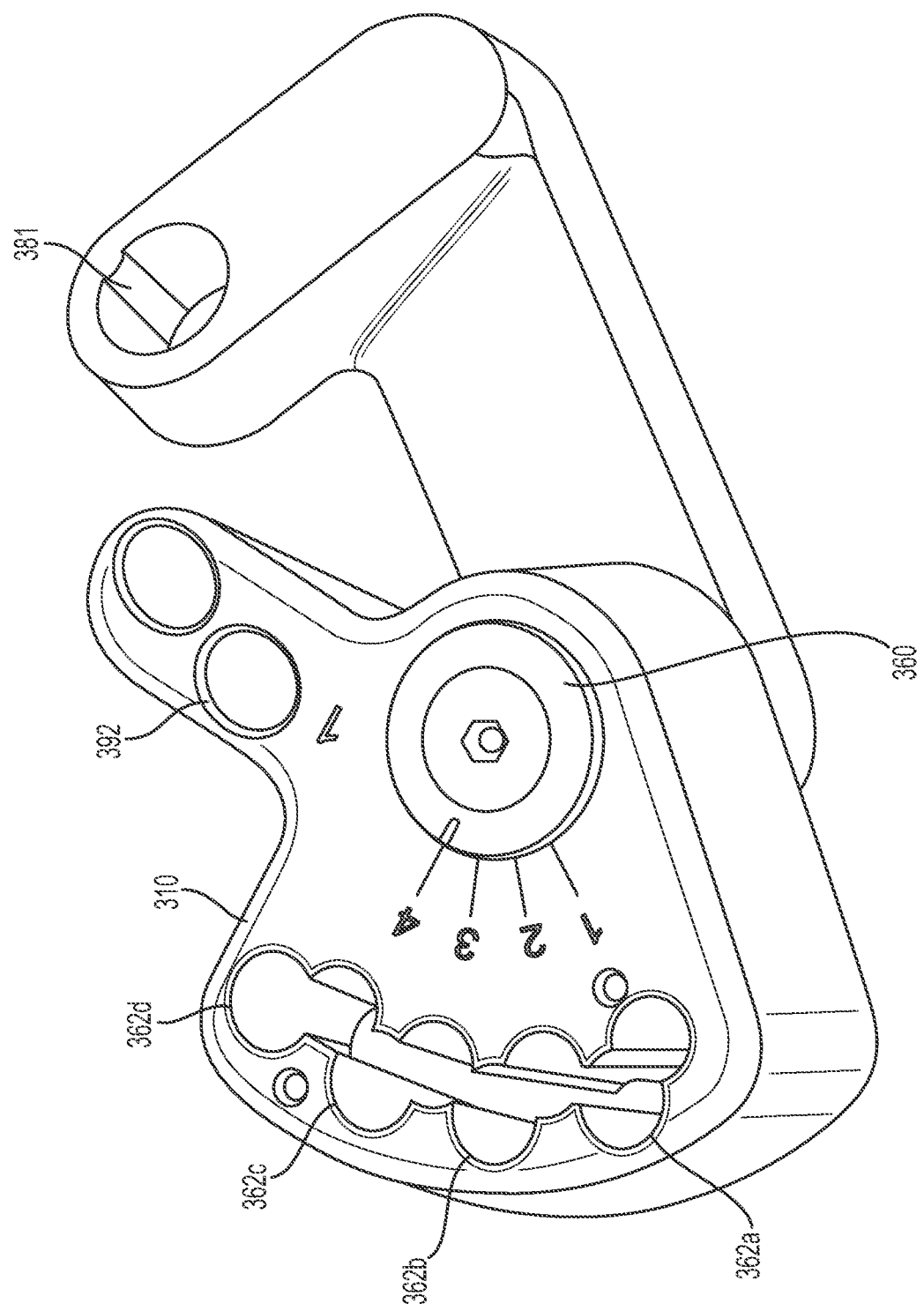
FIG. 23 is a top perspective view of the proximal aiming guide of FIG. 20.

The proximal aiming guide 310 comprises one or more guide holes 362 that can be used to direct screws or fasteners into the rafting holes 32, 34 of the bone plate 10. In the proximal aiming guide 310, each of the guide holes 362 is formed of a pair of overlapping openings or circles. For example, as shown in FIG. 23, guide hole 362a is formed of a pair of overlapping openings or circles, as are guide holes 362b, 362c, 362d. By providing a pair of overlapping openings or circles, each of the guides holes 362a, 362b, 362c, 362d can effectively guide one or more fasteners or screws into a rafting hole in a first row or a second row, based on surgeon preference. For example, as shown in FIGS. 25A-25D, guide hole 362a will guide a screw into rafting hole 32a, guide hole 362b will guide a screw into rafting hole 32b, guide hole 362c will guide a screw into rafting hole 32c, and guide hole 362d will guide a screw into rafting hole 32d. In some embodiments, the dial 360 of the proximal aiming guide 310 can assume four different positions at 20 degrees apart for targeting holes in the underlying plate 10 that are coaxial with the holes 362 in the guide. In some embodiments, the proximal aiming guide 310 can rotate out of the way to allow for easier visualization of the plate 10.

In some embodiments, the proximal aiming guide 310 comprises a dial 360 that indicates which of the guide holes 362a, 362b, 362c, 362d will be available for use. In some embodiments, only a single guide hole 362a, 362b, 362c, 362d will be available in each setting, thereby reducing the risk of confusion to a surgeon. The dial is rotatable and has a setting that corresponds with each of the guide holes 362, 362b, 362c, 362d.

FIG. 21 is a top perspective view of the distal aiming guide of FIG. 20. As shown in the figure, the distal aiming guide 210 comprises an arm having a plurality of guide holes 262 extending along a length of the arm. The guide holes 262 correspond to one or more holes or slots in the bone plate 10, thereby allowing a screw to be easily guided into a proper position on the plate. In some embodiments, the guide holes 262 are coaxial with holes or slots in the bone plate 10. In some embodiments, the guide holes 262 accept a guide (e.g., a sleeve) in different positions to target non-locking plate holes in either a static or eccentric position. This facilitates percutaneous insertion of non-locking screws either statically or for dynamic compression. In some embodiments, the distal aiming guide 210 includes guide holes 262 that correspond with holes or slots in the shaft portion 26 of the bone plate 10, as well as guide holes 265 that correspond with kickstand holes in the neck portion 24. In some embodiments, the guide holes 262 that correspond with holes or slots in the shaft portion 26 accepts only one type of aiming sleeve 270, while the guides holes 265 that correspond with the kickstand holes in the neck portion 26 accept another type of aiming sleeve 270. In some embodiments, the distal aiming guide 210 can be formed of a radiolucent material to prevent obstruction of fluoroscopic imaging while in an operating room.

The distal aiming guide 210 includes a pair of attachment arms 267, 269. The first attachment arm 267 comprises a first connection 281a and the second connection arm 269 comprises a second connection 281b. Each of these connections 281a, 281b is capable of attachment to an optional proximal aiming guide 310. By providing two connections 281a, 281b, the distal aiming guide 210 is advantageously reversible such that it is can be acceptably used via left hand or right hand.

Figure 22:
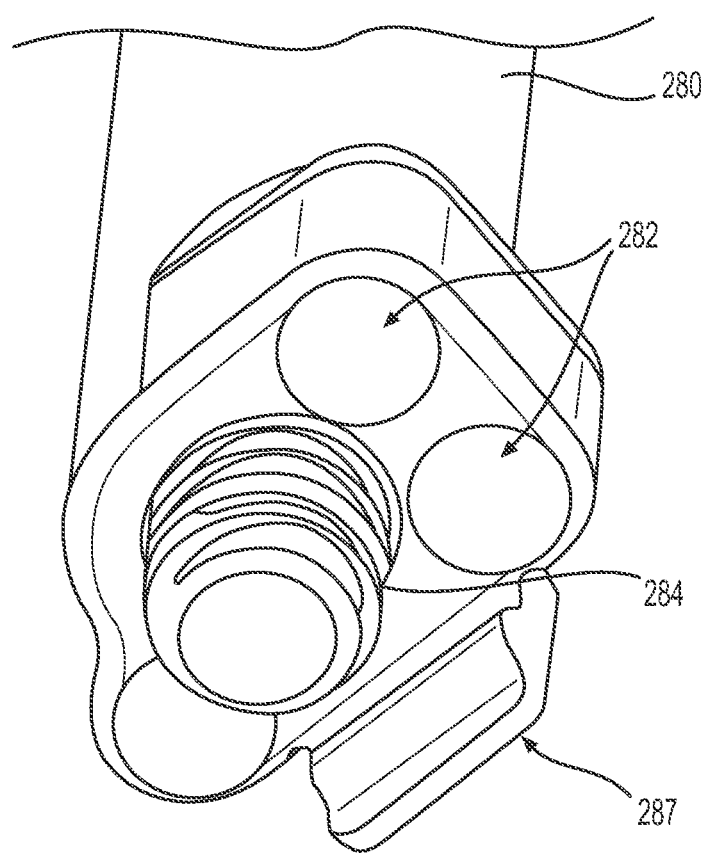
FIG. 22 is a bottom perspective view of an attachment post in accordance with some embodiments.

FIG. 22 is a bottom perspective view of an attachment post in accordance with some embodiments. The attachment post 280 is insertable through a connection opening 381 in the proximal aiming guide 310 (shown in FIG. 20), as well as through a connection 281 (shown in FIG. 21) in the distal aiming guide 210 (shown in FIG. 21). The attachment post 280 is configured to engage an underlying bone plate 10. The attachment post 280 comprises one or more ball-end pins 282 for engaging alignment indentations 44 (shown in FIG. 1) of the bone plate 10. In addition, the attachment post 280 comprises a threaded shaft 284 for threadingly attaching to an instrument attachment hole 44 in the bone plate 10. The attachment post 280 further comprises a stabilizing feature 287 that assists with alignment during attachment.

FIG. 23 is a top perspective view of the proximal aiming guide of FIG. 20. From this view, one can see the guide holes 362a, 362b, 362c, 362d, as well as the dial 360 that determines which of the guide holes 362a, 362b, 362c, 362d is available for use. In addition, FIG. 23 shows neighboring guide holes 392 through which one or more additional aiming sleeves can be inserted. In addition, a connection opening 381 is shown through which an attachment post 280 can be received therein. In some embodiments, the connection opening 381 in the proximal aiming guide 310 is coaxial with a connection 281 in the distal aiming guide 210, such that the attachment post 280 can extend through both the proximal aiming guide 310 and the distal aiming guide 210.

Figure 24:
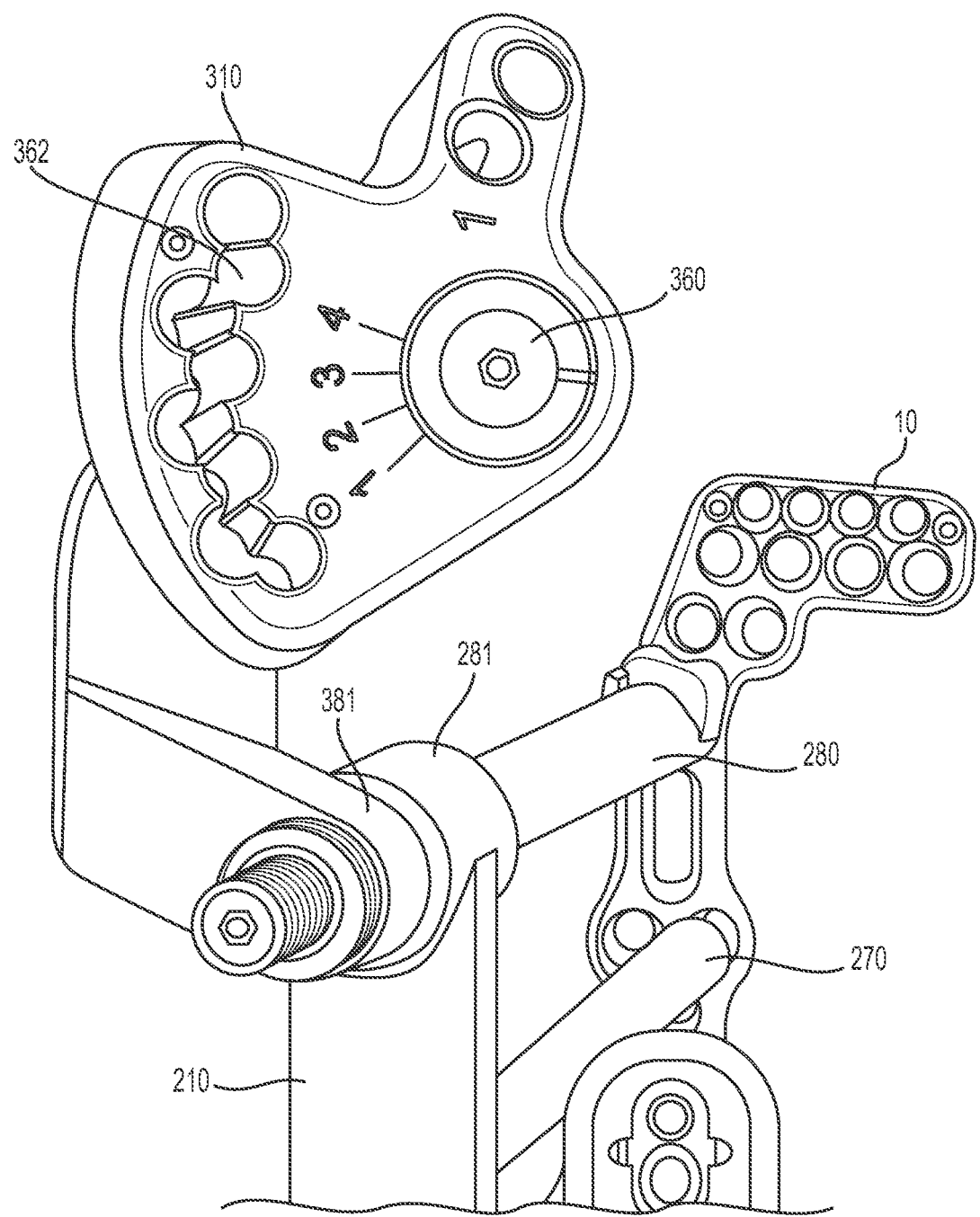
FIG. 24 is a top perspective view of the distal aiming guide with optional proximal aiming guide of FIG. 20.

FIG. 24 is a top perspective view of the distal aiming guide with proximal aiming guide of FIG. 20. From this view, one can see how the attachment post 280 extends through the connection opening 381 of the proximal aiming guide 310 and into the connection 281 in the distal aiming guide 210 before engaging the bone plate 10. The attachment post 280 advantageously serves as a means to secure the distal aiming guide 210 with the proximal aiming guide 310.

Figure 25A:
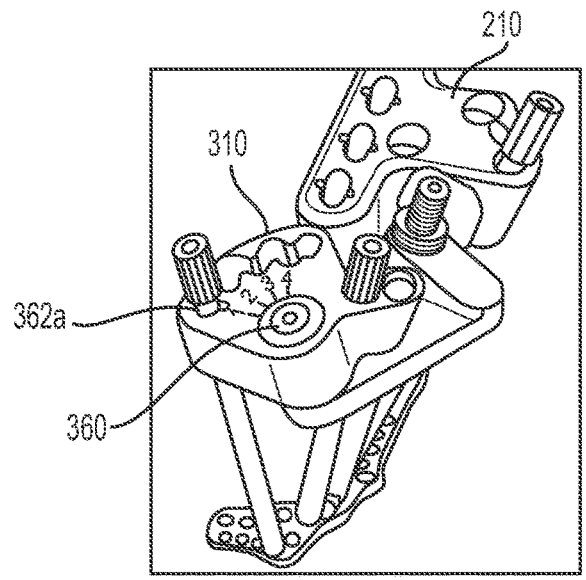
FIG. 25A is a view of the distal aiming guide with proximal aiming guide in a first setting.

FIG. 25A is a view of the distal aiming guide with proximal aiming guide in a first setting. In this first setting of the dial 360, the aiming sleeve 270 is capable of being inserted into guide hole 362a.

Figure 25B:
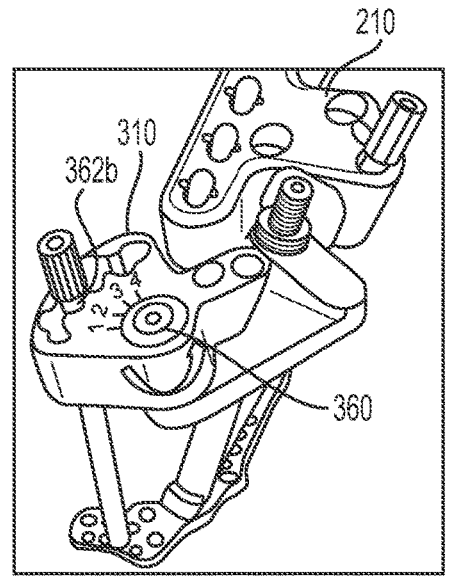
FIG. 25B is a view of the distal aiming guide with proximal aiming guide in a second setting.

FIG. 25B is a view of the distal aiming guide with proximal aiming guide in a second setting. In this second setting of the dial 360, the aiming sleeve 270 is capable of being inserted into guide hole 362b.

Figure 25C:
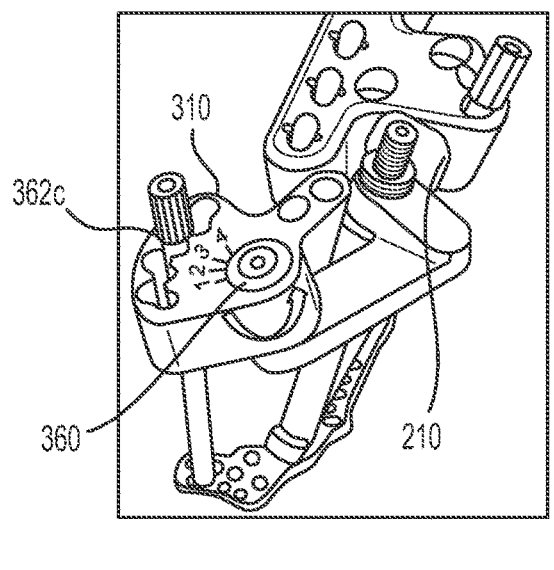
FIG. 25C is a view of the distal aiming guide with proximal aiming guide in a third setting.

FIG. 25C is a view of the distal aiming guide with proximal aiming guide in a third setting. In this third setting of the dial 360, the aiming sleeve 270 is capable of being inserted into guide hole 362c.

Figure 25D:
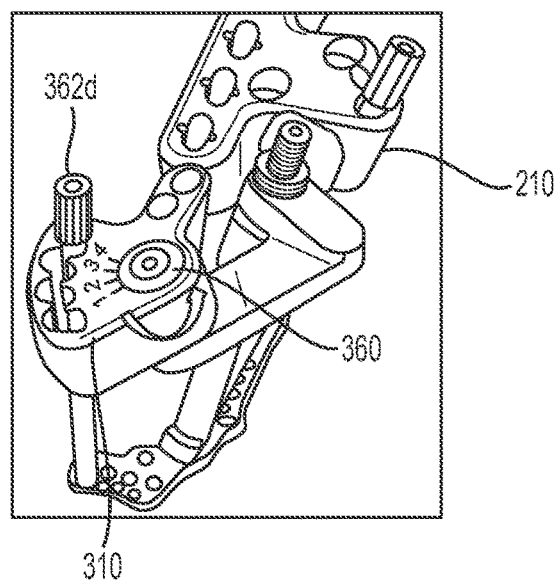
FIG. 25D is a view of the distal aiming guide with proximal aiming guide in a fourth setting.

FIG. 25D is a view of the distal aiming guide with proximal aiming guide in a fourth setting. In this fourth setting of the dial 360, the aiming sleeve 270 is capable of being inserted into guide hole 362d.

Figure 27:
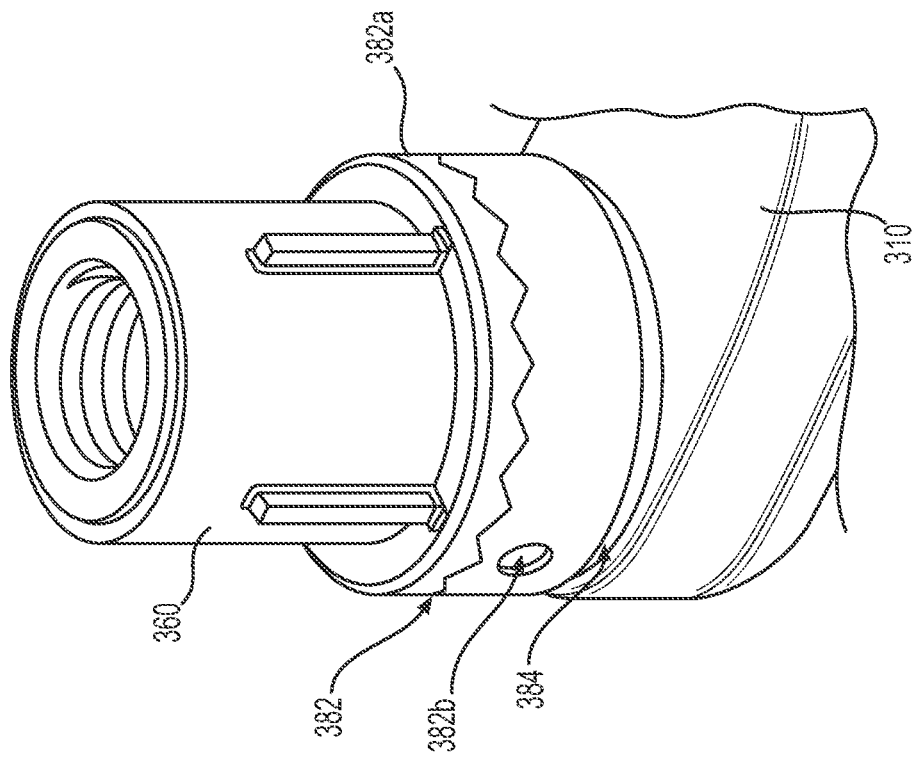
FIG. 27 is a top perspective view of dial in the proximal aiming guide.
Figure 26:
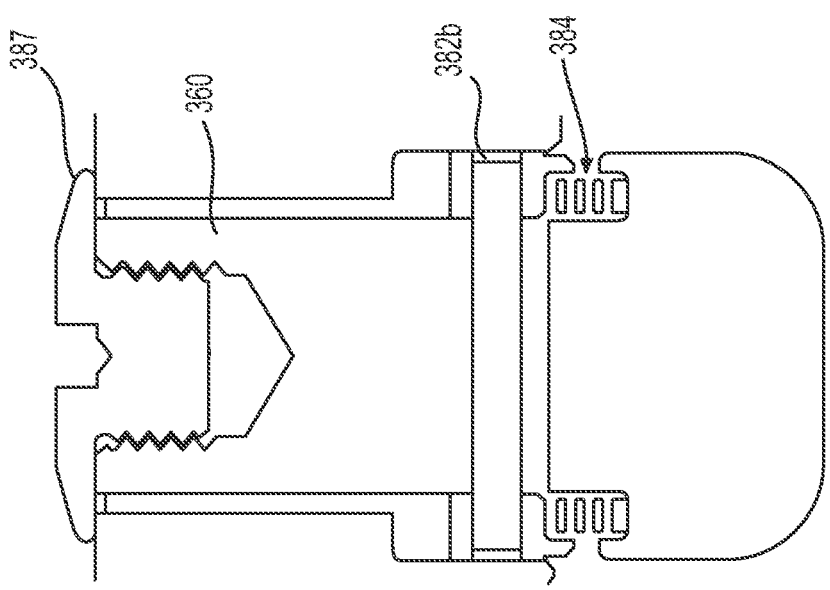
FIG. 26 is a cross-sectional view of a dial in the proximal aiming guide.

FIG. 26 is a cross-sectional view of a dial in the proximal aiming guide. FIG. 27 is a top perspective view of dial in the proximal aiming guide. The dial 360 comprises a rotating mechanism that uses a variation of a Hirth coupling 382 and a spring 384 that accommodates different settings. As the dial 360 is rotated by hand, the top coupling 382a of the Hirth coupling 382 exerts a force on the bottom coupling 382b causing it to translate axially along a shaft. Once clearance is achieved, the dial 360 will complete its designed rotation (e.g., 20 degrees) with a click. The retention cap 387 holds the dial 360 in place axially along the shaft and counteracts the force of the spring 384 which forces the bottom coupling 382b to translate down with the rotation.

As noted above, embodiments of the bone plates can include one or more rows of rafting openings or holes for receiving rafting screws therein. These rafting screws can be provided at or near an articular joint of a bone, thereby reducing the risk of subsidence at the articular joint. More details regarding the rafting screws, as well the optional use of non-threaded rafting blades, are provided below.

Figure 46:
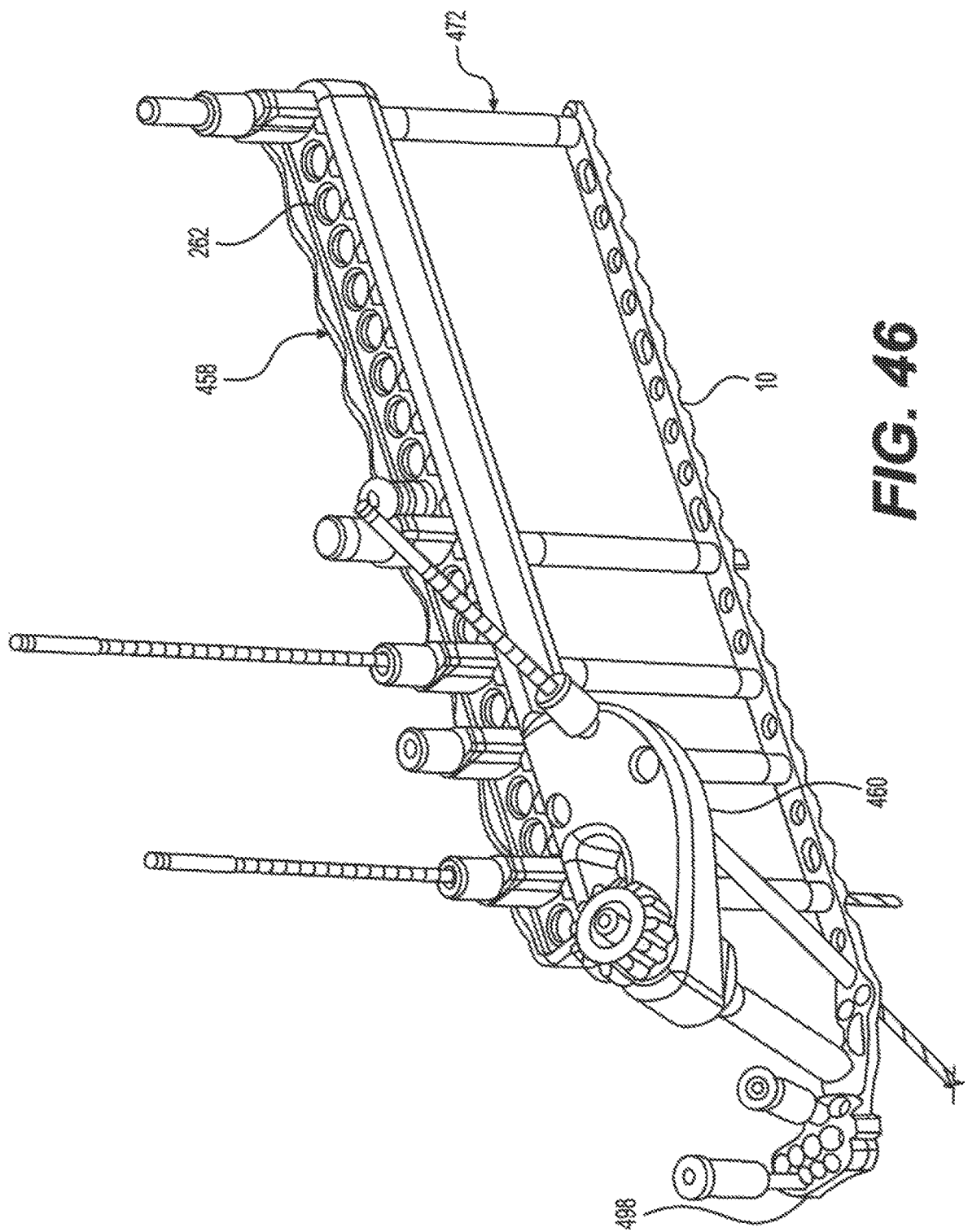
FIG. 46 is a diagram showing an alternate embodiment of an aiming guide according to one embodiment of the present invention.

FIG. 46 is a diagram showing an alternate embodiment of an aiming guide according to one embodiment of the present invention. In the illustrated embodiment, the aiming guide 452 may be operatively connected to an underlying plate 10, and includes an attachment post 454 and a threaded shaft 456. The aiming guide 452 illustrated in FIG. 46 and its individual components are similar to the aiming guide 200 described with respect to FIGS. 17-22 above, with some modifications. The modifications to the aiming guide 200 will be described in turn below.

Figure 47:
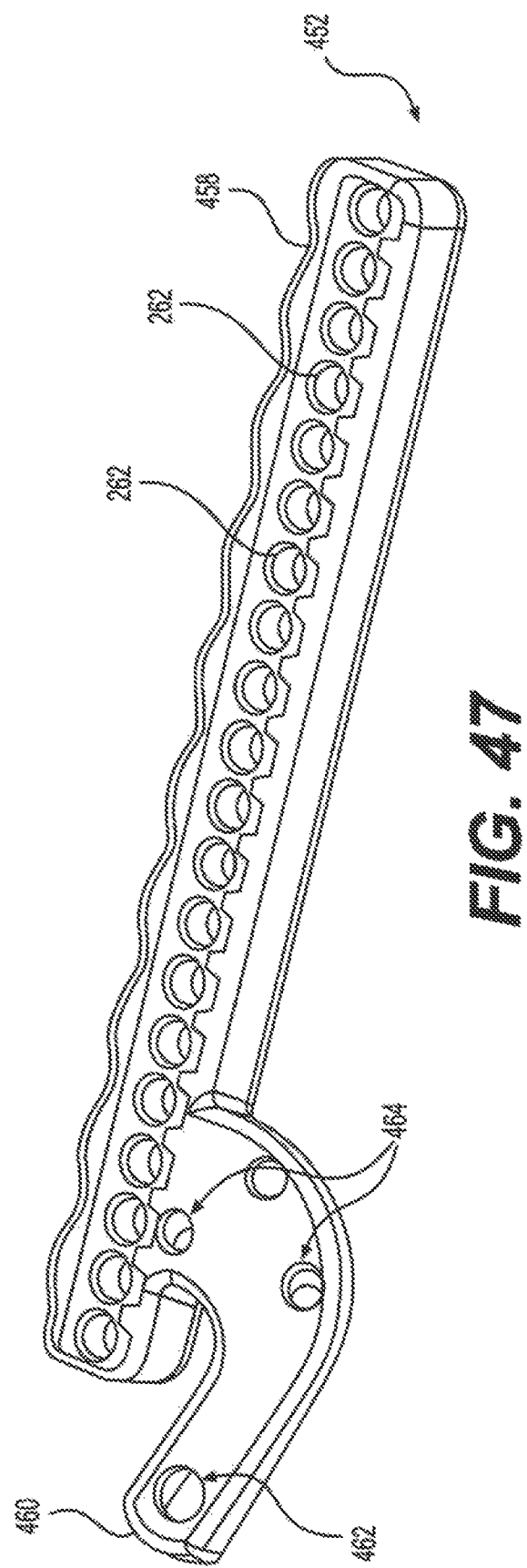
FIG. 47 is a diagram showing a detailed view of the aiming guide according to one embodiment of the present invention.

FIG. 47 is a diagram showing a detailed view of the aiming guide 452 according to one embodiment of the present invention. The embodiment of the aiming guide 452 shown in FIG. 47 may provide one advantage of allowing a single rigid connection between the aiming guide 452 and the bone plate 10, as described in more detail below. When the rigid connection is in place, the corresponding holes 262 of the aiming arm 458 and the holes 62 of the bone plate 10 are coaxial. In the illustrated embodiment, the aiming guide 452 includes an aiming arm 458 and an attachment guide 460. The aiming arm 458 is substantially similar to the aiming arm 210 described with respect to FIG. 17, and includes one or more guide holes 262 that help guide one or more fasteners, screws, or other instruments into the corresponding holes 62 of the plate 10 with accuracy. In contrast to the FIG. 17 embodiment, the aiming guide 452 of the FIG. 46-47 embodiment, does not include an aiming mount 230. Instead, the aiming guide 452 includes an attachment guide 460 that is configured and dimensioned to extend from a portion of the aiming arm 458.

In one embodiment, the attachment guide 460 may extend from one side 459 of the aiming arm 458, as shown in FIG. 47. The attachment guide 460 may be positioned such that it is near one end, e.g., the distal 461 or proximal end 463, of the aiming arm 458. In some embodiments, it may be desirable for the attachment guide 460 to comprise an arm that extends from the aiming arm 458, as shown in FIG. 47. At least a portion of the attachment guide 460 may be configured and dimensioned to be angled such that it can guide the attachment post 454 into the instrument attachment hole 44 in the bone plate 10. Alternately, the attachment hole 462 itself, through which the attachment post 454 passes, may be configured and dimensioned to include an angle that allows the attachment post 454 to be guided into the instrument attachment hole 44. In such an embodiment, the attachment guide 460 may be angled and may lie in the same plane as the aiming arm 458. In other embodiments, both the attachment guide 460 and the attachment hole 462 may be configured and dimensioned to include angles. Alternately, the attachment guide 460 may be configured and dimensioned such that the attachment hole 462 is coaxial with a hole in the neck portion of the bone plate 10, such as the instrument attachment hole 44.

The aiming guide 452, according to one embodiment, may include "left" or "right" configurations to assist with guiding the insertion of screws or other instruments through plates 10 of various configurations. In a left configuration, shown in FIG. 47, the attachment guide 460 is configured and dimensioned as an arm that extends from one side 459 of the aiming arm 458. Although a left configuration is shown in FIGS. 46-47, a right configuration may comprise an attachment guide 460 that extends from the opposite side 465 of the aiming arm 458. In some embodiments, both a "left" and a "right" configuration may be included if desired, i.e., both a left and right arm may be attached to the aiming arm 458, with one extending from a first side 459 and another extending from the opposite side 465.

The attachment guide 460 includes an attachment hole 462 through which the attachment post 454 may pass. In one embodiment, the attachment hole 462 also allows the attachment post 454 to be operatively connected to the attachment guide 460. Other holes may also be configured and dimensioned in the attachment guide 460, such as kickstand targeting holes 464. The kickstand targeting holes 464 may allow one or more instruments to pass through to engage with kickstand holes 52, 62 in the bone plate 10, as described above.

Figure 48A:
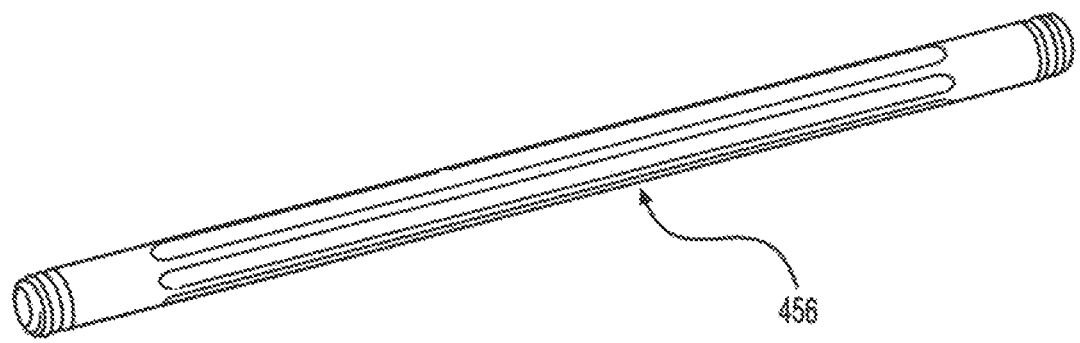
FIGS. 48A-48C show one embodiment of the attachment post and threaded shaft in more detail.
Figure 48B:
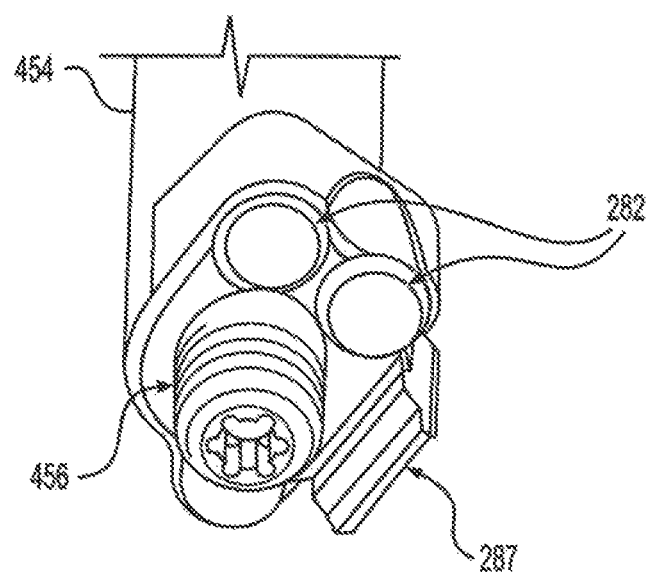
Figure 48C:
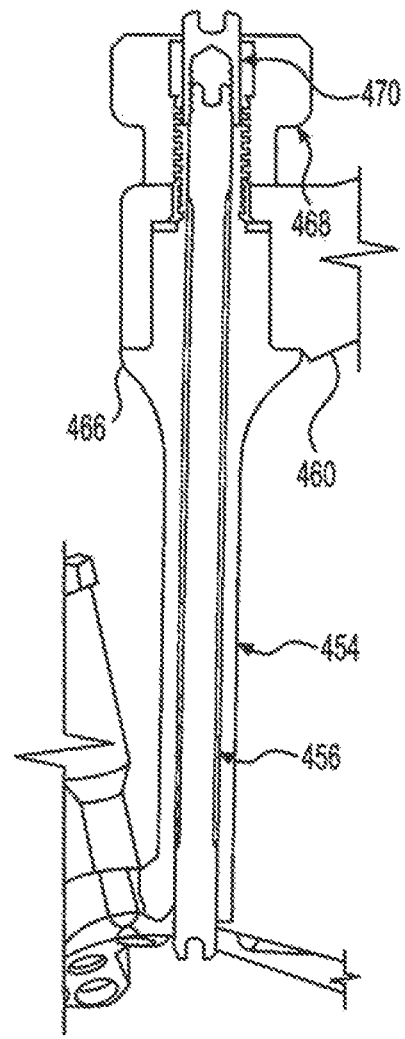

FIGS. 48A-48C show one embodiment of the attachment post 454 and threaded shaft 456 in more detail. The threaded shaft 456 shown in FIG. 48A is substantially similar to the threaded shaft 284 described above. FIG. 48B shows a bottom perspective view of an attachment post 454 in accordance with one embodiment. The attachment post 454 is substantially similar to the attachment post 280 described with respect to FIG. 22 above.

In this embodiment, the attachment post 454 is configured to engage an underlying bone plate 10. The attachment post 454 also includes one or more ball-end pins 282 for engaging alignment indentations 44 (shown in FIG. 1) of the bone plate 10. In addition, the attachment post 454 includes a threaded opening operable to receive the threaded shaft 456 for threadingly attaching to an instrument attachment hole 44 in the bone plate 10. In other embodiments, at least a portion of the opening in the attachment post 454 may not be threaded, which provides the advantage of allowing the attachment post 454 to slide over the threaded shaft 456. The attachment post 454 further comprises a stabilizing feature 287 that assists with alignment during attachment.

The bottom surface of the attachment post 454 may be offset and contoured to match the contour of the bone plate 10 at the attachment location. The attachment post 454 may be operatively connected to the bone plate 10 using a nut threading onto the threaded shaft 456. In addition, at least a portion of the outer surface of the attachment post 454 may be threaded so that it can be attached to the attachment guide 460 using the attachment hole 462. In this embodiment, the end of the attachment post 454 distal from the end attached to the bone plate 10 may be threaded and may be operatively connectable to corresponding threading on the inner surface of the attachment hole 462.

As shown in FIG. 48C, an upper portion 467 of the attachment post 454 may include a lip 466 that is configured and dimensioned along its upper end, distal from the end that is attached to the bone plate 10. The upper portion 467 of the attachment post 454 may also be tapered such that it results in an interference fit with the attachment hole 462. The attachment post 454 may be secured to the attachment guide 460 using an arm attachment nut 468, as shown in FIG. 48C. A post attachment nut 470 may also be included to secure the attachment post 454 to the arm attachment nut 468, the threaded shaft 456, or both.

As described above, the aiming guide 452 includes one or more guide holes 262 that help guide one or more fasteners, screws, or other instruments into the corresponding holes 62 of the plate 10 with accuracy. In one embodiment, the guide holes 262 of the aiming guide 452 may accept one or more tissue protection sleeves 472. The tissue protection sleeves 472 provide a portal into small incisions through which various instruments may pass. Examples of instruments that may pass through the tissue protection sleeves 472 include, but are not limited to, trocars 496, drill sleeves 488, DCP sleeves 492, drills 490, drivers, screws, and the like. The tissue protection sleeves 472 may operatively connect to the guide holes 262 in a desired orientation. When operatively connected to the guide holes 262, the tissue protection sleeves 472 allow an accurate and rigid interface with the aiming guide 452.

FIGS. 49A-49B are diagrams showing exemplary tissue protection sleeves according to one embodiment of the present invention. The tissue protection sleeve 472 may be inserted through a guide hole 262 and then operatively connected thereto. As shown in FIG. 49A, one embodiment of the tissue protection sleeve 472 may include a head 474 and a tip 476. The tip 476 may be configured and dimensioned to fit into the holes 62 of the bone plate 10. The head 474 may comprise a relief cut 478 and a retention ledge 480. The relief cut 478 is configured and dimensioned such that a portion of the head 474 comprises a movable arm 482 that can flex between an open (expanded) and closed (compressed) position. The movable arm 482 is operable to flex about a pivot point at the bottom of the relief cut 478, as shown best in FIG. 49B. The movable arm 482 may also include a retention ledge 480 on its outer surface.

The guide holes 262, according to one embodiment, may be configured and dimensioned to include complementary features that interact with the head 474 of the tissue protection sleeve 472. In this embodiment, each guide hole 262 may include a recess 484 in a top portion of the hole 262. The recess 484 is configured and dimensioned to allow a bottom portion of the head 474 to sit inside the guide hole 262. A portion of the hole 262 may also include an undercut 486 that is operable to interact with the retention ledge 480 configured on the movable arm 482. The undercut 486 may be configured and dimensioned to house the retention ledge 480 when the movable arm 482 is in its steady-state, expanded configuration, as shown in FIG. 49B. Similarly, the retention ledge 480 may be configured and dimensioned to fit within the undercut 486 in its steady-state, expanded configuration. The retention ledge 480 is also configured and dimensioned such that it can move axially within the hole 262 when the movable arm 482 is compressed towards the head 474.

When the tissue protection sleeve 472 is inserted into the hole, the head 474 rests inside the recess 484, according to one embodiment. During insertion, the movable arm 482 is compressed towards the head 474, allowing the retention ledge 480 to pass into the hole 262. When the head 474 fully rests inside the recess 484, the retention ledge 480 is positioned below the undercut 486, allowing the arm 482 to expand into its steady-state, expanded position, as shown in FIG. 49B. When inserted in this manner, tactile feedback or an audible sound, e.g., a click, may be felt or heard as the retention ledge 480 grabs the undercut 486. In order to release the tissue protection sleeve 472, the arm 482 may be compressed towards the head 474, allowing the retention ledge 480 to be removed from the undercut 486. With the retention ledge 480 no longer operatively connected to the undercut 486 and restricted from axial movement, it may be moved out of the hole 262.

Figure 50:
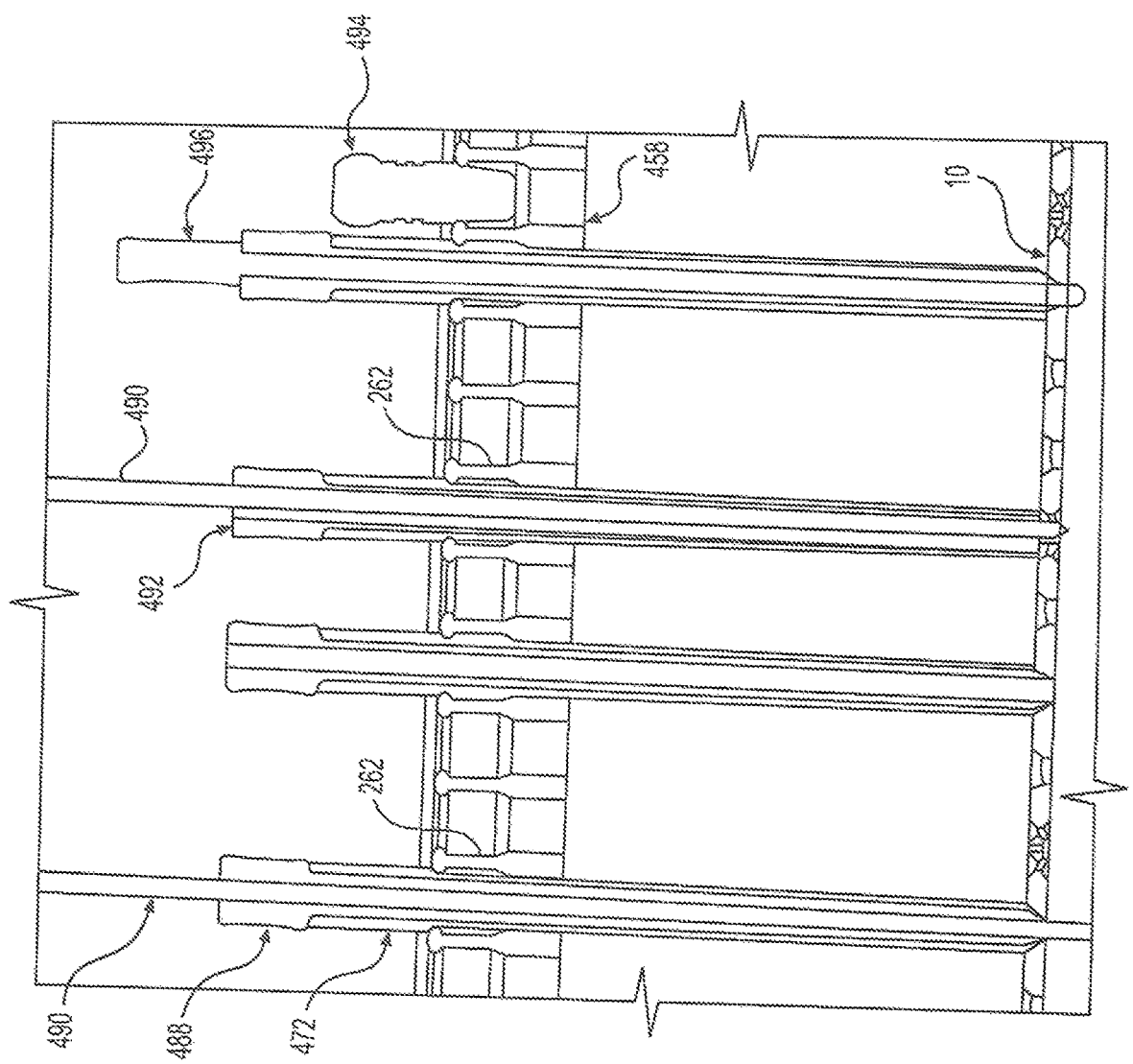
FIG. 50 is a diagram showing exemplary instruments passing through tissue protection sleeves that have been inserted into the guide holes of the aiming arm.

As discussed above, a tissue protection sleeve 472 provides a portal into small incisions through which various instruments may pass. FIG. 50 is a diagram showing exemplary instruments passing through tissue protection sleeves 472 that have been inserted into the guide holes 262 of the aiming arm 458. A drill sleeve 488, for example, may be inserted into the tissue protection sleeve 472 and operatively connected to the bone plate 10. In one embodiment, the drill sleeve 488 aligns a drill 490 to a center axis of the hole 262. Alternatively, a DCP sleeve 492 may be inserted to allow off-axis insertion of a drill 490. One advantage of using an off-axis sleeve is that it allows for off-axis predrilling that can set up compression through a DCP hole that is offset in either direction. For instance, a DCP sleeve 492 may allow compression of 1 mm through a DCP hole in either direction.

In other embodiments, a hole marker 494 may also be inserted into a hole 262 in the aiming arm 458 to allow for marking of a hole. This may be advantageous, for example, to allow for marking of the last hole 262 used, or to indicate a hole which has already been filled with a device, such as a screw. Still other embodiments may allow for other devices, such as a round-tip trocar 496, to be inserted into the tissue protection sleeve 472. Those skilled in the art will understand that one or more tissue protection sleeves 472 and corresponding devices may be using in combination with the present invention as desired. Although FIG. 50 illustrates multiple tissue protection sleeves 472 and devices inserted into the aiming arm 458 at the same time, this is done for illustrative purposes only. One or more sleeves 472 and/or other devices may be used at one time if desired. In other embodiments, only one sleeve 472 and/or device may be used at one time.

According to one embodiment, the aiming guide 452 attaches to the bone plate 10 using a single attachment post 454 and the threaded shaft 456. As described above, the attachment post 454 is aligned to the bone plate 10 based on the ball-end pins 282 and the stabilizing feature 287. According to one embodiment, the threaded shaft 456 is assembled onto the plate 10 first. The attachment post 454 may then slide over the threaded shaft, and the ball-end pins 282 align with alignment indentations 44 in the bone plate 10. The stabilizing feature 287 assists with alignment during attachment of the attachment post 454. The attachment post 454 is then operatively connected to the bone plate 10 using a nut threading onto the threaded shaft 456. In this manner, the attachment post 454 may be rigidly fixed to the bone plate 10 and may be used as an insertion handle. The attachment guide 460 slides over top of the attachment post 454 and is fastened into place with the arm attachment nut 468. A post attachment nut 470 may be optionally used to operatively connect the attachment guide 460 to at least one of the attachment post 454, the arm attachment nut 468, and/or the threaded shaft 456.

According to one embodiment, the aiming arm 452 may comprise a radiolucent material in order to prevent the obstruction of lateral imaging during a medical procedure. The "left" and "right" configurations allow for guiding insertion of screws, fasteners, or other devices through either side of a bone plate 10. The associated tissue protection sleeves 472, drill sleeves 488, and other instrumentation described herein may be used with the aiming guide 452 in both the left and right configurations.

In one embodiment, the aiming guide 452 may also be used with a proximal aiming guide 498. In this embodiment, the proximal aiming guide 498 comprises a plate that may be operatively connected to the bone plate 10 separately from the aiming guide 452. The proximal aiming guide 498 may be used with or without the aiming guide 452. FIG. 51A is a top perspective view of the proximal aiming guide 452. The proximal aiming guide 452 includes one or more guide holes 500.

In one embodiment, the proximal aiming guide 452 includes a fastening mechanism that allows it to be operatively connected to the bone plate 10. For example, the proximal aiming guide 452 may include clips 502 that are configured and dimensioned to allow the guide 452 to be operatively connected to the bone plate 10. In one embodiment, the clips 502 may be formed as a part of the proximal aiming guide 452. Alternately, the clips 502 can be separate elements. In other embodiments, clips 502 may be formed as a part of the bone plate 10. The clips 502 may be positioned near one or more edges of the proximal aiming guide 452 in order to secure it to the bone plate, as shown in FIG. 51A.

The proximal aiming guide 498 may also include openings 504 that are selectively positioned in one or more different locations. The openings 504 may be configured and dimensioned near the perimeter of the proximal aiming guide 498, as shown in FIG. 51A, in order to guide the proximal aiming guide 498 into the correct placement on the bone plate 10. The openings 504 may be configured to receive protrusions, such as pegs 506, that facilitate the alignment of the guide holes 500 and the corresponding holes in the bone plate 10. In this embodiment, the pegs 506 may be configured and dimensioned as part of the bone plate 10. In another embodiment, the bone plate 10 may include openings through which pegs that protrude from the proximal aiming guide 498 may pass in order to facilitate alignment of the guide holes 500 and the corresponding holes 62 in the bone plate 10.

FIG. 51B is a diagram showing another top perspective view of the proximal aiming guide 498. When the proximal aiming guide 498 is operatively connected to the bone plate 10, it allows for the insertion of tools, such as drill sleeves 508, through the guide holes 500, as shown in FIG. 51B. The insertion of drill sleeves 508 allows for the targeting of the nominal angle of the proximal holes in the bone plate 10. After drilling, the drill sleeve 508 may be removed and a screw or other fastener may be inserted through the proximal aiming guide 498. When all fasteners, e.g., screws, have been placed, the proximal aiming guide 498 may be removed. Removal of the proximal aiming guide 498 may be accomplished by hand, or by using a tool such as a drill sleeve to pry it off of the bone plate 10.

Figure 28:
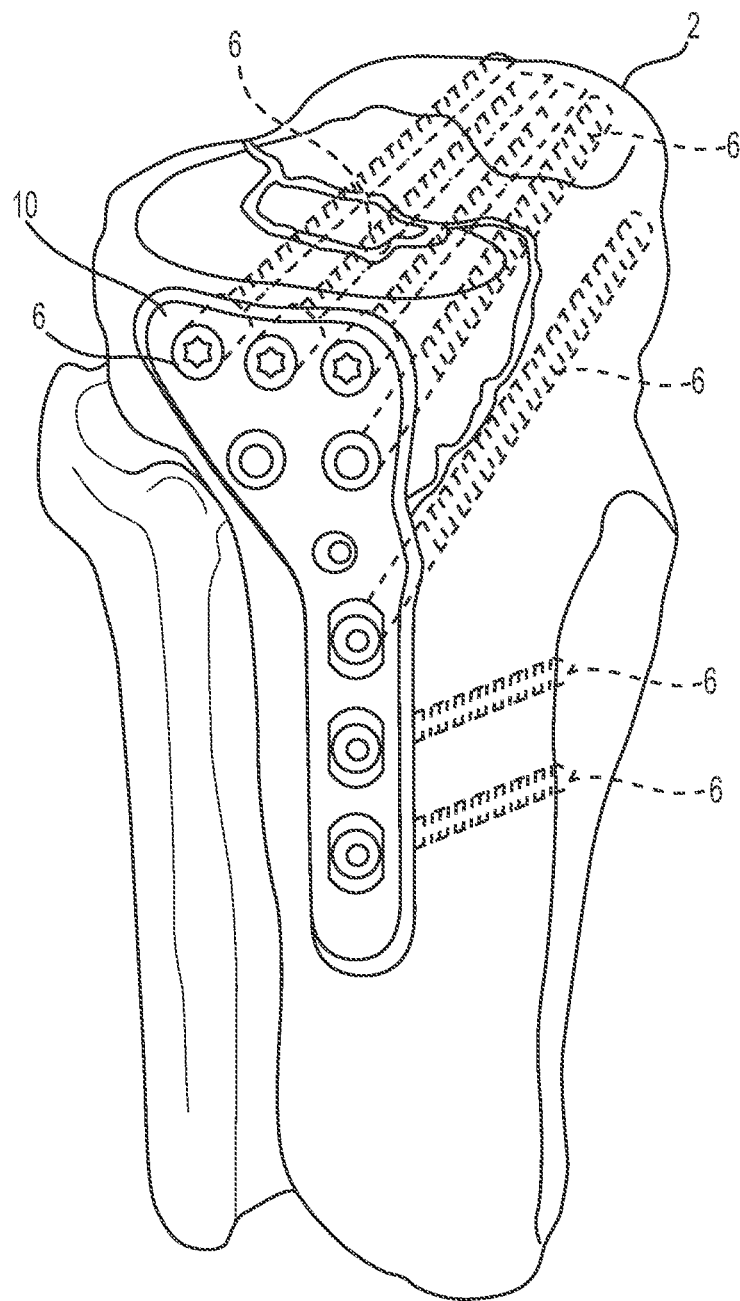
FIG. 28 is a front view of a bone plate including rafting screws attached to a bone member.

FIG. 28 is a front view of a bone plate including rafting screws attached to a bone member. The bone plate 10 can be any of the bone plates described above and can include fasteners or screws 6 extending therethrough. As shown in the figure, the upper row of screws 6 can be considered rafting screws. These rafting screws not only help to treat a bone fracture, but they have to prevent subsidence near the articular joint.

Figure 29:
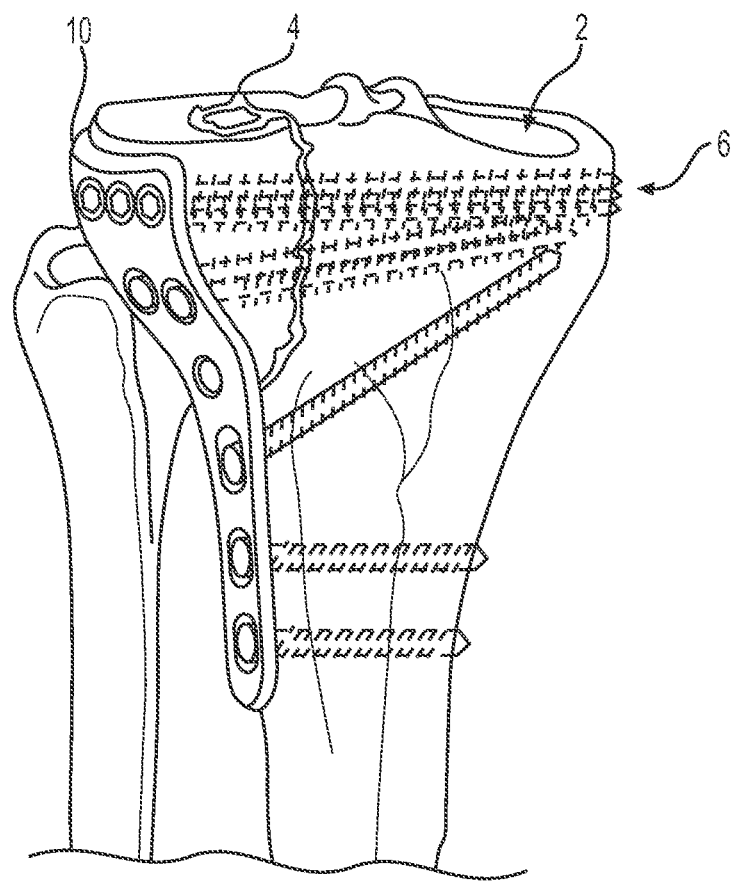
FIG. 29 is a side view of the bone plate of FIG. 28.

FIG. 29 is a side view of the bone plate of FIG. 28. From this view, one can see the rafting screws extending across a fracture in the bone. The rafting screws are positioned adjacent to the articular joint to prevent subsidence near the articular joint.

FIG. 30 is a top view of the bone plate of FIG. 28. From this view, one can see how the rafting screws serve as rebar and provide support for the articular joint.

In addition to these rafting screws, which are threaded, non-threading rafting blades can be provided. In some embodiments, these non-threaded blades help to (i) provide better support of an articular surface, (ii) minimize time in surgery due to ease of insertion; and (iii) have a reduced risk of post-operative back out.

FIG. 31 is a top perspective view of a rafting blade in accordance with some embodiments. The rafting blade 406 can be used in addition to, or as an alternative to, the threaded rafting screws described previously. In some embodiments, one or more rafting blades 406 can be inserted through a bone plate that has been secured to bone via one or more fasteners or screws. The one or more blades can then be locked to the bone plate to prevent post-operative back out.

The rafting blade 406 comprises a proximal end 412 and a distal cutting end 414. The distal cutting end 414 advantageously enables the rafting blade 406 to be inserted into bone with ease, simply by impacting the proximal end 412 of the rafting blade 406. In some embodiments, the rafting blade 406 is curved or arced. In some embodiments, the rafting blade 406 is concave, thereby forming a concave rafting surface. In some embodiments, the rafting blade 406 comprises a structural rib 422 that extends along a longitudinal axis of the rafting blade 406. The structural rib 422 and concave rafting surface advantageously improve the bending moment along the length of the rafting blade 406, thereby providing support against failure during and after insertion.

Figure 32:
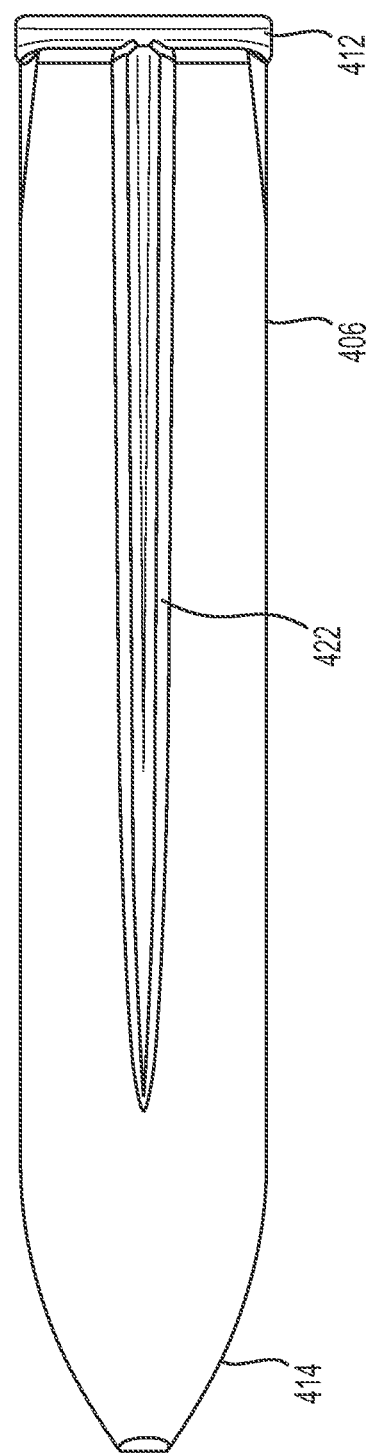
FIG. 32 is a top view of the rafting blade of FIG. 31.

FIG. 32 is a top view of the rafting blade of FIG. 31. From this view, one can see how the structural rib 406 extends along a central longitudinal axis of the rafting blade 406. In some embodiments, the structural rib 406 extends along a majority of the length of the central longitudinal axis of the rafting blade 406.

Figure 33:
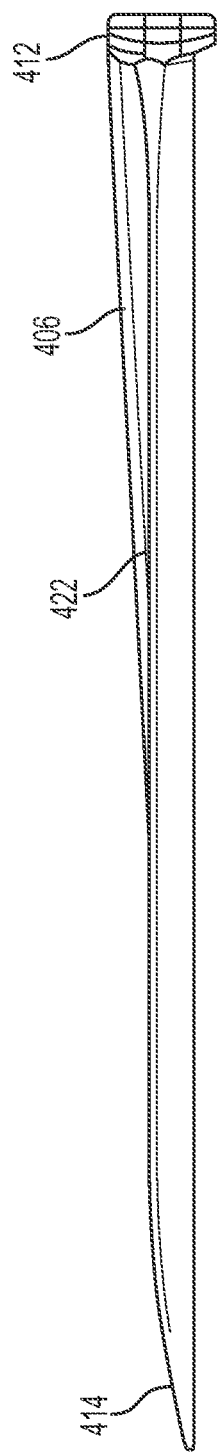
FIG. 33 is a side view of the rafting blade of FIG. 31.

FIG. 33 is a side view of the rafting blade of FIG. 31. From this view, one can see the concave curvature of the rafting blade 406.

Figure 34:
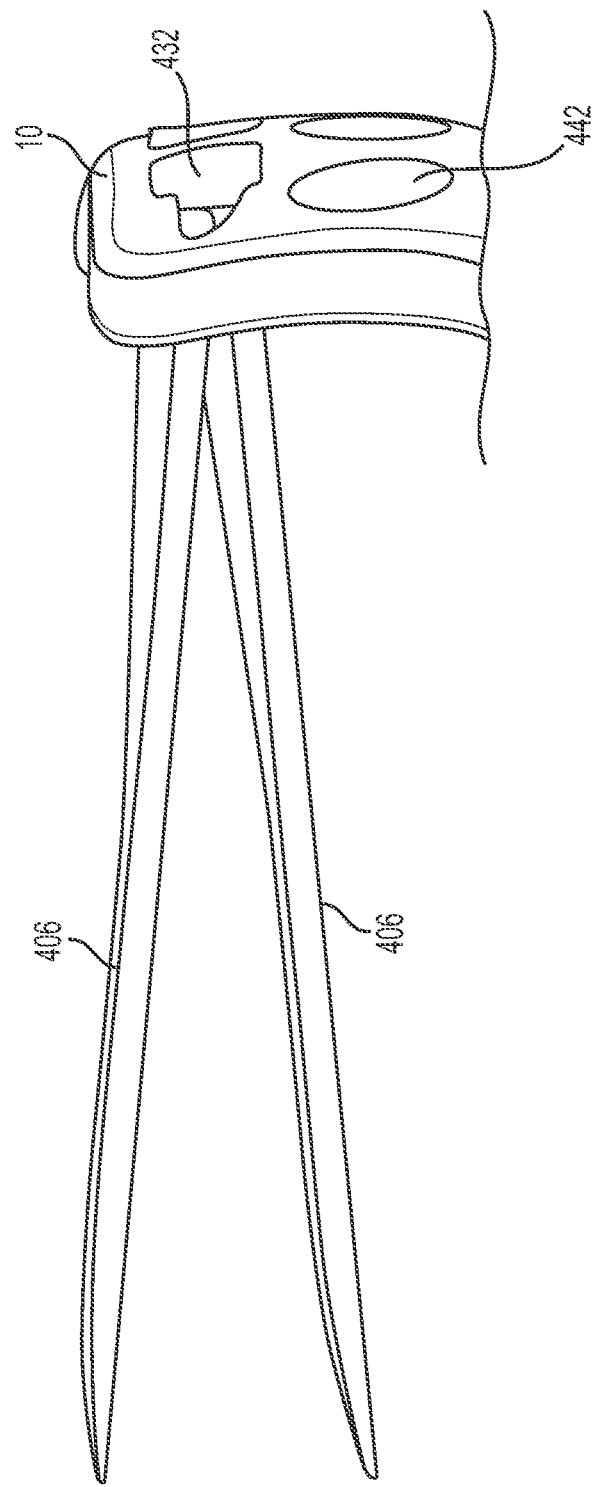
FIG. 34 is a side view of a pair of rafting blades attached to a plate in accordance with some embodiments.

FIG. 34 is a side view of a pair of rafting blades attached to a plate in accordance with some embodiments. The plate 10 comprises a curved or domed plate contact surface that facilitates rotation in one plane allowing the rafting blades 406 to be inserted parallel to an articular surface regardless of plate position. In some embodiments, rafting blades 406 can be inserted at a similar angle to one another. In other embodiments, rafting blades 406 can be inserted at different angles from one another.

Figure 35A:
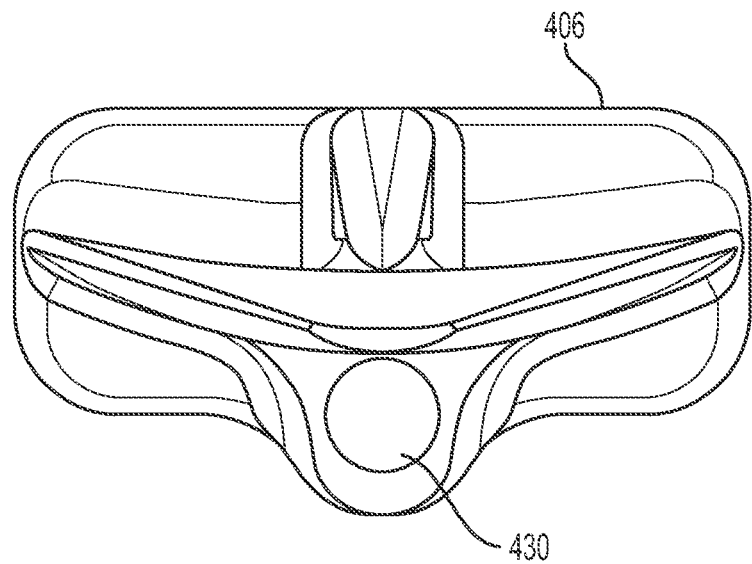
FIG. 35A is a front view of the rafting blade of FIG. 31.

FIG. 35A is a front view of the rafting blade of FIG. 31. From this view, one can see how the rafting blade 406 comprises a k-wire hole 430. The rafting blade 406 can be cannulated to allow guided insertion by k-wire. In some embodiments, the rafting blade 406 can be tapped into bone via use of a slotted hammer.

Figure 35B:
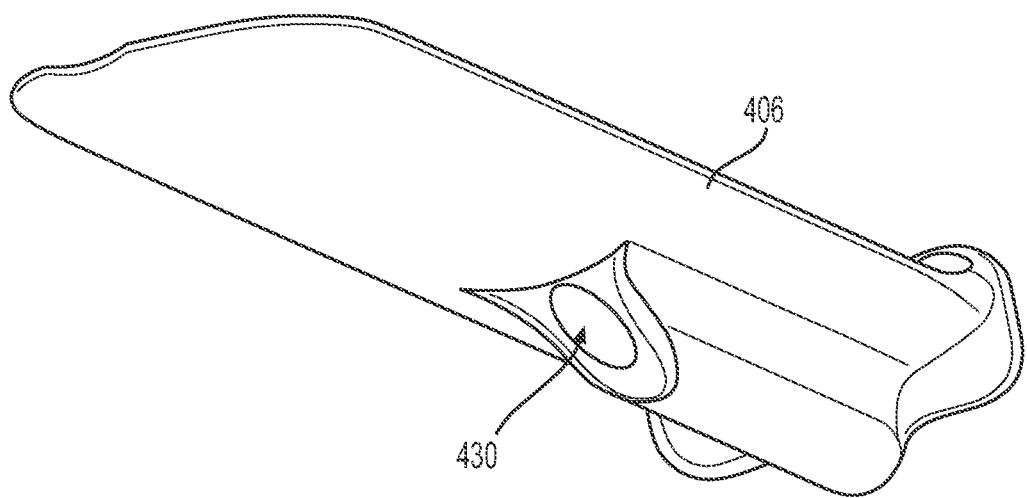
FIG. 35B is a bottom perspective view of the rafting blade of FIG. 31.

FIG. 35B is a bottom perspective view of the rafting blade of FIG. 31. From this view, one can see the underside of the rafting blade 406 and its cannulated k-wire hole 430.

Figure 36:
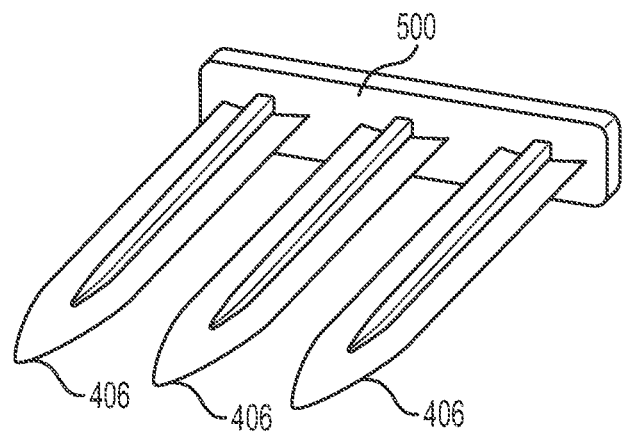
FIG. 36 is a top perspective view of an insertion guide for rafting blades in accordance with some embodiments.
Figure 37A:
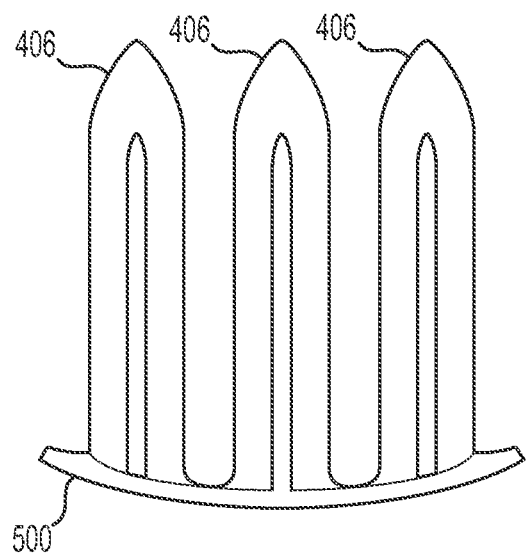
FIGS. 37A and 37B are views of the insertion guide detached from the rafting blades of FIG. 36.
Figure 37B:
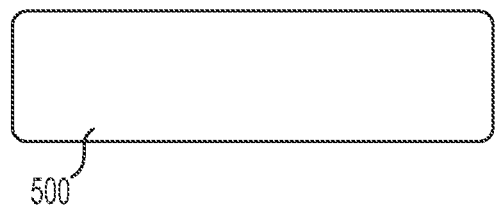

FIG. 36 is a top perspective view of an insertion guide for rafting blades in accordance with some embodiments. FIG. 37 is a top view of the insertion guide detached from the rafting blades of FIG. 36. The insertion guide 500 allows for a set of parallel or variable angled rafting blades 406 to be inserted simultaneously into a bone member. In other embodiments, a rafting blade can be individually installed. By accommodating a set of rafting blades, the insertion guide 500 advantageously reduces the time in surgery. In some embodiments, the insertion guide 500 comprises a block that can temporarily engage or attach to a bone plate after the bone plate has been secured to bone. The block can include a series of channels or openings through which the rafting blades 406 can be inserted therein. In some embodiments, a plurality of rafting blades 406 are preloaded into the insertion guide 500. In other embodiments, the insertion guide 500 can be used without preloading rafting blades 406, thereby allowing a surgeon to select lengths that best suit a particular patient. With the insertion guide 500 in place, the rafting blades 406 can be tapped into bone in sequence. As shown in FIG. 36, in some embodiments, three rafting blades 406 can be inserted in the insertion guide 500. In some embodiments, the middle blade can be shaped in such a way to prevent back out of the other two rafting blades, as shown in FIG. 38.

Figure 38A:
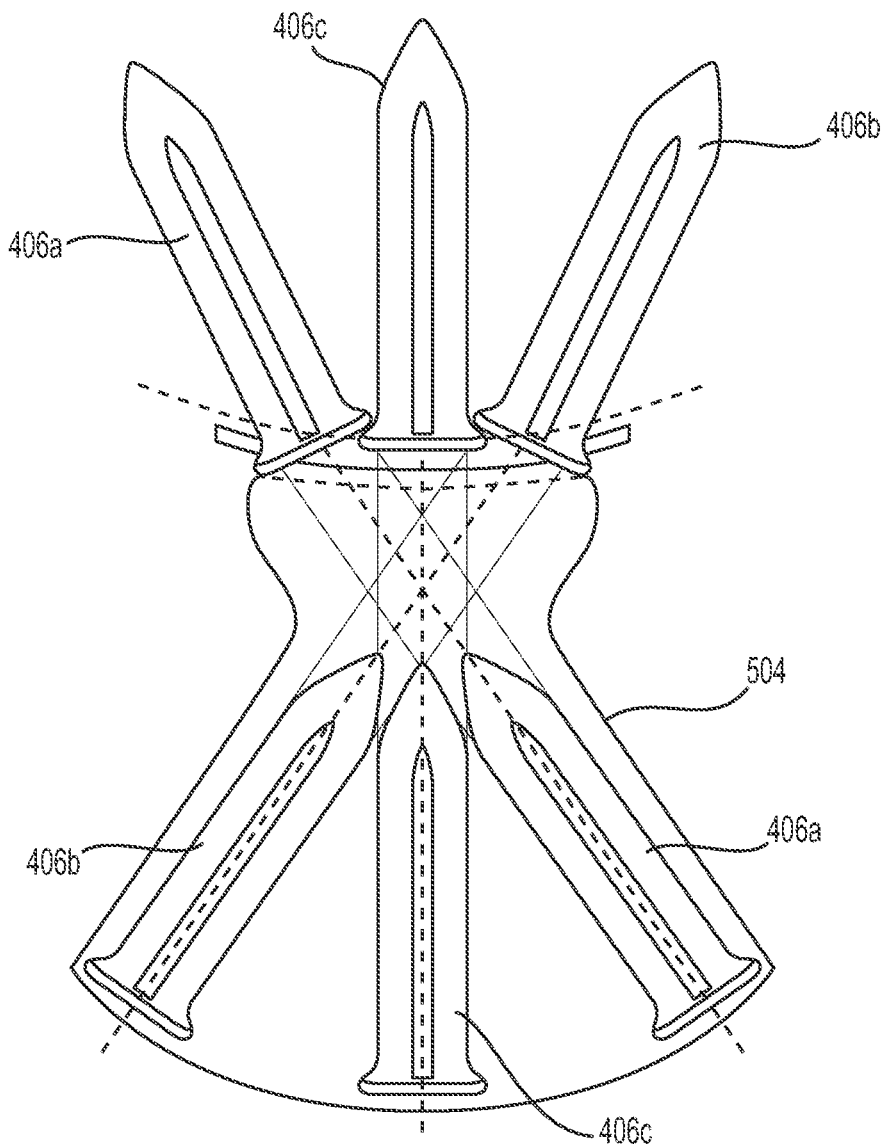
FIGS. 38A and 38B are views of the rafting blades following insertion in accordance with some embodiments.
Figure 38B:
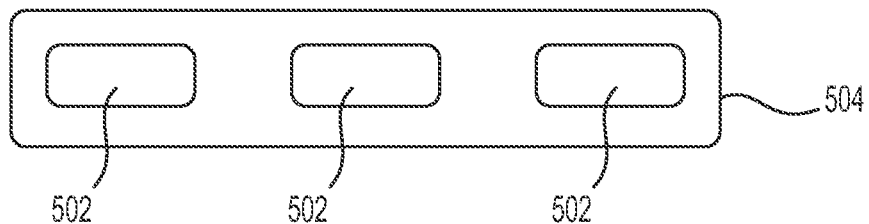

FIG. 38 is a top view of the rafting blades following insertion in accordance with some embodiments. Three rafting blades 406 are provided in the insertion guide 500. The blades 406 include first blade 406a, second blade 406b, and third blade 406c. The blades 406 are tapped in a particular sequence such that the third blade 406c prevents backout of the first and second blades 406a, 406b. In particular, by tapping first blade 406a and second blade 406b prior to tapping the third blade 406c, the third blade 406c can be sized and configured (e.g., via its proximal head portion) to prevent inadvertent backout of the first blade 406a and the second blade 406b.

Figure 39:
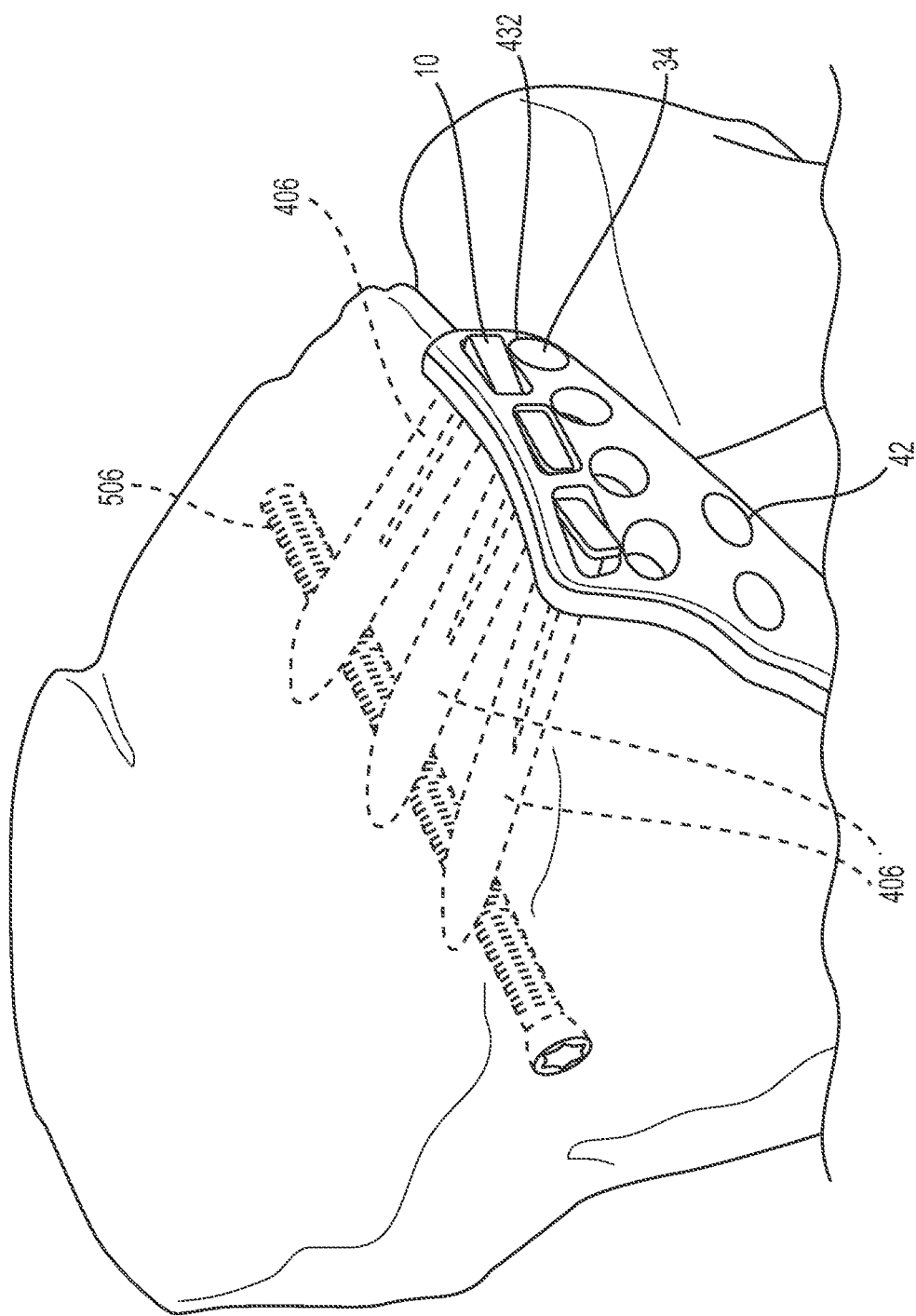
FIG. 39 is a top perspective view of rafting blades and an independent support screw in accordance with some embodiments.

FIG. 39 is a top perspective view of rafting blades and an independent support screw in accordance with some embodiments. In the present embodiment, rafting blades 406 that are inserted into a bone plate 10 through rafting holes 432 are accompanied by a support screw 506. The support screw 506 advantageously supports the tips of the rafting blades 406 after insertion.

Figure 40A:
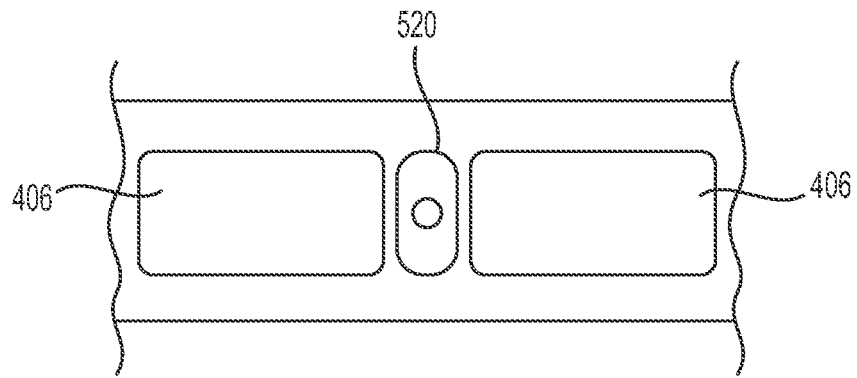
FIG. 40A is a front view of a blocking mechanism for the rafting blades in accordance with some embodiments.
Figure 40B:
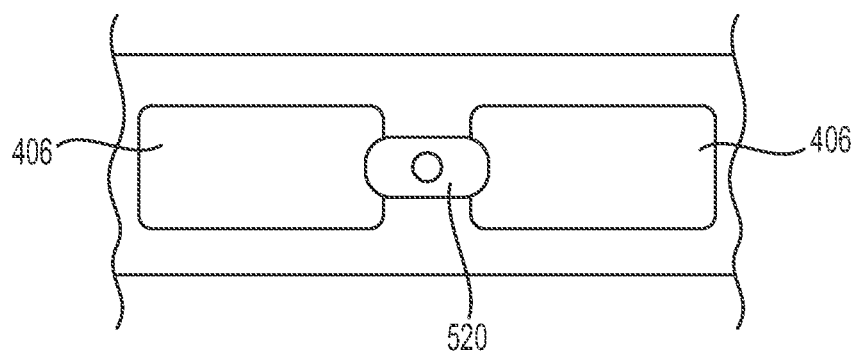
FIG. 40B is a front view of the blocking mechanism of FIG. 40A rotated.

FIG. 40A is a front view of a blocking mechanism for the rafting blades in accordance with some embodiments. FIG. 40B is a front view of the blocking mechanism of FIG. 40A rotated. In some embodiments, the blocking mechanism 520 comprises a blocking screw. In some embodiments, the blocking mechanism 520 comprises a rotating member that allows insertion of rafting blades 406 in one configuration, but prevents the rafting blades 406 from backing out in another rotated configuration. In the embodiment in FIG. 38, in which a middle rafting blade 406c prevents backout of adjacent rafting blades 406a, 406b, the blocking mechanism 520 can simply be installed behind the middle rafting blade 406.

Figure 41:
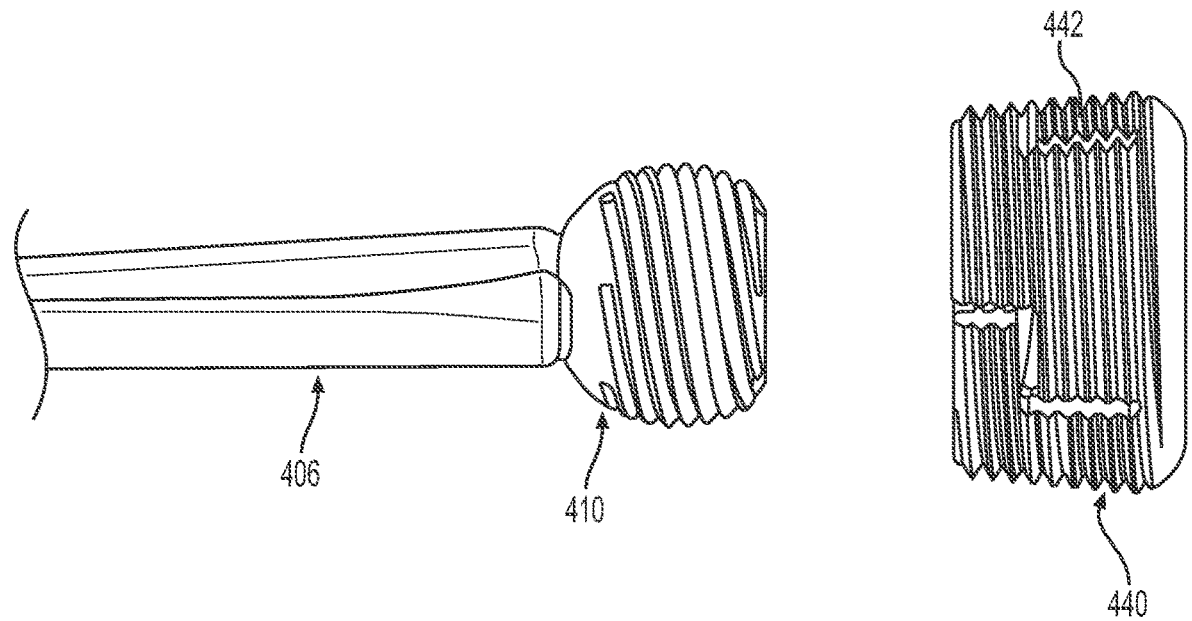
FIG. 41 is a side view of a rafting blade and locking cap in accordance with some embodiments.

FIG. 41 is a side view of a rafting blade and locking cap in accordance with some embodiments. The locking cap advantageously prevents the rafting blade from toggling within a bone plate and keeps it within the bone plate. In some embodiments, a locking cap 440 can be used to collapse over a spherical head 410 of a rafting blade 406. The outside of the locking cap 440 can have a conical surface with cutouts 442 around its diameter. In some embodiments, the cutouts 442 are zig-zagged or z-shaped. In other embodiments, the cutouts 442 are slits. The inside of the locking cap 440 can be spherical to allow the variable angle installation of a rafting blade 406. The locking cap 440 can be threaded. As the locking cap 440 is threaded into a bone plate, its conical geometry and cutouts 442 allow it to collapse over the spherical head 410, grip to the grooved surface of the spherical head 410 and lock it into plate within a bone plate.

Figure 42:
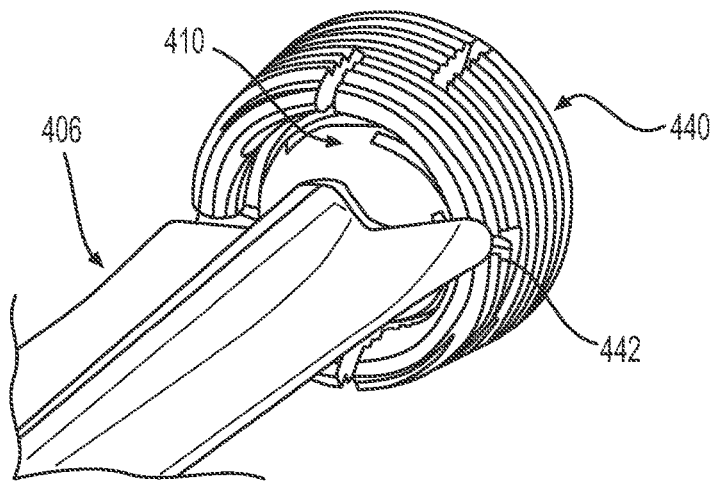
FIG. 42 is a top perspective view of the rafting blade attached to the locking cap of FIG. 41.

FIG. 42 is a top perspective view of the rafting blade attached to the locking cap of FIG. 41. From this view, one can see how the head of the rafting blade 406 is received in the locking cap 440.

Figure 43:
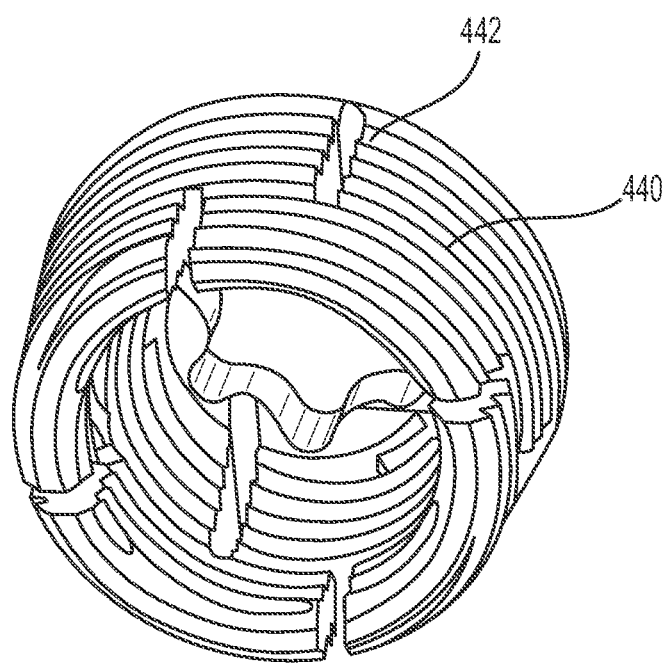
FIG. 43 is a top perspective view of the locking cap of FIG. 41.

FIG. 43 is a top perspective view of the locking cap of FIG. 41. From this view, one can see the inner portion of the threaded locking cap 440. In addition, one can see how the cutouts 442 are formed around a perimeter of the locking cap 440. As shown in FIG. 43, cutouts 442 can be initiated at a top or bottom section of the locking cap 440.

Figure 45:
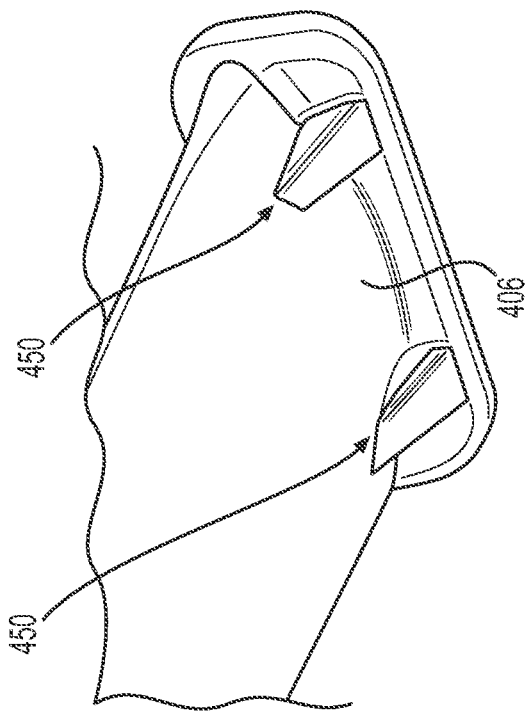
FIG. 45 is a bottom perspective view of the rafting blade having deforming ridges of FIG. 44.
Figure 44:
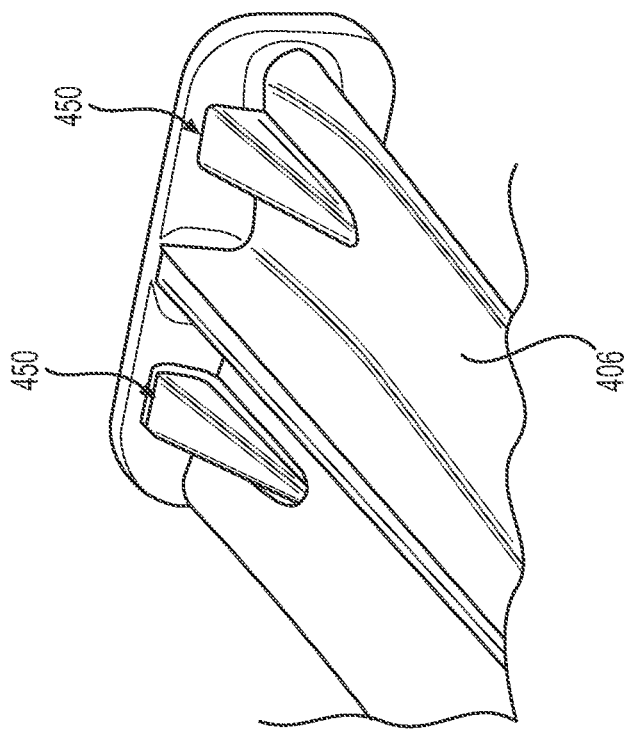
FIG. 44 is a top perspective view of a rafting blade having deforming ridges in accordance with some embodiments.

FIG. 44 is a top perspective view of a rafting blade having deforming ridges in accordance with some embodiments. FIG. 45 is a bottom perspective view of the rafting blade having deforming ridges of FIG. 44. In some embodiments, the rafting blade 406 can comprises one or more ridges 450 where it contacts a bone plate. These one or more ridges 450 can cause a small amount of deformation in the bone plate as the bone plate is inserted, which would advantageously help to lock the rafting blade 406 in place. As shown in FIG. 44, the rafting blade 406 can comprise a pair of ridges 450, each of which is off-center from a longitudinal axis of the rafting blade 406.

According to one aspect of the present invention, a radiolucent panel with radiopaque anatomic and/or mechanical references is included. The radiolucent panel may be used, for example, to assist with the intraoperative restoration of normal femoral and tibial anatomy under fluoroscopy in the operating room. As used herein, each angle is measured relative to a mechanical (m) or anatomic (a) axis. The angle may be measured medial (M), lateral (L), anterior (A), or posterior (P) to the axis line. In addition, the angle may refer to the proximal (P) or distal (D) joint orientation angle of either the femur (F) or tibia (T). For example, mLDFA as used herein refers to the mechanical lateral distal femoral angle in the frontal plane and the PPTA refers to the posterior proximal tibia angle in the sagittal plane. Additionally, the JLCA is the joint line congruency angle referring to the angle between the distal femur and the proximal tibia. The ANSA and MNAS are the anterior and medial neck shaft angles, respectively, which measure the angle between the center of the femoral neck and the proximal femoral shaft.

According to one embodiment, the present invention includes a guide that comprises a panel with one or more references. The references may include, but are not limited to, lines, points, rulers, letters, dashes, pictures, shapes, arrows, and the like. For instance, any medical reference may be included, including those known to medical professionals, e.g., surgeons or the like. In one embodiment, anatomic and mechanical axis lines may be included, for example. The exemplary guide may also include a ruler for measurements during a medical procedure. Any units of measurement may be used for the ruler, including the metric or U.S. system of measurement. The ruler may be used to measure the length of body parts, such as limbs, or alternately may be used to measure medical devices for insertion or as a frame of reference for placement of screws, fasteners, trauma treatment instruments and implants, including external fixators, ring fixators, rods, and other plates.

It may be desirable and advantageous for one embodiment of the guide to be used during medical procedures, such as intraoperative procedures. As such, one embodiment of the guide comprises a radiolucent panel. Any radiolucent material known to those skilled in the art may be used including, but not limited to, plastic, carbon, fibers, composites, and combinations thereof. In some embodiments, it may be desirable for the references included in the guide to be formed from one or more radiopaque materials. In such embodiments, at least one of the references may comprise metallic wire or radiopaque ink, for example. References such as anatomic and/or mechanical axis lines may also include metallic wire or radiopaque ink in some embodiments.

In such embodiments, the metallic wire or radiopaque ink may be positioned on an inner or outer surface of the guide. Alternately, the metallic wire or radiopaque ink may be formed as a part of the guide. It may desirable in other embodiments for the metallic wire or radiopaque ink to be formed between layers of the guide, i.e., if the guide is formed of two or more layers, the metallic wire or radiopaque ink may be positioned in between the two or more layers. When the guide is formed of two or more layers, it may be desirable to include ink on an inner or outer surface of one or more of the layers.

As discussed above, the guide may comprise a panel in one embodiment. The shape and dimensions of the panel may be varied as desired for a particular application. For instance, one embodiment of the guide 510 may comprise a single rectangular panel having a length that is greater in magnitude than its width, as shown in FIG. 52. One embodiment of the guide 510 may comprise a single, reversible guide that has references for left limbs on one side and right limbs on the other side. Alternately, the guide 510 may be one sided and have separate guides for left limbs and right limbs.

FIG. 52 shows one exemplary embodiment of a guide according to one embodiment, as discussed above. As shown in the figure, the guide 510 may comprise a panel that is reversible. In this embodiment, the guide 510 may include a side reference 511 that indicates the proper orientation for which side of the body it is to be used with. In the FIG. 52 embodiment, the guide 510 on the left (in the figure) may be used with limbs on the left side of a person's body, while the guide 510 on the right (in the figure) may be used with limbs on the right side of a person's body. The proper orientation is evident when the "left" or "right" side reference 511 is legible.

The references included on the guide 510 may also include anatomic and mechanical axis lines 512, as shown in FIG. 52. The references may include a ruler 514. As shown in the FIG. 52 embodiment, the ruler may be positioned along the perimeter of the guide 510.

Figure 53:
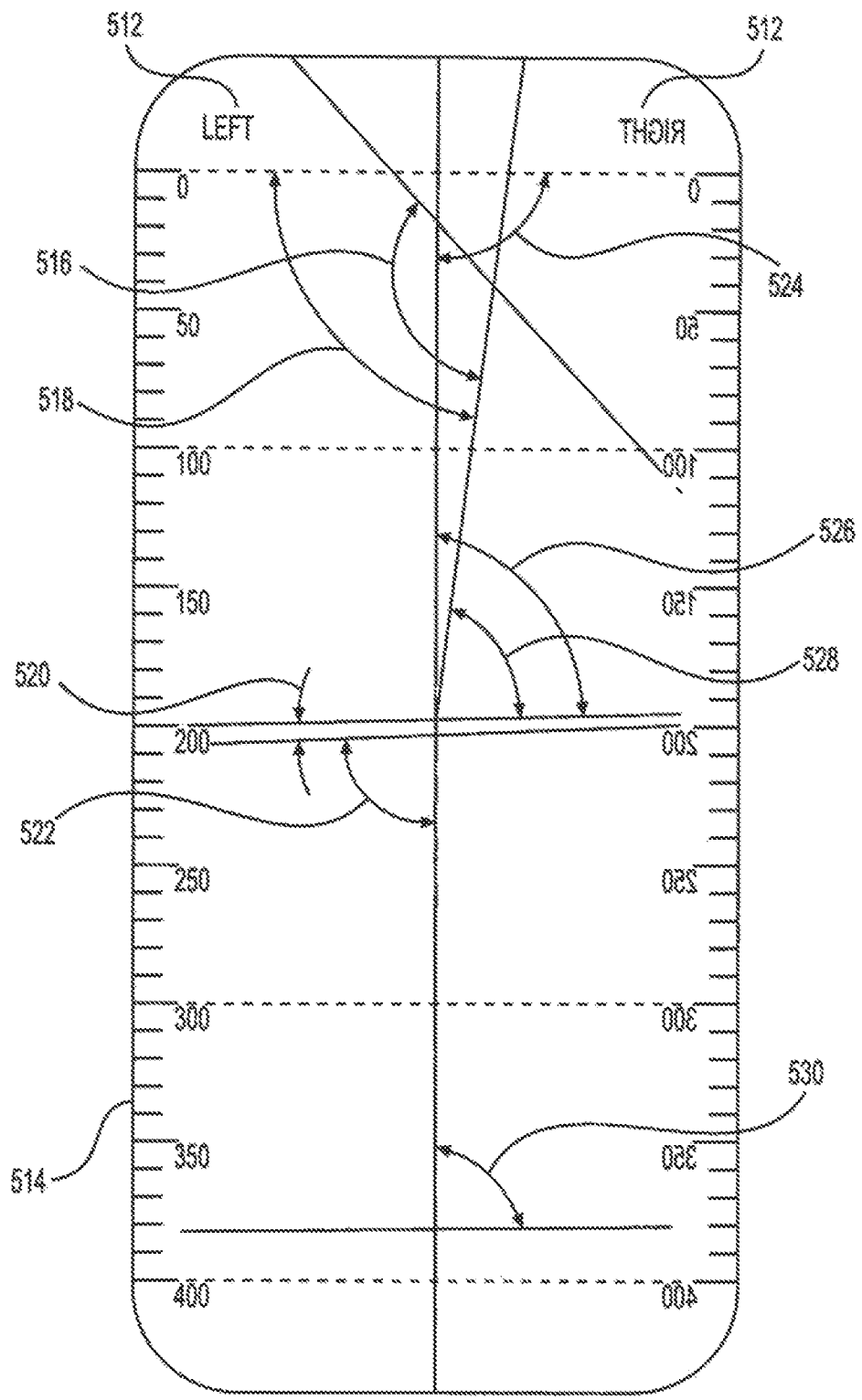
FIG. 53 is a diagram showing a more detailed view of a frontal plane (AP) guide mechanical and anatomic reference angles according to one embodiment of the present invention.

FIG. 53 is a diagram showing a more detailed view of a frontal plane (AP) guide mechanical and anatomic reference angles according to one embodiment. According to one embodiment, the guide 510 may include several mechanical and anatomic axis lines 512 or other indicators for comparison to adjacent anatomy. For example, the reference lines 512 may be at their nominal normal values for comparison to the anatomy shown on a fluoroscopic image. Although the guide 510 may include reference text labeling of the axes in angles in some embodiments, reference text labeling may not be included in other embodiments.

Figure 65:
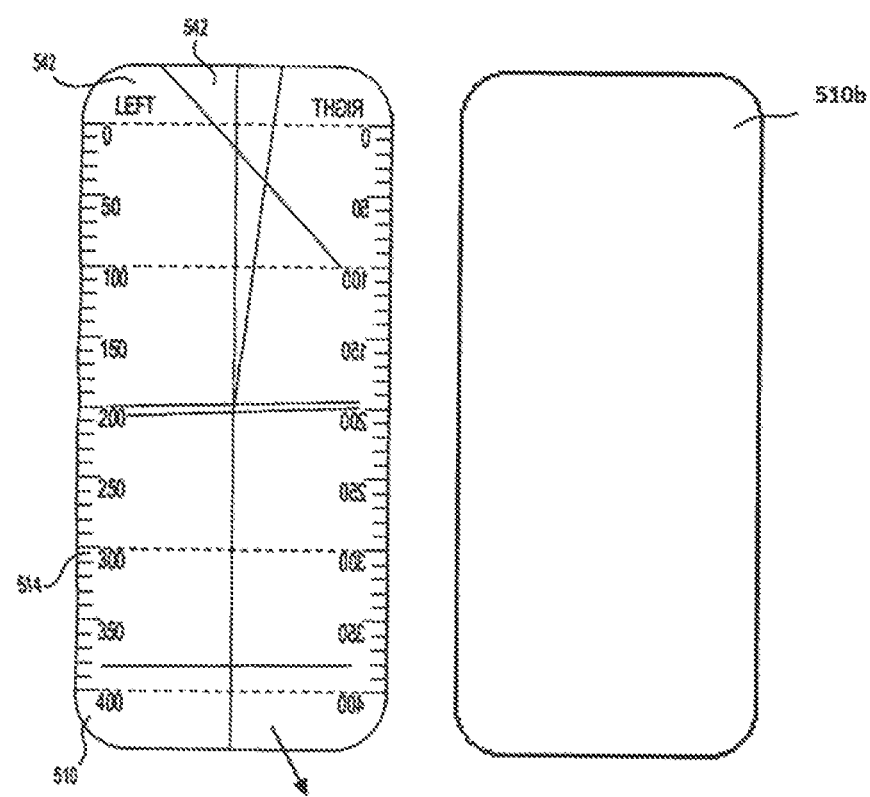
FIG. 65 illustrates the rectangular panels according to one exemplary embodiment of a guide.

As best seen in FIG. 65, the mechanical and anatomic reference lines 512 or any other indicators may be in the form of ink, wires, or the like. For example, the lines 512 may be made of one or more metallic wires, metallic ink, or other radiopaque materials configured to be visible on fluoroscopy or other imaging during a surgical procedure. The guide 510 may comprise a first rectangular panel 510a and a second rectangular panel 510b, for example, formed of a radiolucent material, comprising dimensions substantially similar to one another. The wires, ink, or other reference markers may be positioned in between the first and second rectangular panels 510a, 510b and the first and second rectangular panels 510a, 510b may be operatively connected to one another, for example, by adhesive, melting the panels together, or other suitable means. For example, the wires, ink, or other reference markers may be positioned on one of the panels 510a, 510b before sandwiching them together.

The exemplary guide 510 shown in FIG. 53 may be of assistance with, for example, aligning the knee joint, the proximal and distal femur, the femoral neck, and the proximal and distal tibia. The guide 510 may also enable limb length measurement during repair of a fractured limb by comparison to the contralateral anatomy. As shown in FIG. 53, the guide 510 may include various references that allow for the determination of mechanical or anatomical angles.

As shown in FIG. 53, one embodiment may include reference lines 512 that allow for the determination of the medial neck shaft angle (MNSA) 516, which may be a comparison between two overlapping reference lines 512. The MNSA may be between about 124 degrees to about 136 degrees, or about 130 degrees. In addition, guide 510 may include reference lines 512 that allow for the determination of the anterior medial proximal angle (aMPFA) 518, which may be between about 80 degrees and about 89 degrees, or about 84 degrees. Reference lines 512 may also allow for the determination of the joint line congruency angle (JLCA) 520, which may be between about 0 degrees and about 2 degrees, or about 1 degree. The medial proximal tibial angle (MPTA) 522 may also be measured using the references 512 included in the guide 510. The MPTA 522 may be between about 85 degrees and about 90 degrees, or about 87 degrees, as shown in FIG. 53.

The guide 500 may include any number of references or indicators. In other embodiments, the guide 510 may include reference lines 512 that allow the mechanical lateral proximal femoral angle (mLPFA) 524 to be measured. The mLPFA 524 may range between about 85 degrees and about 95 degrees, or about 90 degrees, for example. The mechanical lateral distal femoral angle (mLDFA) 526 may also be measured using reference lines 512 included in the guide 510, and may range between about 85 degrees and about 90 degrees, or about 88 degrees. Reference lines 512 may also be included to measure the anatomic lateral distal femoral angle (aLDFA) 528, which may range between about 79 degrees and about 83 degrees, or about 81 degrees. One embodiment of the guide 510 also allows for the measurement of the lateral distal tibial angle (LDTA) 530, which may range between about 86 degrees and about 92 degrees, or about 89 degrees.

Figure 54:
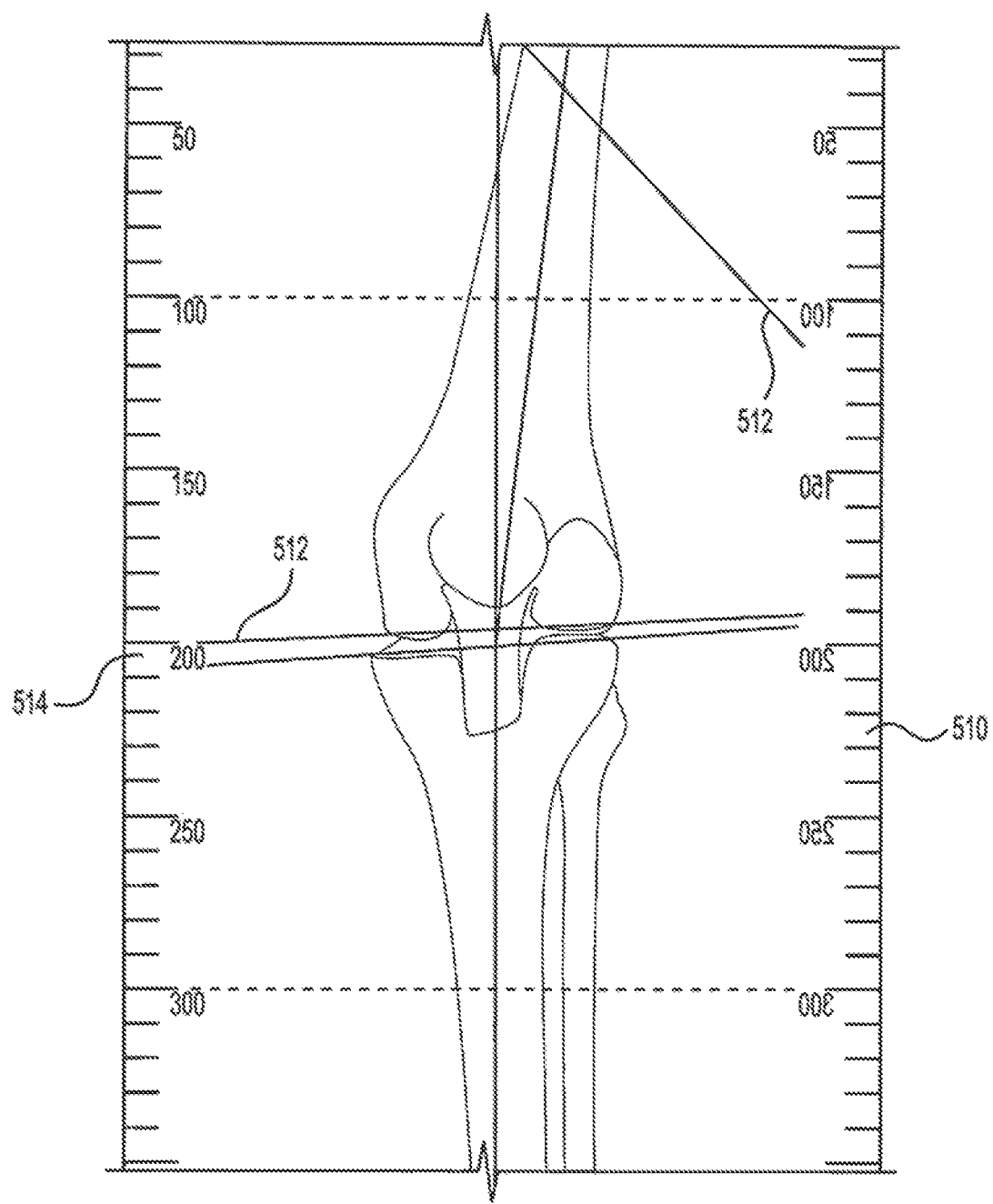
FIGS. 54-57 are diagrams showing examples of the guide being used to measure anatomic angles during interoperative use.
Figure 55:
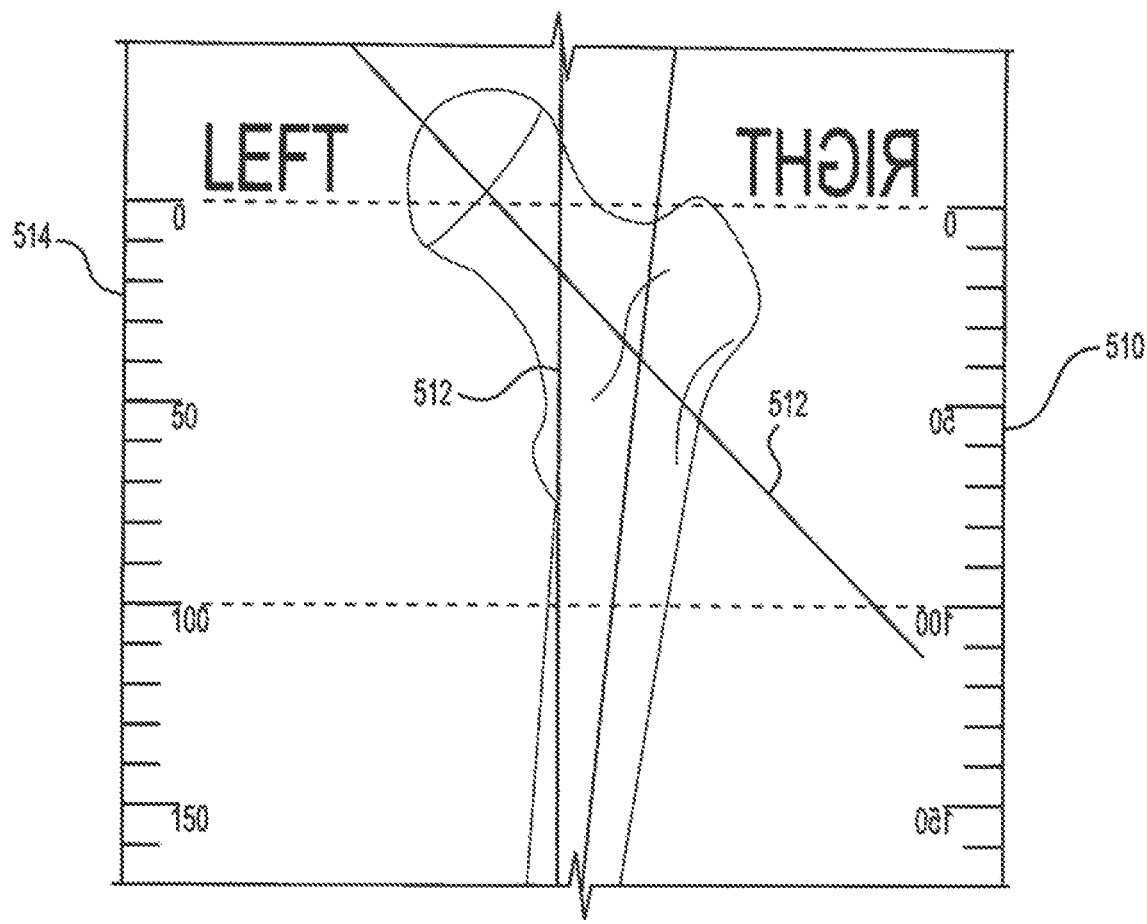
Figure 56:
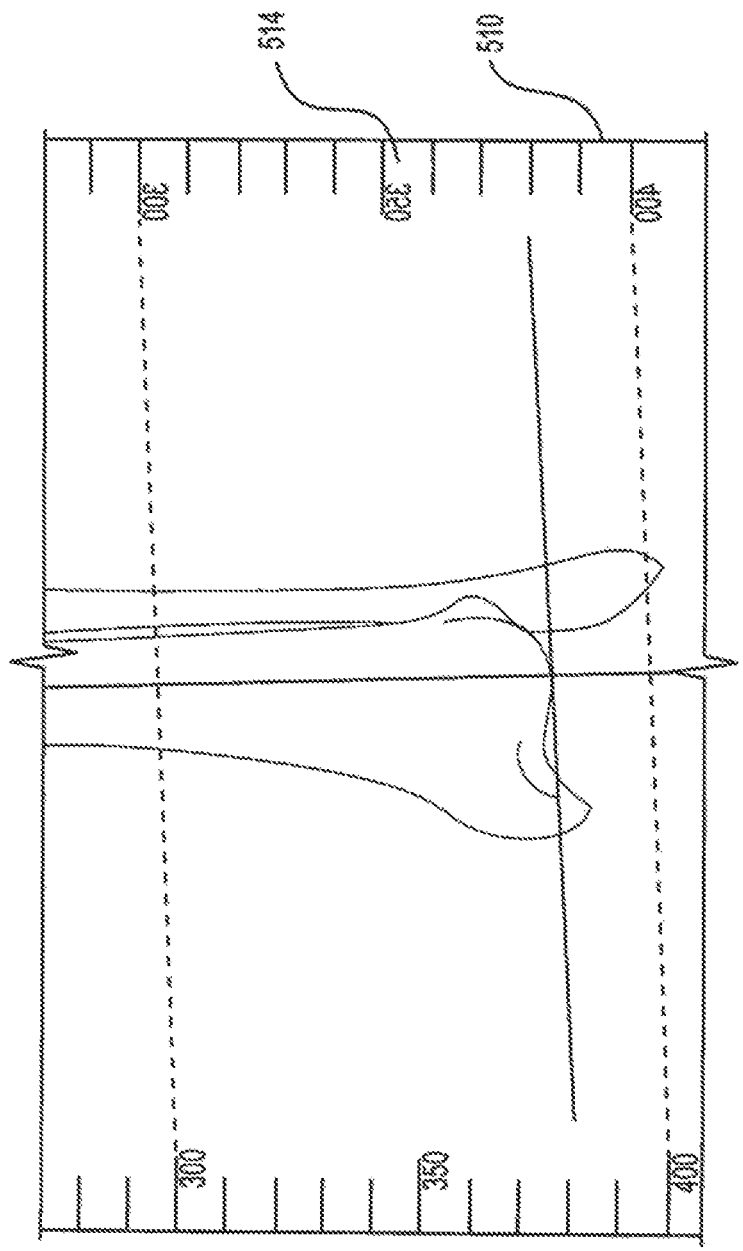
Figure 57:
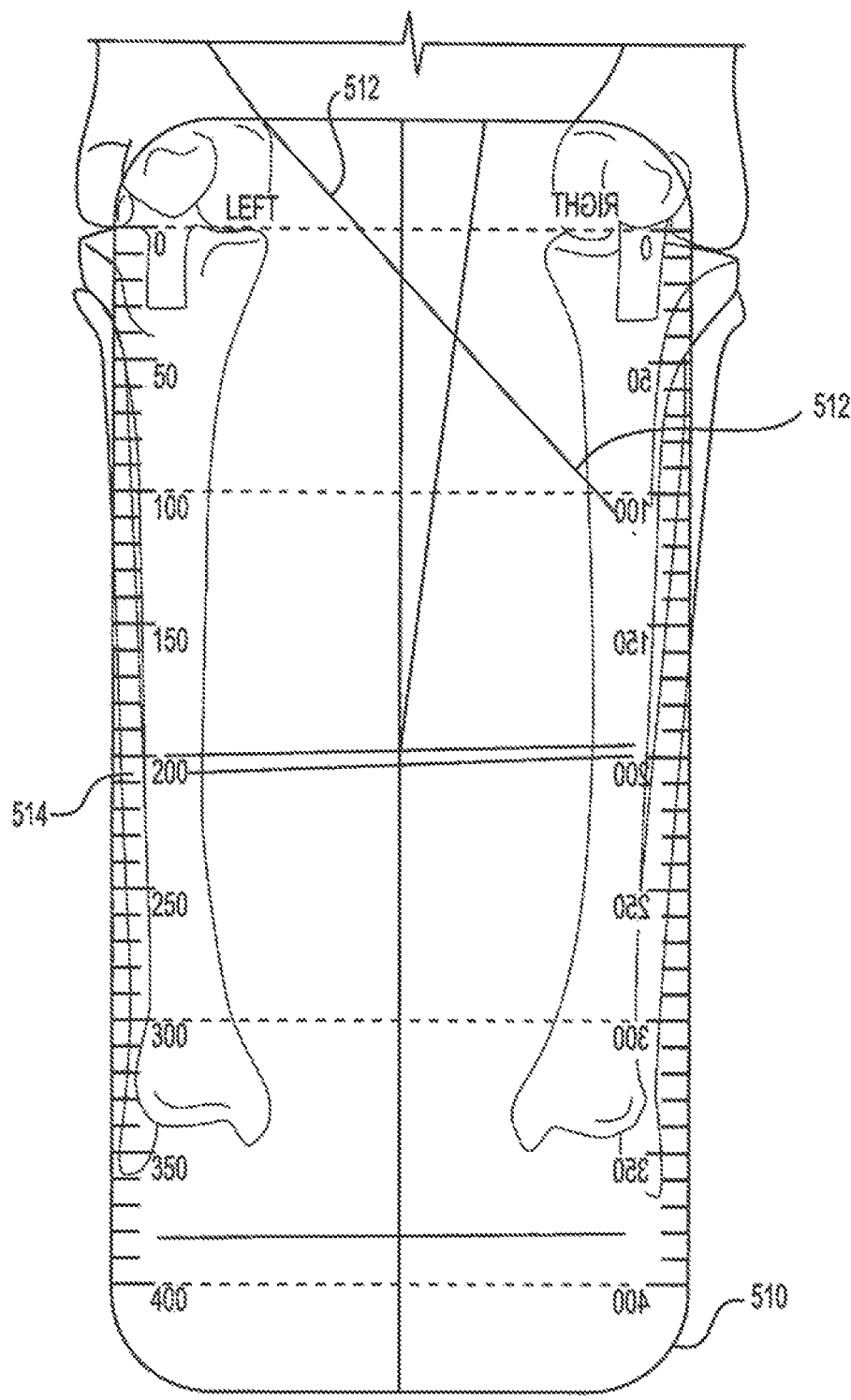

FIGS. 54-57 are diagrams showing examples of the guide 510 being used to measure anatomic angles during interoperative use. FIG. 54, for example, shows how the guide 510 can be used during intraoperative use to measure the knee joint, distal femur, and proximal tibia alignment. FIG. 55 is a diagram that shows how the guide 510 may be used during intraoperative use to measure the proximal femur and femoral neck alignment. FIG. 56 is a diagram that shows how the guide 510 may be used during intraoperative use to measure the distal tibia alignment. FIG. 57 is a diagram that shows how the guide 510 may be used during intraoperative use to perform a limb length comparison using the ruler 514.

Figure 58:
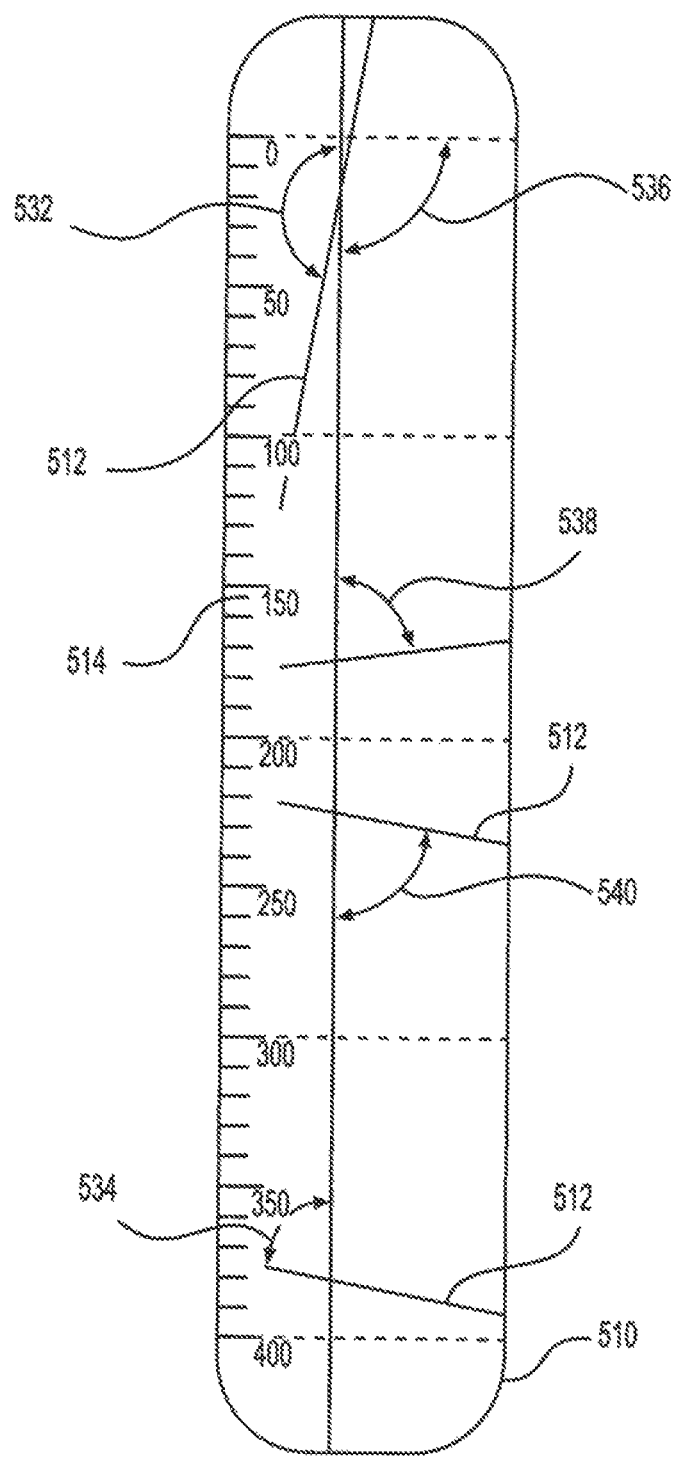
FIG. 58 is a diagram showing another embodiment of guide according to one aspect of the present invention.

During surgical procedures, it is sometimes desirable to obtain lateral images. FIG. 58 is a diagram showing another embodiment of guide 510 according to one aspect of the present invention. One embodiment of the guide 510 shown in FIG. 58 comprises a sagittal plane guide that may assist with lateral imaging. The guide 510 comprises similar materials to the guide described with respect to FIGS. 52-58 above. In contrast to the embodiments described in FIGS. 52-58, the references may comprise mechanical and anatomic axes at their nominal normal angles for the sagittal plane. The references may also include text labeling the axes and angles, as described above. The FIG. 58 embodiment of guide 510 may be used, for example, to align the knee joint, the proximal and distal femur, the femoral neck, and the proximal and distal tibia.

As shown in FIG. 58, the guide 510 may include references that allow for the measurement of various anatomic angles. For example, reference lines 512 may be included that allow the anterior neck shaft angle (ANSA) 532 to be measured, and may range between about 165 degrees and about 175 degrees, or about 170 degrees. In addition, reference lines 512 may be included that allow the anterior distal tibial angle (ADTA) 534 to be measured, and may range between about 78 degrees and about 82 degrees, or about 80 degrees. In some embodiments, reference lines 512 may be included that allow the posterior proximal femoral angle (PPFA) 536 to be measured, and may range between about 88 degrees and about 92 degrees, or about 90 degrees. Reference lines 512 may also be included that allow the posterior distal femoral angle (PDFA) 538 to be measured, which may range between about 79 degrees and about 87 degrees, or about 83 degrees. Additionally, reference lines

512 may be included that allow the posterior proximal tibia angle (PPTA) 540 to be measured, which may range between about 77 degrees and about 84 degrees, or about 81 degrees.

Figure 59:
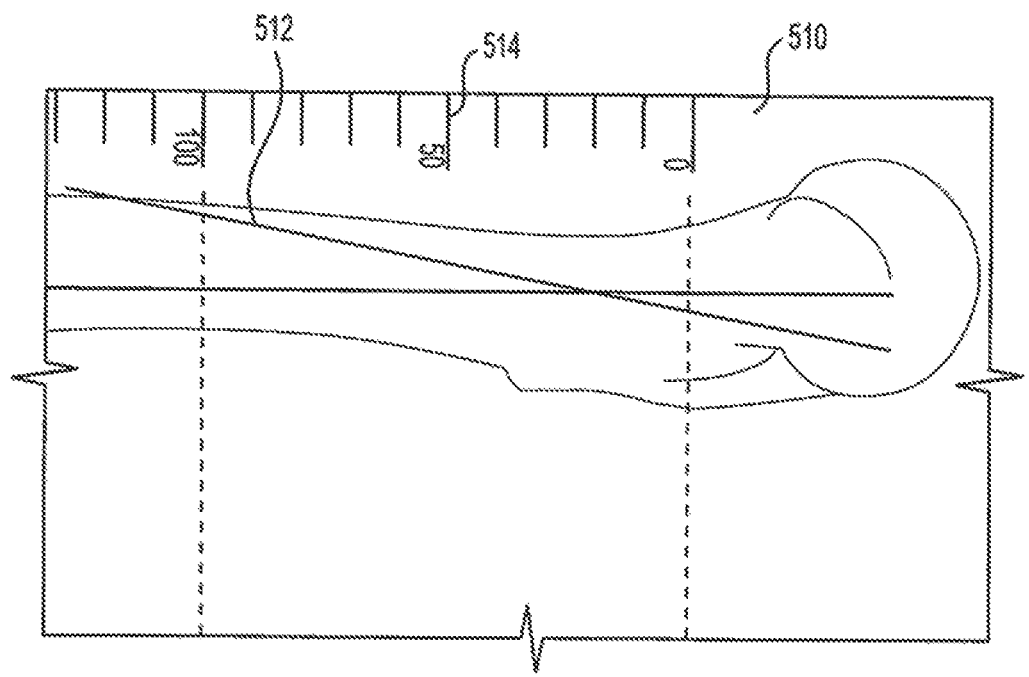
FIGS. 59-60 are diagrams showing the guide of FIG. 58 during intraoperative use.
Figure 60:
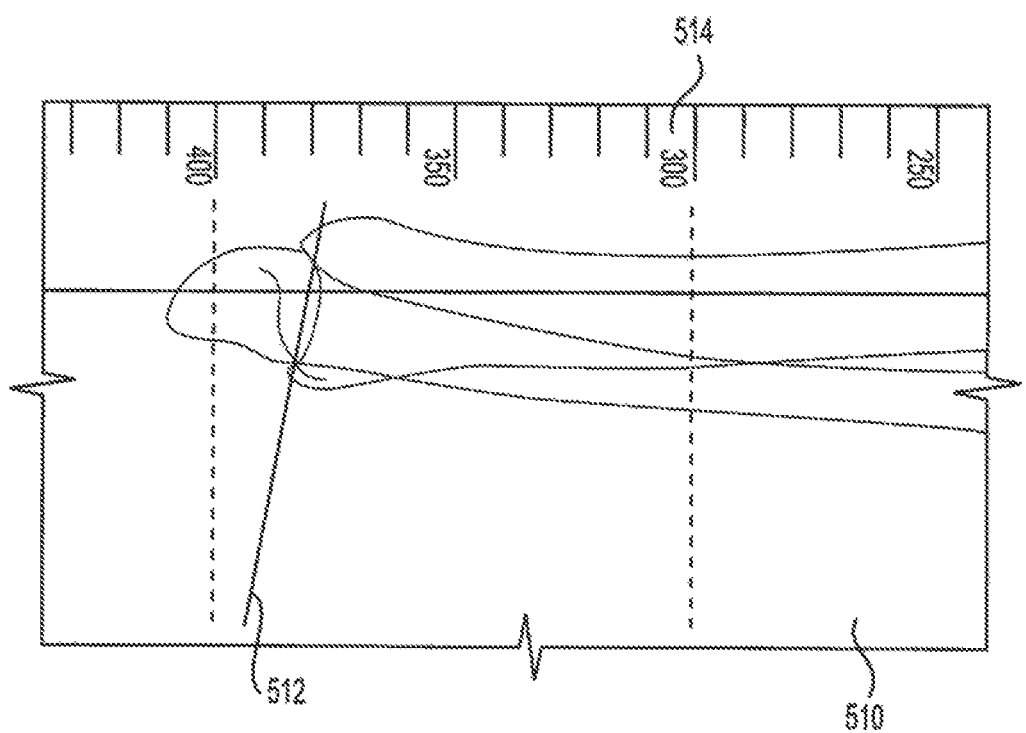

FIGS. 59-60 are diagrams showing the guide 510 of FIG. 58 during intraoperative use. FIG. 59, for example, is a diagram that shows the guide 510 being used to evaluate the proximal femur and femoral neck alignment. FIG. 60 is a diagram that shows the guide 510 being used to evaluate the distal tibia alignment.

Figure 61:
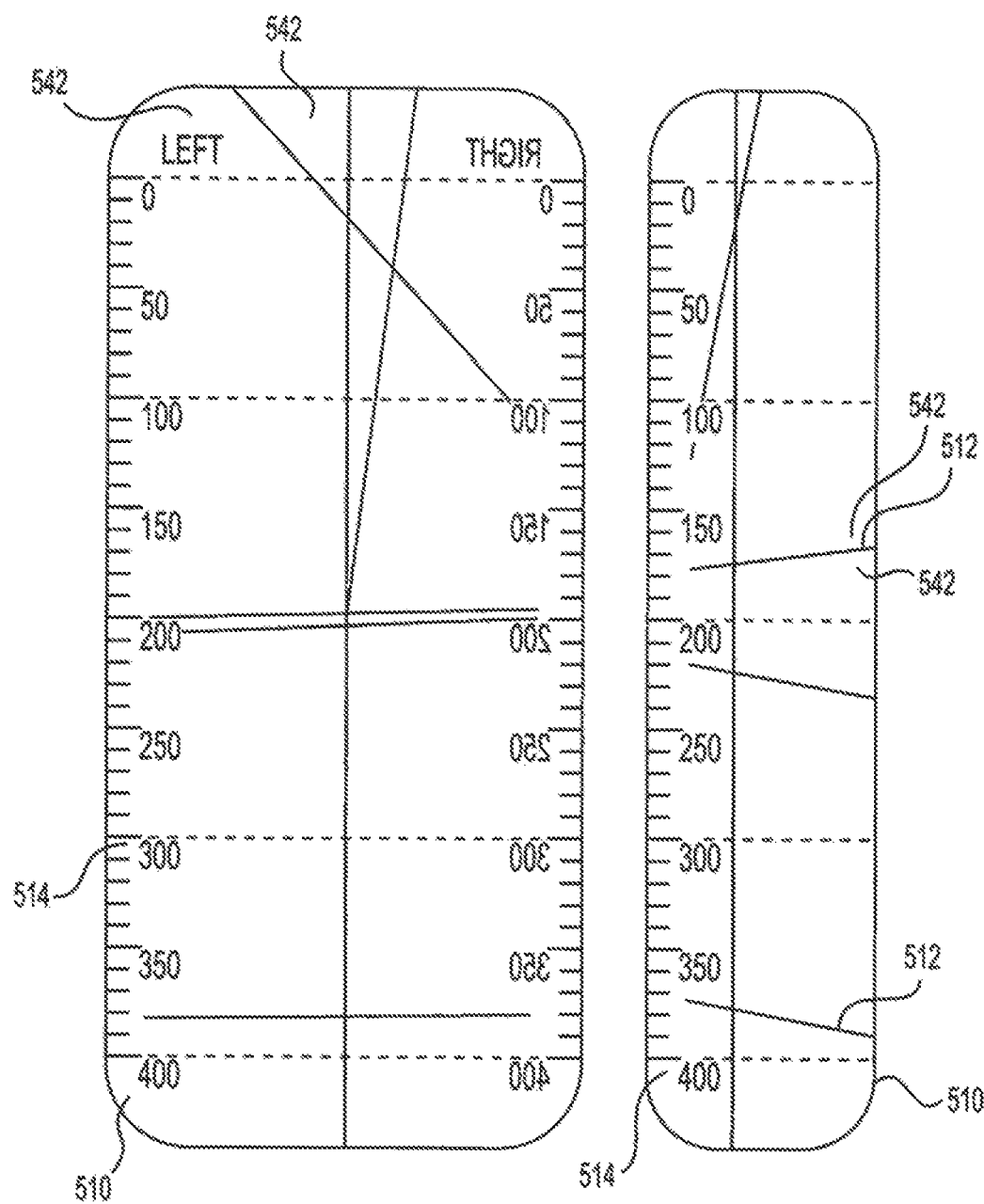
FIG. 61 is a diagram showing a guide that includes dotted reference lines indicating the limits of each mechanical and anatomic axis.

In some embodiments, the guide 510 may include reference lines indicating the normal limits of the mechanical and anatomic axes. FIG. 61 is a diagram showing a guide 510 that includes dotted reference lines 542 indicating the limits of each mechanical and anatomic axis 512. The guide 510 on the left of FIG. 61 is an exemplary frontal guide and the guide 510 on the right of FIG. 61 is an exemplary sagittal guide that include dotted reference lines 542.

Figure 62B:
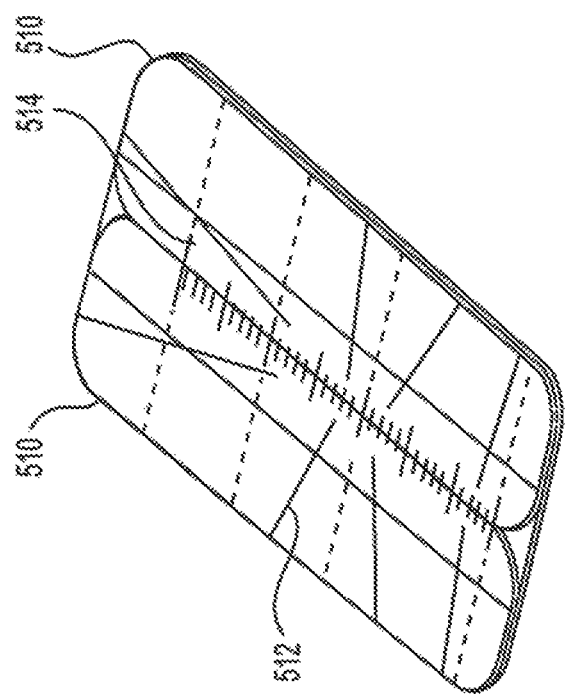
FIG. 62B is a diagram showing an exemplary frontal and sagittal guides that are positioned adjacent to one another.
Figure 62A:
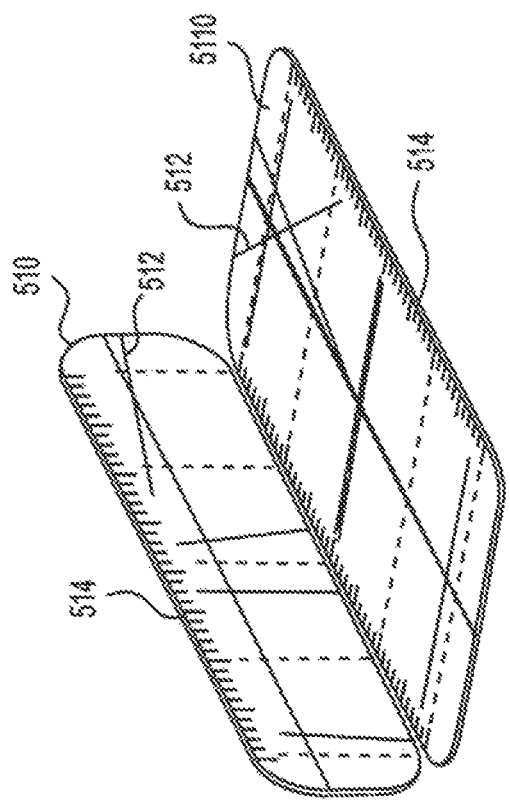
FIG. 62A is a diagram showing an exemplary sagittal and frontal guide that are formed as a single, foldable element.

In various embodiments, the guides 510 may come packaged together or as part of a kit. In one embodiment, a sagittal and frontal guide may be formed as a single, foldable element, as shown in FIG. 62A. In embodiments where the guides 510 are foldable, the sagittal guide may be positioned at an angle, e.g., a 90 degree angle, to the frontal guide using a support, such as a bracket or the like (not shown) in FIG. 62A. One advantage of including a support is that it would facilitate holding the guides 510 in place during imaging, such as lateral fluoroscopic imaging. In other embodiments, such as the embodiment shown in FIG. 62B, the frontal and sagittal guides may be positioned adjacent to one another.

Figure 63:
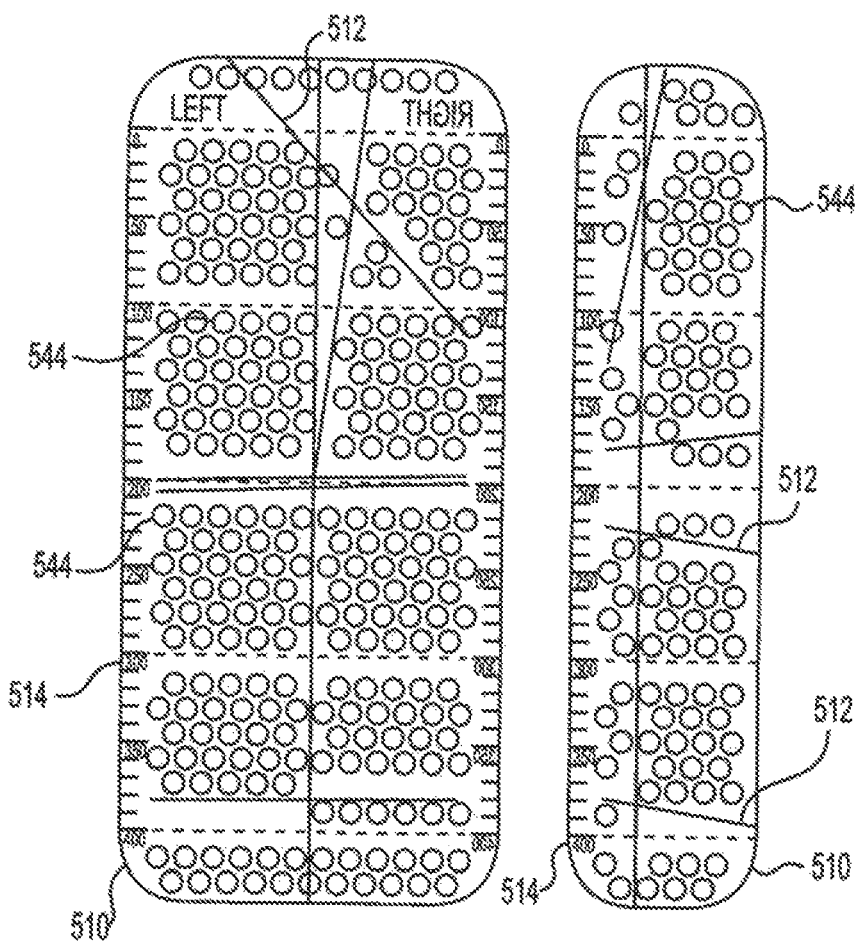
FIG. 63 is a diagram showing an exemplary embodiment of a guide that includes one or more perforations.
Figure 64:
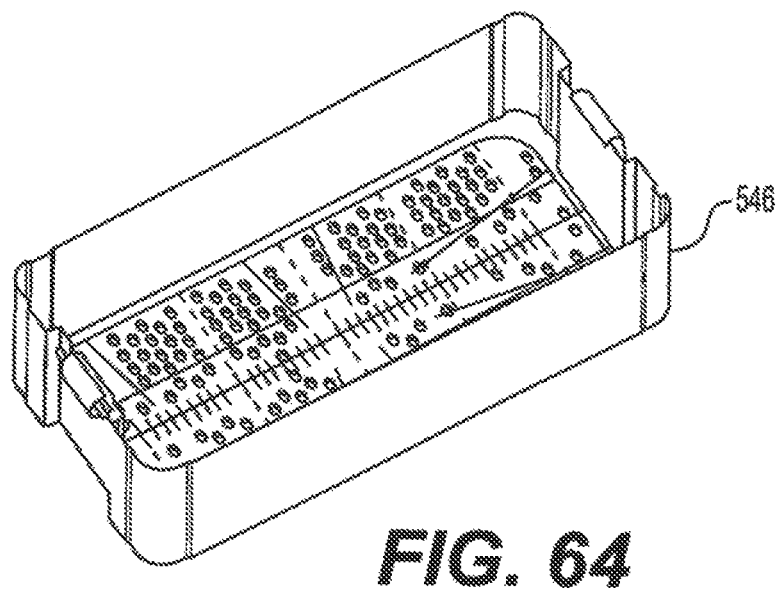
FIG. 64 illustrates an embodiment in which a guide is shown with in a case.

In one embodiment, it may be desirable for the guides 510 to be sterilized and packaged. The guides 510 may comprise various shapes and dimensions, and may be packaged together with guides 510 of similar shapes and dimensions or with guides 510 of varying shapes and dimensions. The guides 510 may be configured and dimensioned in different sizes to fit into different cases 546 as a reusable guide 510, as illustrated in FIG. 64. To aid with sterilization, the guides 510 may include one or more perforations 544, as shown in FIG. 63. The perforations 544 may provide the advantage of allowing sterilization, e.g., steam sterilization, for example, in a graphic case.

One skilled in the art will appreciate that the embodiments discussed above are non-limiting. While bone plates may be described as suitable for a particular approach (e.g., medial or lateral), one skilled in the art will appreciate that the bone plates can be used for multiple approaches. In addition, while bone plates are described as having particular holes (e.g., locking or non-locking), one skilled in the art will appreciate that any of the bone plates can include locking, non-locking or a combination of locking and non-locking holes. In addition to the bone plates, screws and instruments described above, one skilled in the art will appreciate that these described features can be used with a number of trauma treatment instruments and implants, including external fixators, ring fixators, rods, and other plates and screws.

The invention claimed is:

1. A method for treating a fracture in a bone, comprising: placing a bone plate on the bone, wherein the bone plate comprises a proximal end, a distal end, a head portion, a neck portion and a shaft portion, wherein the head portion comprises a first row of openings and a second row of openings for receiving one or more fasteners therein, wherein the shaft portion comprises at least one additional opening for receiving a fastener therein; providing an aiming arm having a proximal end, a distal end, a first side, and a second side, the aiming arm comprising a plurality of openings, wherein each of the plurality of openings is spaced at predetermined intervals between the proximal end and the distal end; connecting an attachment guide to the first side of the proximal end of the aiming arm, wherein the attachment guide comprises at least one opening that is coaxial with an opening in the neck portion of the bone plate; passing an attachment post through the at least one opening of the attachment guide into the opening in the neck portion of the bone plate; and coupling a first end of the attachment post to the at least one opening in the attachment guide and a second end of the attachment post to the opening in the neck portion of the bone plate; and further coupling a proximal targeting guide to an attachment arm of the aiming arm, wherein the proximal targeting guide comprises openings that are coaxial with the first row of openings and the second row of openings in the head portion of the bone plate, wherein the proximal targeting guide comprises two holes that align with two pegs on the head portion of the bone plate in order to align the openings of the proximal targeting guide with the first row of openings and the second row of openings in the head portion of the bone plate.

2. The method of claim 1, further comprising:
   inserting a threaded shaft within an internal cavity in the in the attachment post.

3. The method of claim 2, wherein the attachment post and the threaded shaft form a rigid connection between the bone plate and the attachment guide.

4. The method of claim 1, wherein the second end of the attachment post includes at least one ball end pin and a stabilizing protrusion that engage with the neck portion of the bone plate to form a rigid connection between the threaded shaft, attachment post, and bone plate.

5. The method of claim 1, wherein a bottom side of the at least one opening in the attachment guide is configured and dimensioned to receive a corresponding portion of the first end of the attachment post.

6. The method of claim 1, further comprising:
   attaching an attachment nut configured to a top side of the at least one opening in the attachment guide and the first end of the attachment post to form a rigid connection between the aiming arm, and the attachment post.

7. The method of claim 1, wherein the aiming arm comprises a radiolucent material.

8. The method of claim 1, further comprising:
   connecting a proximal end of a tissue protection sleeve to one of the plurality of openings in the aiming arm; and
   connecting a distal end of the tissue protection sleeve to a corresponding coaxial opening in the shaft portion of the bone plate.

9. The method of claim 8, wherein the tissue protection sleeve comprises a head having a flexible arm that engages with a recess in one of the openings in the aiming arm.

10. The method of claim 8, wherein the tissue protection sleeve includes a retention ledge that is engageable with an undercut in one of the openings in the aiming arm.

11. The method of claim 1, wherein the aiming arm and the attachment guide are a unitary structure.

\* \* \* \* \*